(12) United States Patent
Pier et al.

(10) Patent No.: US 7,786,255 B2
(45) Date of Patent: Aug. 31, 2010

(54) POLY-N-ACETYL GLUCOSAMINE (PNAG/DPNAG)-BINDING PEPTIDES AND METHODS OF USE THEREOF

(75) Inventors: Gerald B. Pier, Brookline, MA (US); Casie Anne Kelly-Quintos, Boston, MA (US); Lisa Cavacini, Natick, MA (US); Marshall R. Posner, Medfield, MA (US)

(73) Assignees: The Bringham and Women's Hospital, Inc., Boston, MA (US); Beth Israel Deaconess Medical Center, Inc., Boston, MA (US)

( * ) Notice: Subject to any disclaimer, the term of this patent is extended or adjusted under 35 U.S.C. 154(b) by 598 days.

(21) Appl. No.: 11/111,688

(22) Filed: Apr. 21, 2005

(65) Prior Publication Data

US 2006/0115486 A1 Jun. 1, 2006

Related U.S. Application Data

(60) Provisional application No. 60/564,105, filed on Apr. 21, 2004.

(51) Int. Cl.
*C07K 14/00* (2006.01)
*C07K 17/00* (2006.01)
*C12P 21/08* (2006.01)

(52) U.S. Cl. .................... 530/300; 530/350; 530/387.1; 530/388.1

(58) Field of Classification Search .............. 530/387.1, 530/388.1
See application file for complete search history.

(56) References Cited

U.S. PATENT DOCUMENTS

| | | | |
|---|---|---|---|
| 4,197,290 A | 4/1980 | Yoshida | |
| 4,285,936 A | 8/1981 | Pier et al. | |
| 4,443,549 A | 4/1984 | Sadowski | |
| 4,465,776 A * | 8/1984 | Cidlowski et al. ........... | 436/504 |
| 4,578,458 A | 3/1986 | Pier | |
| 4,652,448 A | 3/1987 | Sadowski | |
| 4,786,592 A | 11/1988 | Deal et al. | |
| 4,789,735 A | 12/1988 | Frank et al. | |
| 4,795,803 A | 1/1989 | Lindberg et al. | |
| 4,830,852 A | 5/1989 | Marburg et al. | |
| 4,859,449 A | 8/1989 | Mattes | |
| 4,879,272 A | 11/1989 | Shimoda et al. | |
| 4,902,616 A | 2/1990 | Fournier et al. | |
| 5,055,455 A | 10/1991 | Pier | |
| 5,362,754 A | 11/1994 | Raad et al. | |
| 5,366,505 A | 11/1994 | Farber | |
| 5,571,511 A | 11/1996 | Fischer | |
| 5,589,591 A | 12/1996 | Lewis | |
| 5,688,516 A | 11/1997 | Raad et al. | |
| 5,718,694 A | 2/1998 | Rupp | |
| 5,830,539 A | 11/1998 | Yan et al. | |
| 5,858,350 A | 1/1999 | Vournakis et al. | |
| 5,866,140 A | 2/1999 | Fattom et al. | |
| 5,980,910 A | 11/1999 | Pier | |
| 5,989,542 A | 11/1999 | Pier et al. | |
| 6,245,735 B1 | 6/2001 | Pier | |
| 6,399,066 B1 | 6/2002 | Pier | |
| 6,743,431 B2 | 6/2004 | Pier | |
| 6,924,360 B2 * | 8/2005 | Green et al. ............. | 530/388.1 |
| 7,252,828 B2 | 8/2007 | Pier et al. | |
| 2002/0119166 A1 | 8/2002 | Pier et al. | |
| 2003/0124631 A1 | 7/2003 | Pier et al. | |
| 2004/0091494 A1 | 5/2004 | Pier et al. | |
| 2004/0175731 A1 | 9/2004 | Pier et al. | |
| 2005/0025775 A1 | 2/2005 | Pier et al. | |
| 2005/0118198 A1 * | 6/2005 | Pier et al. ................. | 424/243.1 |

FOREIGN PATENT DOCUMENTS

| | | |
|---|---|---|
| EP | 0 302 781 A1 | 2/1989 |
| EP | 0 694 309 A2 | 10/1996 |
| FR | 2 410 043 A1 | 6/1979 |
| FR | 2 581 877 A1 | 11/1986 |
| FR | 2 640 628 A1 | 12/1988 |
| GB | 2 009 771 A | 6/1979 |
| WO | WO 85/05037 A1 | 11/1985 |
| WO | WO 86/02358 A1 | 4/1986 |
| WO | WO 88/02028 A1 | 3/1988 |
| WO | WO 89/04873 A1 | 6/1989 |
| WO | WO 90/03398 A1 | 4/1990 |
| WO | WO 90/06696 A2 | 6/1990 |
| WO | WO 93/01276 A1 | 1/1993 |

(Continued)

OTHER PUBLICATIONS

Mikayame et al (PNAS vol. 90, pp. 10056-10060, 1993).*

(Continued)

*Primary Examiner*—Mark Navarro
(74) *Attorney, Agent, or Firm*—Michaud-Kinney Group LLP

(57) ABSTRACT

The present invention relates to peptides, particularly human monoclonal antibodies, that bind specifically to poly-N-acetyl glucosamine (PNAG), such as Staphylococcal PNAG, in acetylated, partially acetylated and/or fully deacetylated form. The invention further provides methods for using these peptides in the diagnosis, prophylaxis and therapy of infections by bacteria that express PNAG such as but not limited to Staphylococci and *E. coli*. Some antibodies of the invention enhance opsonophagocytic killing and in vivo protection against bacteria that express PNAG such as but not limited to Staphylococci and *E. coli*. Compositions of these peptides, including pharmaceutical compositions, are also provided, as are functionally equivalent variants of such peptides.

15 Claims, 15 Drawing Sheets

FOREIGN PATENT DOCUMENTS

| WO | WO 93/09811 A1 | 5/1993 |
|---|---|---|
| WO | WO 93/19373 A1 | 9/1993 |
| WO | WO 94/15640 A1 | 7/1994 |
| WO | WO 98/52605 A1 | 11/1998 |
| WO | WO 99/40440 A1 | 8/1999 |
| WO | WO 00/03745 A2 | 1/2000 |
| WO | WO 00/35504 A1 | 6/2000 |
| WO | WO 03/053462 A2 | 7/2003 |
| WO | WO 03/085093 A2 | 10/2003 |
| WO | WO 2004/043405 A2 | 5/2004 |
| WO | WO 2004/043407 A2 | 5/2004 |
| WO | WO 2005/103084 A2 | 11/2005 |

OTHER PUBLICATIONS

MacCallum et al (J. Mol. Biol. vol. 262, pp. 732-745, 1996).*
De Pascalis et al (J. Immunology vol. 169, pp. 3076-3084, 2002).*
Genbank Submission; NIH/NCBI, Accession No. BA000018; Kuroda et al.; Oct. 22, 2004 (last submission).
[No Author Listed] ATCC Catalogue website 2001; ATCC No. 35984.
[No Author Listed] ATCC Catalogue: Bacteria and Bacteriophages; 1992; 18th Edition; p. 301.
Ammendolia et al., Slime production and expression of the slime-associated antigen by staphylococcal clinical isolates. J Clin Microbiol. Oct. 1999;37(10):3235-8.
Baldassarri et al., Purification and characterization of the staphylococcal slime-associated antigen and its occurrence among *Staphylococcus epidermis* clinical isolates. Infect Immun. Aug. 1996;64(8):3410-5.
Barsham et al., Detection of antibodies to *Staphylococcus epidermidis* in infected total hip replacements by an enzyme linked immunosorbent assay. J Clin Pathol. Jul. 1985;38(7):839-40.
Bernstein, et al., Antibody coated bacteria in otitis media with effusions. Ann Otol Rhinol Laryngol Suppl. May-Jun. 1980;89(3 Pt 2):104-9. Abstract only.
Capek et al., Chapters 22: Carbohydrates and Chapter 23: Polysaccharides. in Journal of Chromatography Journal Library—vol. 3: Liquid Column Chromatography, A Survey of Modern Technicques and Applications. Deyl et al., eds. Elsevier Scientific Publishing Company: New York, 1975. p. 465-528.
Chanter, Partial purification and characterization of two non K99 mannose-resistant haemagglutinins of *Escherichia coli* B41. J Gen Microbiol. Jan. 1983;129(1):235-43.
Chen et al., Characterization and biological properties of chemically deglycosylated human chorionic gonadotropin. Role of carbohydrate moieties in adenylate cyclase activation. J Biol Chem. Dec. 10, 1982;257(23):14446-52.
Christensen et al., Adherence of slime-producing strains of *Staphylococcus epidermidis* to smooth surfaces. Infect Immun. Jul. 1982;37(1):318-26.
Chu et al., Preparation, characterization, and immunogenicity of conjugates composed of the O-specific polysaccharide of *Shigella dysenteriae* type 1 (Shiga's bacillus) bound to tetanus toxoid. Infect Immun. Dec. 1991;59(12):4450-8.
Conlon et al., icaR encodes a transcriptional repressor involved in environmental regulation of ica operon expression and biofilm formation in *Staphylococcus epidermidis*. J Bacteriol. Aug. 2002; 184(16):4400-8.
Conlon et al., Regulation of icaR gene expression in *Staphylococcus epidermis*. FEMS Microbiol Lett. Nov. 5, 2002;216(2):171-7.
Cramton et al., The intercellular adhesion (ica) locus is present in *Staphylococcus aureus* and is required for biofilm formation. Infect Immun. Oct. 1999;67(10):5427-33.
Dobrin, et al., The role of complement, immunoglobulin and bacterial antigen in coagulase-negative staphylococcal shunt nephritis. Am J Med. Nov. 1975;59(5):660-73. Abstract only.
Elder et al., Characterization of monoclonal antibodies specific for adhesion: isolation of an adhesin of *Streptococcus sanguis* FW213. Infect Immun. Nov. 1986;54(2):421-7.

Espersen, et al., Solid-phase radioimmunoassay for IgG antibodies to *Staphylococcus epidermidis*. Use in serious coagulase-negative staphylococcal infections. Arch Intern Med. Apr. 1987;147(4):689-93. Abstract only.
Espersen, et al., Enzyme-linked immunosorbent assay for detection of *Staphylococcus epidermidis* antibody in experimental *S. epidermidis* endocarditis. J Clin Microbiol. Feb. 1986;23(2):339-42.
Fattom et al., Synthesis and immunologic properties in mice of vaccines composed of *Staphylococcus aureus* type 5 and type 8 capsular polysaccharides conjugated to *Pseudomonas aeruginosa* exotoxin A. Infect Immun. Jul. 1990;58(7):2367-74.
Fattom et al., Effect of conjugation methodology, carrier protein, and adjuvants on the immune response to *Staphylococcus aureus* capsular polysaccharides. Vaccine. Oct. 1995;13(14):1288-93.
Ferreiros et al., Purification and partial characterization of a K99-antigen associated adhesin in *Escherichia coli* (637 strain). Rev Esp Fisiol. Mar. 1983;39(1):45-50.
Fournier et al., Purification and characterization of *Staphylococcus aureus* type 8 capsular polysaccharide. Infect Immun. Jul. 1984;45(1):87-93.
Gerke et al., Characterization of the N-acetylglucosaminyltransferase activity involved in the biosynthesis of the *Staphylococcus epidermidis* polysaccharide intercellular adhesin. J Biol Chem. Jul. 17, 1998;273(29):18586-93.
Gray et al., Effect of extracellular slime substance from *Staphylococcus epidermidis* on the human cellular immune response. Lancet. Feb. 18, 1984;1(8373):365-7.
Heilmann et al., Molecular basis of intercellular adhesion in the biofilm-forming *Staphylococcus epidermidis*. Mol Microbiol. Jun. 1996;20(5):1083-91.
Heilmann et al., Characterization of Tn917 insertion mutants of *Staphylococcus epidermidis* affected in biofilm formation. Infect Immun. Jan. 1996;64(1):277-82.
Hogt et al., Cell surface characteristics of coagulase-negative staphylococci and their adherence to fluorinated poly(ethylenepropylene). Infect Immun. Jan. 1986;51(1):294-301.
Ichiman et al., The relationship of capsular-type of *Staphylococcus epidermidis* to virulence and induction of resistance in the mouse. J Appl Bacteriol. Oct. 1981;51(2):229-41.
Ichiman et al., Induction of resistance with heat-killed unencapsulated strains of *Staphylococcus epidermidis* against challenge with encapsulated strains of *Staphylococcus epidermidis*. Microbiol Immunol. 1989;33(4):277-86.
Ichiman et al., Relation of human serum antibody against *Staphylococcus epidermidis* cell surface polysaccharide detected by enzyme-linked immunosorbent assay to passive protection in the mouse. J Appl Bacteriol. Aug. 1991;71(2):176-81.
Ichiman et al., Specificity of monclonal antibodies against an encapsulated strain of *Staphylococcus epidermids*. in The Staphylococci, Zbl Bakt. 1991;Suppl 21:150-2.
Jefferson et al., Identification of a 5-nucleotide sequence that controls expression of the ica locus in *Staphylococcus aureus* and characterization of the DNA-binding properties of IcaR. Mol Microbiol. May 2003;48(4):889-99.
Jefferson et al., The teicoplanin-associated locus regulator (TcaR) and the intercellular adhesin locus regulator (IcaR) are transcriptional inhibitors of the ica locus in *Staphylococcus aureus*. J Bacteriol. Apr. 2004; 186(8):2449-56.
Johnson et al., Interference with granulocyte function by *Staphylococcus epidermidis* slime. Infect Immun. Oct. 1986;54(1):13-20.
Kelly-Quintos et al., Biological Characterization of Fully Human Monoclonal Antibodies to Staphylococcal Surface Polysaccharide PNAG. Abstracts of the 104th General Meeting of the American Society for Microbiology. Am Soc Microbiol. May 2004;abstract A-63. Abstract and corresponding presentation.
Keutmann et al., Evidence for a conformational change in deglycosylated glycoprotein hormones. FEBS Lett. Jun. 17, 1985;185(2):333-8.
Kohler, Derivation and diversification of monoclonal antibodies. Science. Sep. 19, 1986;233(4770):1281-6.

Kojima et al., Antibody to the capsular polysaccharide/adhesin protects rabbits against catheter-related bacteremia due to coagulase-negative staphylococci. J Infect Dis. Aug. 1990;162(2):435-41.

Kuroda et al., Whole genome sequencing of meticillin-resistant *Staphylococcus aureus*. Lancet. Apr. 21, 2001;357(9264):1225-40.

Lee et al., Chemical characterization and immunogenicity of capsular polysaccharide isolated from mucoid *Staphylococcus aureus*. Infect Immun. Sep. 1987;55(9):2191-7.

Lee et al., Protective efficacy of antibodies to the *Staphylococcus aureus* type 5 capsular polysaccharide in a modified model of endocarditis in rats. Infect Immun. Oct. 1997;65(10):4146-51.

Leith et al., Purification of a *Mycoplasma pneumoniae* adhesin by monoclonal antibody affinity chromatography. J Bacteriol. Feb. 1984;157(2):678-80.

Locksley, Chapter 94: Staphylococcal Infections. in Harrison's Principles of Internal Medicine, Eleventh Edition. Braunwald et al., eds. McGraw-Hill Book Company, Inc.: New York, 1950. p. 537-43.

Ludwicka et al., Investigation on extracellular slime substance produced by *Staphylococcus epidermidis*. Zentralbl Bakteriol Mikrobiol Hyg [A]. Dec. 1984;258(2-3):256-67.

Mack et al., Association of biofihn production of coagulase-negative staphylococci with expression of a specific polysaccharide intercellular adhesin. J Infect Dis. Oct. 1996;174(4):881-4.

Mack et al., Characterization of transposon mutants of biofilm-producing *Staphylococcus epidermidis* impaired in the accumulative phase of biofilm production: genetic identification of a hexosamine-containing polysaccharide intercellular adhesin. Infect Immun. Aug. 1994;62(8):3244-53.

Mack et al., Parallel induction by glucose of adherence and a polysaccharide antigen specific for plastic-adherent *Staphylococcus epidermidis*: evidence for functional relation to intercellular adhesion. Infect Immun. May 1992;60(5):2048-57.

Mack et al., Essential functional role of the polysaccharide intercellular adhesin of *Staphylococcus epidermidis* in hemagglutination. Infect Immun. Feb. 1999;67(2):1004-8.

Mack et al., Identification of three essential regulatory gene loci governing expression of *Staphylococcus epidermidis* polysaccharide intercellular adhesin and biofihn formation. Infect Immun. Jul. 2000;68(7):3799-807.

Mack et al., The intercellular adhesin involved in biofilm accumulation of *Staphylococcus epidermidis* is a linear beta-1,6-linked glucosaminoglycan: purification and structural analysis. J Bacteriol. Jan. 1996;178(1):175-83.

Maira-Litran et al., Immunochemical properties of the staphylococcal poly-N-Acetylglucosamine surface polysaccharide. Infect Immun. Aug. 2002;70(8):4433-40.

Maira-Litran et al., Deacetylated-poly-N-acetyl Glucosamine (dPNAG) Polysaccharide Conjugated to Diphtheria Toxoid (DT) Confers Protection Against Multiple Strains of *Staphylococcus aureus* in a Murine Model of Bacteremia. Abstracts of the 104th General Meeting of the American Society for Microbiology. Am Soc Microbiol. May 2004;abstract D-130. Abstract and corresponding presentation.

Maira-Litran et al., Synthesis and Immunological Properties of a Staphylococcal Deacetylated-poly-N-acetyl Glucosamine (dPNAG) Polysaccharide and Clumping Factor a (ClfA) Protein Conjugate Vaccine. Abstracts of the 104th General Meeting of the American Society for Microbiology. Am Soc Microbiol. May 2004;abstract E-062. Abstract and corresponding presentation.

McKenney et al., The ica locus of *Staphylococcus epidermidis* encodes production of the capsular polysaccharide/adhesin. Infect Immun. Oct. 1998;66(10):4711-20.

McKenney et al., Broadly protective vaccine for *Staphylococcus aureus* based on an in vivo-expressed antigen. Science. May 28, 1999;284(5419):1523-7.

McKenney et al., Vaccine potential of poly-1-6 beta-D-N-succinylglucosamine, an immunoprotective surface polysaccharide of *Staphylococcus aureus* and *Staphylococcus epidermidis*. J Biotechnol. Sep. 29, 2000;83(1-2):37-44.

Melean et al., Toward the automated solid-phase synthesis of oligoglucosamines: systematic evaluation of glycosyl phosphate and glycosyl trichloroacetimidate building blocks. Carbohydr Res. Nov. 19, 2002;337(21-23):1893-916.

Milstein, From antibody structure to immunological diversification of immune response. Science. Mar. 14, 1986;231(4743):1261-8.

Moch et al., Isolation and characterization of the alpha-sialyl-beta-2,3-galactosyl-specific adhesin from fimbriated *Escherichia coli*. Proc Natl Acad Sci U S A. May 1987;84(10):3462-6.

Moreau et al., Structure of the type 5 capsular polysaccharide of *Staphylococcus aureus*. Carbohydr Res. Jul. 1, 1990;201(2):285-97.

Muller et al., Occurrence of capsular polysaccharide/adhesin among clinical isolates of coagulase-negative staphylococci. J Infect Dis. Nov. 1993;168(5):1211-8.

Nagy et al., Multi-adhesin vaccines for the protection of the neonatal piglet against "*E. coli*" infections. Dev Biol Stand. 1983;53:189-97.

Nakano, et al., Polyclonal antibody production in murine spleen cells induced by *Staphylococcus*. Microbiol Immunol. 1980;24(10):981-94. Abstract only.

Ohshima et al., Cell surface antigen of encapsulated *Staphylococcus epidermidis* ATCC 31432. J Clin Microbiol. Jul. 1987;25(7):1338-40.

Ohshima et al., Protection inducing antigen of an encapsulated *Staphylococcus epidermis* SE-10. in The Staphylococci, Zbl Bakt. 1991;Suppl 21:279-80.

Orskov et al., An adhesive protein capsule of *Escherichia coli*. Infect Immun. Jan. 1985;47(1):191-200.

Peters et al., Biology of *S.epidermidis* extracellular slime. in The Staphylococci, Zbl Bakt . 1987;Suppl 16:15-33.

Quie et al., Coagulase-negative staphylococcal adherence and persistence. J Infect Dis. Oct. 1987; 156(4):543-7.

Rogemond et al., Lectinlike adhesins in the *Bacteroides fragilis* group. Infect Immun. Jul. 1986;53(1):99-102.

Rupp et al., Characterization of the importance of polysaccharide intercellular adhesin/hemagglutinin of *Staphylococcus epidermidis* in the pathogenesis of biomaterial-based infection in a mouse foreign body infection model. Infect Immun. May 1999;67(5):2627-32.

Rupp et al., Characterization of *Staphylococcus epidermidis* polysaccharide intercellular adhesin/hemagglutinin in the pathogenesis of intravascular catheter-associated infection in a rat model. Infect Immun. May 1999;67(5):2656-9.

Sanford et al., Detection of staphylococcal membrane receptors on virus-infected cells by direct adhesin overlay. Infect Immun. Jun. 1986;52(3):671-5.

Schumacher-Perdreau et al., Comparative analysis of a biofilm-forming *Staphylococcus epidermidis* strain and its adhesion-positive, accumulation-negative mutant M7. FEMS Microbiol Lett. Mar. 15, 1994;117(1):71-8.

Sompolinsky et al., Encapsulation and capsular types in isolates of *Staphylococcus aureus* from different sources and relationship to phage types. J Clin Microbiol. Nov. 1985;22(5):828-34.

Takeda et al., Protection against endocarditis due to *Staphylococcus epidermidis* by immunization with capsular polysaccharide/adhesin. Circulation. Dec. 1991;84(6):2539-46.

Thomas et al., Enzyme-linked lectinsorbent assay measures N-acetyl-D-glucosamine in matrix of biofilm produced by *Staphylococcus epidermidis*. Curr Microbiol. Oct. 1997;35(4):249-54.

Tojo et al., Isolation and characterization of a capsular polysaccharide adhesin from *Staphylococcus epidermidis*. J Infect Dis. Apr. 1988;157(4):713-22.

Tollersrud et al., Genetic and serologic evaluation of capsule production by bovine mammary isolates of *Staphylococcus aureus* and other *Staphylococcus* spp. from Europe and the United States. J Clin Microbiol. Aug. 2000;38(8):2998-3003.

Vershigora et al., Secretory antibodies to homologous and heterologous staphylococcal strains in the colostrum of rabbits. Zh Mikrobiol Epidemiol Immunobiol. 1980;88-90. Russian.

Vuong et al., A crucial role for exopolysaccharide modification in bacterial biofilm formation, immune evasion, and virulence. J Biol Chem. Dec. 24, 2004;279(52):54881-6. Epub Oct. 22, 2004.

Wang et al., The pgaABCD locus of *Escherichia coli* promotes the synthesis of a polysaccharide adhesin required for biofilm formation. J Bacteriol. May 2004;186(9):2724-34.

Wessels et al., Isolation and characterization of type IV group B *Streptococcus* capsular polysaccharide. Infect Immun. Apr. 1989;57(4):1089-94.

Wray et al., Identification and characterization of a uroepithelial cell adhesin from a uropathogenic isolate of *Proteus mirabilis*. Infect Immun. Oct. 1986;54(1):43-9.

Yamada, et al., Possible common biological and immunological properties for detecting encapsulated strains of *Staphylococcus epidermidis*. J Clin Microbiol. Oct. 1988;26(10):2167-72.

Yoshida et al., Mouse virulent strain of *Staphylococcus epidermidis*. Relation of antiphagocytic activity to the protection-inducing antigen. Jpn J Microbiol. Jun. 1976;20(3):209-17.

Yoshida, et al., Immunological response to a strain of *Staphylococcus epidermidis* in the rabbit: production of protective antibody. J Med Microbiol. Nov. 1978;11(4):371-7. Abstract only.

Yoshida et al., Cross protection between a strain of *Staphylococcus epidermidis* and eight other species of coagulase-negative staphylococci. Can J Microbiol. Jul. 1988;34(7):913-5.

Youmans, Staphylococci, Staphylococcal Disease, and Toxic Shock Syndrome. in The Biologic and Clinical Basis of Infectious Diseases, Third Edition.. Youmans et al., eds. W.B. Saunders Company: Philadelphia, 1985. p. 618-29 and 738-9.

Ziebuhr et al., Detection of the intercellular adhesion gene cluster (ica) and phase variation in *Staphylococcus epidermidis* blood culture strains and mucosal isolates. Infect Immun. Mar. 1997;65(3):890-6.

Ziebuhr et al., A novel mechanism of phase variation of virulence in *Staphylococcus epidermidis*: evidence for control of the polysaccharide intercellular adhesin synthesis by alternating insertion and excision of the insertion sequence element IS256. Mol Microbiol. Apr. 1999;32(2):345-56.

Götz, *Staphylococcus* and biofilms. Mol Microbiol. Mar. 2002;43(6):1367-78.

Gerke et al., Experimental *Pseudomonas aeruginosa* infection of the mouse cornea. Infection and Immunity. 1971;3(2):209-16.

Maira-Litran et al., Comparative opsonic and protective activities of *Staphylococcus aureus* conjugate vaccines containing native or deacetylated Staphylococcal Poly-N-acetyl-beta-(1-6)-glucosamine. Infect Immun. Oct. 2005;73(10):6752-62. Abstract Only.

Pier et al., Isolation and characterization of a high-molecular-weight polysaccharide from the slime of *Pseudomonas aeruginosa*. Infect Immun. Dec. 1978;22(3):908-18.

Pier et al., Protective immunity induced in mice by immunization with high-molecular-weight polysaccharide from *Pseudomonas aeruginosa*. Infect Immun. Dec. 1978;22(3):919-25.

Pier et al., Further purification and characterization of high-molecular-weight polysaccharide from *Pseudomonas aeruginosa*. Infect Immun. Dec. 1983;42(3):936-41.

Maira-Litran et al., Biologic properties and vaccine potential of the staphylococcal poly-N-acetyl glucosamine surface polysaccharide. Vaccine. Feb. 17, 2004;22(7):872-9.

Allignet et al., Tracking adhesion factors in *Staphylococcus caprae* strains responsible for human bone infections following implantation of orthopaedic material. Microbiology. Aug. 1999;145 ( Pt 8):2033-42.

Arciola et al., In catheter infections by *Staphylococcus epidermidis* the intercellular adhesion (ica) locus is a molecular marker of the virulent slime-producing strains. J Biomed Mater Res. Mar. 5, 2002;59(3):557-62. Abstract Only.

Bhasin et al., Identification of a gene essential for O-acetylation of the *Staphylococcus aureus* type 5 capsular polysaccharide. Mol Microbiol. Jan. 1998;27(1):9-21. Abstract Only.

Cramton et al., Anaerobic conditions induce expression of polysaccharide intercellular adhesin in *Staphylococcus aureus* and *Staphylococcus epidermidis*. Infect Immun. Jun. 2001;69(6):4079-85.

Dobinsky et al., Influence of Tn917 insertion on transcription of the icaADBC operon in six biofilm-negative transposon mutants of *Staphylococcus epidermidis*. Plasmid. Jan. 2002;47(1):10-7. Abstract Only.

Fattom et al., Antigenic determinants of *Staphylococcus aureus* type 5 and type 8 capsular polysaccharide vaccines. Infect Immun. Oct. 1998;66(10):4588-92.

Fey et al., Characterization of the relationship between polysaccharide intercellular adhesin and hemagglutination in *Staphylococcus epidermidis*. J Infect Dis. Jun. 1999;179(6):1561-4. Abstract Only.

Fowler et al., The intercellular adhesin locus ica is present in clinical isolates of *Staphylococcus aureus* from bacteremic patients with infected and uninfected prosthetic joints. Med Microbiol Immunol (Berl). Apr. 2001;189(3):127-31. Abstract Only.

Frebourg et al., PCR-Based assay for discrimination between invasive and contaminating *Staphylococcus epidermidis* strains. J Clin Microbiol. Feb. 2000;38(2):877-80.

Gelosia et al., Phenotypic and genotypic markers of *Staphylococcus epidermidis* virulence. Clin Microbiol Infect. Apr. 2001;7(4):193-9. Abstract Only.

Heilmann et al., Further characterization of *Staphylococcus epidermidis* transposon mutants deficient in primary attachment or intercellular adhesion. Zentralbl Bakteriol. Jan. 1998;287(1-2):69-83. Abstract Only.

Ji et al., Regulated antisense RNA eliminates alpha-toxin virulence in *Staphylococcus aureus* infection. J Bacteriol. Nov. 1999;181(21):6585-90.

Ji et al., Identification of critical staphylococcal genes using conditional phenotypes generated by antisense RNA. Science. Sep. 21, 2001;293(5538):2266-9.

Kolberg et al., Monoclonal antibodies with specificities for *Streptococcus pneumoniae* group 9 capsular polysaccharides. FEMS Immunol Med Microbiol. Apr. 1998;20(4):249-55. Abstract Only.

Longworth et al., O-Acetylation status of the capsular polysaccharides of serogroup Y and W135 meningococci isolated in the UK. FEMS Immunol Med Microbiol. Jan. 14, 2002;32(2):11923. Abstract Only.

Mack et al., Molecular mechanisms of *Staphylococcus epidermidis* biofilm formation. J Hosp Infect. Dec. 1999;43 Suppl:S113-25. Abstract Only.

Mack et al., Genetic and biochemical analysis of *Staphylococcus epidermidis* biofilm accumulation. Methods Enzymol. 2001;336:215-39.

McNeely et al., Antibody responses to capsular polysaccharide backbone and O-acetate side groups of *Streptococcus pneumoniae* type 9V in humans and rhesus macaques. Infect Immun. Aug. 1998;66(8):3705-10.

Michon et al., Structure activity studies on group C meningococcal polysaccharide-protein conjugate vaccines: effect of O-acetylation on the nature of the protective epitope. Dev Biol (Basel). 2000;103:151-60. Abstract Only.

Muller et al., Capsular polysaccharide/adhesin (PS/A) production by coagulase-negative staphylococci (CNS) is associated with adherence to silastic tubing. 1989. p. 49. Abstract B-111.

GenBank Submission; NIH/NCBI; Accession No. DQ231549; Kelly-Quintos et al.; Printed May 9, 2006.

GenBank Submission; NIH/NCBI; Accession No. DQ231550; Kelly-Quintos et al.; Printed May 9, 2006.

GenBank Submission; NIH/NCBI; Accession No. DQ231551; Kelly-Quintos et al.; Printed May 9, 2006.

GenBank Submission; NIH/NCBI; Accession No. DQ231552; Kelly-Quintos et al.; Printed May 9, 2006.

GenBank Submission; NIH/NCBI; Accession No. DQ231553; Kelly-Quintos et al.; Printed May 9, 2006.

GenBank Submission; NIH/NCBI; Accession No. DQ231554; Kelly-Quintos et al.; Printed May 9, 2006.

Kelly-Quintos et al., Characterization of the opsonic and protective activity against *Staphylococcus aureus* of fully human monoclonal antibodies specific for the bacterial surface polysaccharide poly-N-acetylglucosamine. Infect Immun. May 2006;74(5):2742-50.

Pollack et al., Functional properties of isotype-switched immunoglobulin M (IgM) and IgG monoclonal antibodies to *Pseudomonas aeruginosa* lipopolysaccharide. Infect Immun. Nov. 1995;63(11):4481-8.

Preston et al., Prophylactic and therapeutic efficacy of immunoglobulin G antibodies to *Pseudomonas aeruginosa* lipopolysaccharide against murine experimental corneal infection. Invest Ophthalmol Vis Sci. Jun. 1997;38(7):1418-25. Abstract Only.

Preston et al., Production and characterization of a set of mouse-human chimeric immunoglobulin G (IgG) subclass and IgA monoclonal antibodies with identical variable regions specific for *Pseudomonas aeruginosa* serogroup O6 lipopolysaccharide. Infect Immun. Sep. 1998;66(9):4137-42.

Joyce et al., Isolation, structural characterization, and immunological evaluation of a high-molecular-weight exopolysaccharide from *Staphylococcus aureus*. Carbohydr Res. Apr. 22, 2003;338(9):903-22.

Kossaczka et al., Synthesis and immunological properties of Vi and di-O-acetyl pectin protein conjugates with adipic acid dihydrazide as the linker. Infect Immun. Jun. 1997;65(6):2088-93.

Ohshima et al., Immunochemical characterization and biological properties of a cell surface antigen extracted from encapsulated *Staphylococcus epidermidis* strain SE-10. Zentralbl Bakteriol. Dec. 1990;274(3):417-25.

* cited by examiner

Fig. 1 Monoclonal Antibodies (IgG2) binding to native PNAG

Fig. 2 Monoclonal Antibodies(IgG2) binding to dPNAG

Fig. 3 PNAG competition ELISA with IgG2 Monoclonal Antibodies

Fig. 4 Monoclonal Antibodies (IgG1) binding to native PNAG

Fig. 5 Monoclonal Antibodies (IgG1) binding to dPNAG

FIG. 9

POLY-N-ACETYL GLUCOSAMINE (PNAG/DPNAG)-BINDING PEPTIDES AND METHODS OF USE THEREOF

RELATED APPLICATIONS

This application claims priority to U.S. Provisional Application Ser. No. 60/564,105, filed Apr. 21, 2004, the entire contents of which are incorporated by reference herein.

GOVERNMENT SUPPORT

This work was funded in part by grant number AI46706, from the National Institutes of Health. Accordingly, the United States Government may have certain rights to this invention.

FIELD OF THE INVENTION

This invention relates generally to peptides that bind to poly-N-acetyl glucosamine (PNAG) and deacetylated PNAG (dPNAG) of bacteria such as *Staphylococcus*, and their use in the diagnosis and treatment of Staphylococcal and other PNAG-expressing bacterial infections.

BACKGROUND OF THE INVENTION

Staphylococci are gram-positive bacteria which normally inhabit and colonize the skin and mucus membranes of humans. If the skin or mucus membrane becomes damaged during surgery or other trauma, the Staphylococci may gain access to internal tissues causing infection to develop. If the Staphylococci proliferate locally or enter the lymphatic or blood system, serious infectious complications such as those associated with Staphylococcal bacteremia may result. Complications associated with Staphylococcal bacteremia include septic shock, endocarditis, arthritis, osteomyelitis, pneumonia, and abscesses in various organs.

Staphylococci include both coagulase positive organisms that produce a free coagulase and coagulase negative organisms that do not produce this free coagulase. *Staphylococcus aureus* is the most common coagulase-positive form of Staphylococci. *S. aureus* generally causes infection at a local site, either extravascular or intravascular, which ultimately may result in bacteremia *S. aureus* is also a leading cause of acute osteomyelitis and causes Staphylococcal pneumonia infections. Additionally, *S. aureus* is responsible for approximately 1-9% of the cases of bacterial meningitis and 10-15% of brain abscesses.

There are at least twenty-one known species of coagulase-negative Staphylococci, including *S. epidermidis, S. saprophyticus, S. hominis, S. warneri, S. haemolyticus, S. saprophiticus, S. cohnii, S. xylosus, S. simulans*, and *S. capitis*. *S. epidermidis* is the most frequent infection-causing agent associated with intravenous access devices and the most frequent isolate in primary nosocomial bacteremias. *S. epidermidis* is also associated with prosthetic valve endocarditis.

*Staphylococcus* is also a common source of bacterial infections in animals. For instance, Staphylococcal mastitis is a common problem in ruminants including cattle, sheep, and goats. The disease is generally treated with antibiotics to reduce the infection but the treatment is a costly procedure and still results in a loss of milk production. The most effective vaccines for livestock identified to date are live, intact *S. aureus* vaccines administered subcutaneously. The administration of live vaccines, however, is associated with the risk of infection and with toxic reactions. For that reason, many researchers have attempted to produce killed *S. aureus* vaccines and/or to isolate capsular polysaccharides or cell wall components which will induce immunity to *S. aureus*. None of these attempts, however, has been successful.

SUMMARY OF THE INVENTION

The present invention relates generally to the identification and use of peptides that bind to poly-N-acetyl glucosamine (PNAG) such as Staphylococcal poly-N-acetyl glucosamine (PNAG), and poorly acetylated or deacetylated PNAG (collectively referred to herein as dPNAG). These peptides are referred to herein as PNAG/dPNAG-binding peptides. Examples of such peptides include those having amino acid sequences derived from complementarity determining regions (CDRs) or variable regions of antibodies described herein or produced from hybridomas deposited with the American Type Culture Collection (ATCC), located at 10801 University Blvd. Manassas, Va. 20110-2209 ATCC on Apr. 21, 2004, under Accession Nos. PTA-5931 (F598), PTA-5932 (F628) and PTA-5933 (F630). These peptides include but are not limited to polypeptides, monoclonal antibodies (such as human monoclonal antibodies) and antibody fragments. A common feature of the peptides disclosed herein is their ability to recognize and bind to Staphylococcal PNAG and/or dPNAG specifically. PNAG and/or dPNAG expressed by other bacterial strains may also be recognized and bound by the peptides of the invention. An important characteristic of some of the antibodies and antibody fragments provided by the invention is their ability to enhance opsonization and phagocytosis (i.e., opsonophagocytosis) of bacterial strains, such as Staphylococcal species, that express PNAG.

Thus, in one aspect, the invention provides a composition comprising an isolated peptide that selectively binds to Staphylococcal poly-N-acetyl glucosamine (PNAG/dPNAG) and comprises an amino acid sequence of a Staphylococcal PNAG/dPNAG-binding CDR, or functionally equivalent variant thereof.

Various embodiments are shared between this and other aspects of the invention. These embodiments will be recited once but it is to be understood that they apply equally to all aspects of the invention.

In one embodiment, the Staphylococcal PNAG/dPNAG-binding CDR is a Staphylococcal PNAG/dPNAG-binding CDR3. The Staphylococcal PNAG/dPNAG-binding CDR3 may comprise an amino acid sequence of a heavy chain CDR3 selected from the group consisting of SEQ ID NO: 9, SEQ ID NO:15 and SEQ ID NO:21 or it may comprise an amino acid sequence of a heavy chain CDR3 derived from a deposited hybridoma having ATCC Accession No. PTA-5931, PTA-5932 or PTA-5933. The Staphylococcal PNAG/dPNAG-binding CDR3 may comprise an amino acid sequence of a light chain CDR3 selected from the group consisting of SEQ ID NO:12, SEQ ID NO:18, and SEQ ID NO: 24 or it may comprise an amino acid sequence of a light chain CDR3 derived from a deposited hybridoma having ATCC Accession No. PTA-5931, PTA-5932 or PTA-5933.

In another embodiment, the Staphylococcal PNAG/dPNAG-binding CDR is a Staphylococcal PNAG/dPNAG-binding CDR2. The Staphylococcal PNAG/dPNAG-binding CDR2 may comprise an amino acid sequence selected from the group consisting of SEQ ID NO:8, SEQ ID NO:11, SEQ ID NO:14, SEQ ID NO:17, SEQ ID NO:20 and SEQ ID NO:23 or it may comprise an amino acid sequence of a CDR2 derived from a deposited hybridoma having ATCC Accession No. PTA-5931, PTA-5932 or PTA-5933.

In another embodiment, the Staphylococcal PNAG/dPNAG-binding CDR is a Staphylococcal PNAG/dPNAG-binding CDR1. The Staphylococcal PNAG/dPNAG-binding CDR1 may comprise an amino acid sequence selected from the group consisting of SEQ ID NO:7, SEQ ID NO:10, SEQ ID NO:13, SEQ ID NO:16, SEQ ID NO:19 and SEQ ID NO:22 or it may comprise an amino acid sequence of a CDR1 derived from a deposited hybridoma having ATCC Accession No. PTA-5931, PTA-5932 or PTA-5933.

In one embodiment, the isolated peptide comprises an amino acid sequence selected from the group consisting of SEQ ID NO:1, SEQ ID NO:3 and SEQ ID NO:5 or an amino acid sequence of a heavy chain variable region derived from a deposited hybridoma having ATCC Accession No. PTA-5931, PTA-5932 or PTA-5933.

In another embodiment, the isolated peptide comprises an amino acid sequence selected from the group consisting of SEQ ID NO:2, SEQ ID NO:4 and SEQ ID NO:6 or an amino acid sequence of a light chain variable region derived from a deposited hybridoma having ATCC Accession No. PTA-5931, PTA-5932 or PTA-5933.

In one embodiment, the isolated peptide is an isolated antibody or antibody fragment, such as but not limited to an isolated intact, preferably soluble, monoclonal antibody or an isolated monoclonal antibody fragment such as but not limited to an F(ab')$_2$ fragment an Fd fragment and an Fab fragment. The isolated antibody may be an antibody produced from a deposited hybridoma having ATCC Accession No. PTA-5931, PTA-5932 or PTA-5933, or an antibody fragment thereof.

In one embodiment, the isolated antibody or antibody fragment enhances opsonophagocytosis of PNAG-expressing bacterial strains (e.g., Staphylococci such as but not limited to *S. aureus* or *S. epidermidis*).

In one embodiment, the isolated antibody or antibody fragment comprises an amino acid sequence comprising a heavy chain variable region and selected from the group consisting of SEQ ID NO:1, SEQ ID NO:3 and SEQ ID NO:5, and an amino acid sequence comprising a light chain variable region and selected from the group consisting of SEQ ID NO:2, SEQ ID NO:4 and SEQ ID NO:6. In another embodiment, the isolated antibody or antibody fragment comprises an amino acid sequence comprising a heavy chain variable region derived from a deposited hybridoma having ATCC Accession No. PTA-5931, PTA-5932 or PTA-5933, and an amino acid sequence comprising light chain variable region derived from a deposited hybridoma having ATCC Accession No. PTA-5931, PTA-5932 or PTA-5933.

The isolated antibody or antibody fragment may comprise an amino acid sequence of SEQ ID NO:1 and an amino acid sequence of SEQ ID NO:2, or an amino acid sequence of SEQ ID NO:3 and an amino acid sequence of SEQ ID NO:4, or an amino acid sequence of SEQ ID NO:5 and an amino acid sequence of SEQ ID NO:6.

The isolated antibody or antibody fragment may comprise an amino acid sequence of a heavy chain variable region derived from deposited hybridoma having Accession No. PTA-5931 (F598) and an amino acid sequence comprising light chain variable region derived from deposited hybridoma having Accession No. PTA-5931 (F598), or an amino acid sequence of a heavy chain variable region derived from deposited hybridoma having Accession No. PTA-5932 (F628) and an amino acid sequence comprising light chain variable region derived from deposited hybridoma having Accession No. PTA-5932 (F628), or an amino acid sequence of a heavy chain variable region derived from deposited hybridoma having Accession No. PTA-5933 (F630) and an amino acid sequence comprising light chain variable region derived from deposited hybridoma having Accession No. PTA-5933 (F630).

In one embodiment, the isolated peptide is conjugated to a detectable label. The detectable label may be an in vivo or an in vitro detectable label.

In one embodiment, the composition further comprises a pharmaceutically acceptable carrier. In other embodiments, the isolated peptide such as the isolated antibody or antibody fragment is present in an effective amount for inhibiting an infection by a bacterial strain expressing PNAG (such as a Staphylococcal infection) or in an effective amount for detecting a bacterial strain expressing PNAG (such as Staphylococci) in a sample in or from a subject.

In one embodiment, the isolated peptide selectively binds to Staphylococcal PNAG. In another embodiment, the isolated peptide selectively binds to Staphylococcal dPNAG.

In yet another aspect, the invention provides an isolated nucleic acid molecule comprising a nucleotide sequence encoding a Staphylococcal PNAG/dPNAG-binding CDR.

In one embodiment, the nucleotide sequence is selected from the group consisting of SEQ ID NO:9, SEQ ID NO:12, SEQ ID NO:15, SEQ ID NO:18, SEQ ID NO:21 and SEQ ID NO:24. In another embodiment, the nucleotide sequence is selected from the group consisting of SEQ ID NO:1, SEQ ID NO:2, SEQ ID NO:3, SEQ ID NO:4, SEQ ID NO:5 and SEQ ID NO:6.

In one embodiment, the nucleic acid is a heavy chain variable region nucleic acid molecule derived from a hybridoma having Accession No. PTA-5931, PTA-5932 or PTA-5933. In another embodiment, the nucleic acid is a light chain variable region nucleic acid molecule derived from a hybridoma having Accession No. PTA-5931, PTA-5932 or PTA-5933. In yet another embodiment, the nucleic acid is a heavy chain CDR nucleic acid molecule derived from a hybridoma having Accession No. PTA-5931, PTA-5932 or PTA-5933 or it is a light chain CDR nucleic acid molecule derived from a hybridoma having Accession No. PTA-5931, PTA-5932 or PTA-5933.

The invention further provides, in other aspects, expression vectors comprising the afore-mentioned isolated nucleic acid molecules, operably linked to a promoter and cells transformed or transfected with such expression vectors.

In other aspects, the invention provides an isolated cell producing an anti-Staphylococcal PNAG/dPNAG monoclonal antibody (F598) and having ATCC Accession No. PTA-5931, an isolated cell producing an anti-Staphylococcal PNAG/dPNAG monoclonal antibody (F628) and having ATCC Accession No. PTA-5932, and an isolated cell producing an anti-Staphylococcal PNAG/dPNAG monoclonal antibody (F630) and having ATCC Accession No. PTA-5933. The invention further provides, in additional aspects, the isolated monoclonal antibody produced by the afore-mentioned deposited isolated cells, or antibody fragments thereof. The antibody fragment may be but it not limited to an F(ab')$_2$ fragment, an Fd fragment or an Fab fragment. In a related embodiment, the fragment enhances opsonophagocytosis of PNAG-expressing bacterial strains (e.g., Staphylococci such as but not limited to *S. aureus* or *S. epidermidis*).

In another aspect, the invention provides a method for detecting bacterial strains expressing PNAG (such as Staphylococci) in a subject or a sample from a subject. The method comprises determining a test level of binding of an isolated peptide or a functionally equivalent variant thereof to a sample in or from a subject, and comparing the test level of binding to a control, wherein the isolated peptide selectively binds to Staphylococcal PNAG/dPNAG and comprises a Staphylococcal PNAG/dPNAG-binding CDR, or a functionally equivalent variant thereof, and wherein a test level of binding that is greater than the control is indicative of the presence of the bacterial strain (e.g., Staphylococci) in the sample. The bacteria to be detected may be Staphylococci, *E. coli*, *Yersinia pestis* (*Y. pestis*), *Y. entercolitica*, *Xanthomonas axonopodis* (*X. axonopodis*), *Pseudomonas fluorescens* (*P. fluorescens*), *Actinobacillus actinomycetemcomitans* (*A. actinomycetemcomitans*), *A. pleuropneumoniae*, *Bordetella pertussis* (*B. pertussis*), *B. parapertussis* or *B. bronchiseptica*. The invention also provides methods for detecting and treating plant infections by bacteria expressing PNAG such as *Ralstonia solanacearum* (*R. solanacearum*).

In one embodiment, the test level of binding is measured in vitro.

In another aspect, the invention provides a method for treating a subject having, or at risk of developing, an infection by a bacterial strain expressing PNAG (e.g., a Staphylococcal infection). The method comprises administering to a subject in need of such treatment an isolated peptide that selectively binds to Staphylococcal PNAG/dPNAG, and comprises a Staphylococcal PNAG/dPNAG-binding CDR or a functionally equivalent variant thereof, in an amount effective to inhibit the infection. In another embodiment, the isolated peptide is conjugated to a cytotoxic agent.

In one embodiment, the subject has or is at risk of developing a Staphylococcal infection, such as but not limited to *S. aureus* or *S. epidermidis* infection. In another embodiment, the subject has or is at risk of developing an *E. coli*, *Yersinia pestis* (*Y. pestis*), *Y. entercolitica*, *Xanthomonas axonopodis* (*X. axonopodis*), *Pseudomonas fluorescens* (*P. fluorescens*), *Actinobacillus actinomycetemcomitans* (*A. actinomycetemcomitans*), *A. pleuropneumoniae*, *Bordetella pertussis* (*B. pertussis*), *B. parapertussis* or *B. bronchiseptica* infection.

The foregoing bacterial infections underlie conditions such as gastroenteritis, urinary-tract infections, plague, whopping cough, bloodstream infections and dental infections (periodontitis). The invention intends to treat these latter conditions by treating underlying the bacterial infection. The detection and treatment methods provided herein are suitable for human and non-human subjects that have or are at risk of developing such infections. Non-human subjects include agricultural animals such as cows and pigs, but are not so limited.

*Ralstonia solanacearum* (*R. solanacearum*) is another PNAG expressing bacteria, however it is considered a plant rather than an animal pathogen. The invention contemplates detection and treatment of plant species having such infections using the binding peptides provided herein, preferably conjugated to a detectable or cytotoxic label, depending on the method.

In yet another aspect, the invention provides a method for treating an infection by a bacterial strain that expresses PNAG (e.g., Staphylococcal infection) comprising administering to a subject in need thereof a PNAG/dPNAG-binding peptide that reduces bacterial load in a subject by at least 50% in at least 4 hours after exposure to a bacterium that expresses PNAG in an amount effective to treat the infection.

In one embodiment, the PNAG/dPNAG-binding peptide is an isolated antibody or antibody fragment. In one embodiment, the infection is a Staphylococcal infection. In one embodiment, the Staphylococcal infection is an *S. aureus* infection or an *S. epidermidis* infection. In another embodiment, the infection is an *E. coli*, *Yersinia pestis* (*Y. pestis*), *Y. entercolitica*, *Xanthomonas axonopodis* (*X. axonopodis*), *Pseudomonas fluorescens* (*P. fluorescens*), *Actinobacillus actinomycetemcomitans* (*A. actinomycetemcomitans*), *A. pleuropneumoniae*, *Bordetella pertussis* (*B. pertussis*), *B. parapertussis* or *B. bronchiseptica* infection. *Ralstonia solanacearum* (*R. solanacearum*) infections are also contemplated by the invention, although these affect plants rather than animals. In another embodiment, the PNAG/dPNAG-binding peptide is administered prior to exposure to the bacterium, such as but not limited to at least 24 hours prior to exposure to the bacterium.

In one embodiment, the PNAG/dPNAG-binding peptide reduces bacterial load in a subject by at least 60% in at least 4 hours after exposure to the bacterium. In another embodiment, the PNAG/dPNAG-binding peptide reduces bacterial load in a subject by at least 50% in 2 hours after exposure to the bacterium. In yet another embodiment, the PNAG/dPNAG-binding peptide reduces bacterial load in a subject by at least 60% in 2 hours after exposure to the bacterium. Bacteria that express PNAG include but are not limited to Staphylococci, *E. coli*, *Yersinia pestis* (*Y. pestis*), *Y. entercolitica*, *Xanthomonas axonopodis* (*X. axonopodis*), *Pseudomonas fluorescens* (*P. fluorescens*), *Actinobacillus actinomycetemcomitans* (*A. actinomycetemcomitans*), *A. pleuropneumoniae*, *Bordetella pertussis* (*B. pertussis*), *B. parapertussis* and *B. bronchiseptica*, which affect animals, and *Ralstonia solanacearum* (*R. solanacearum*) which affects plants.

These and other embodiments of the invention will be described in greater detail herein.

BRIEF DESCRIPTION OF THE FIGURES

Figure 9:
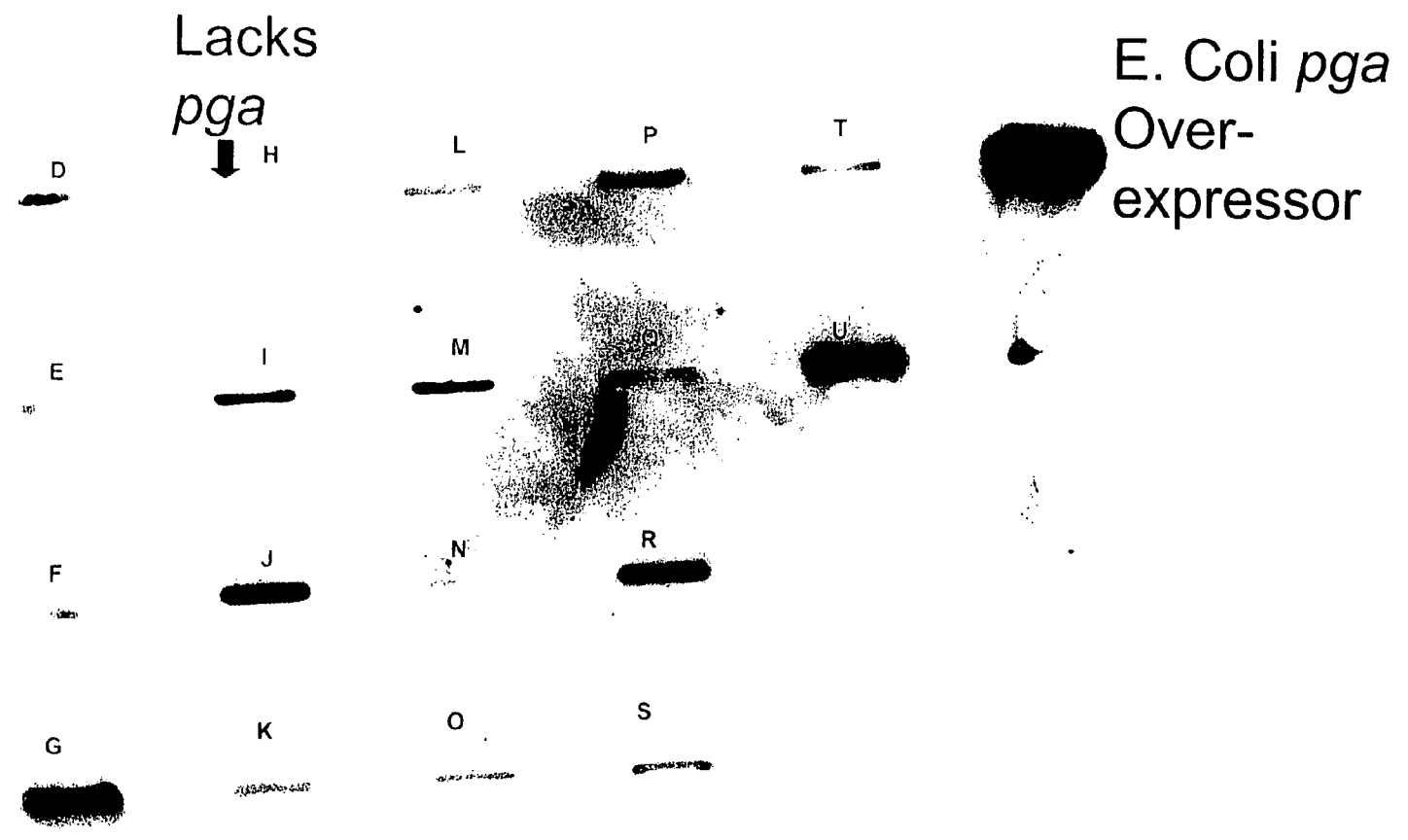

FIG. 9 is an immunoblot showing PNAG expression by *E. coli* UTI strains labeled D-U and including an *E. coli* pga over-expressing isolate (top right hand corner).

Figure 1:
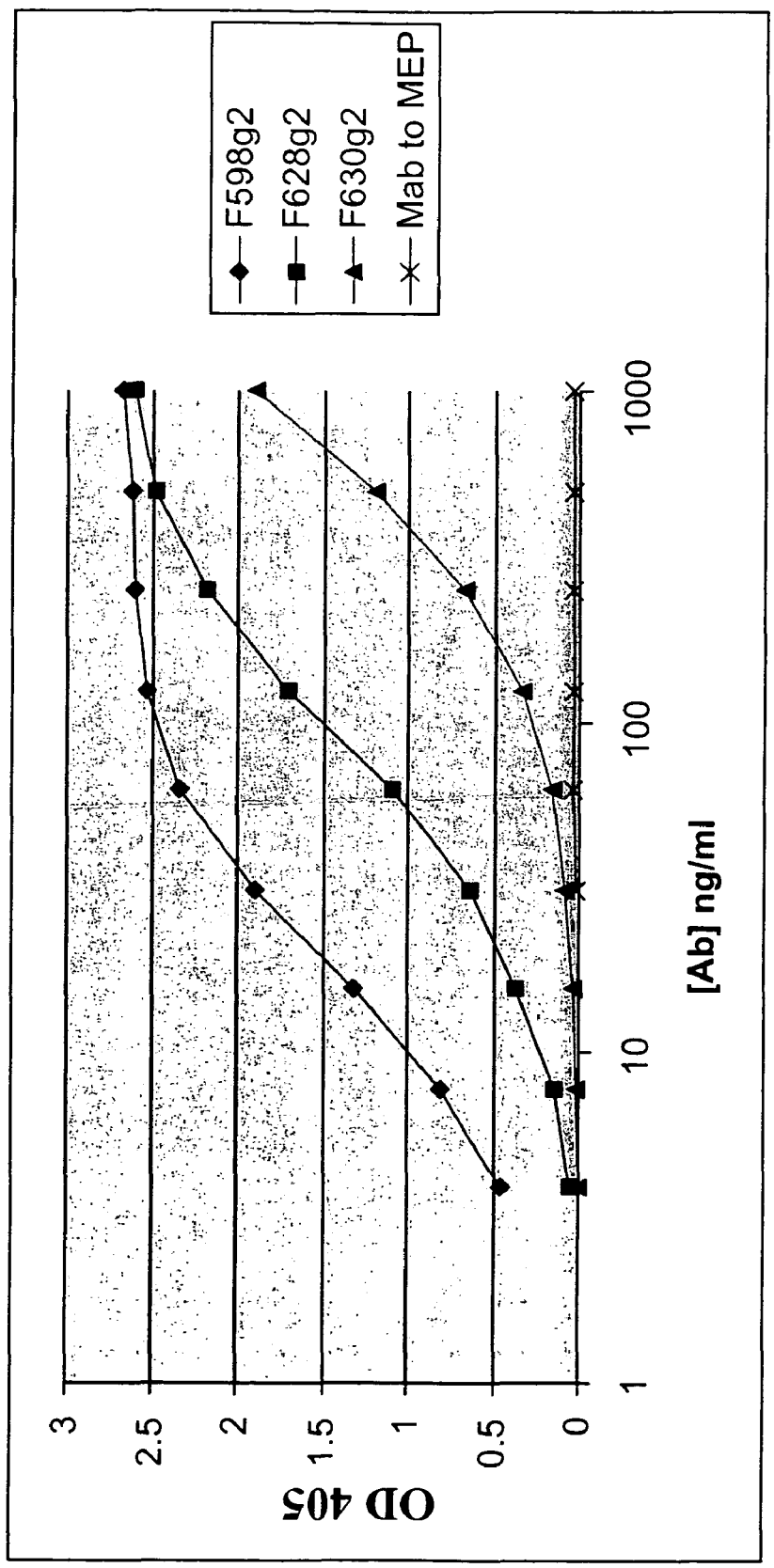
FIG. 1 is a graph showing the binding affinities of monoclonal antibodies (MAbs) F598, F628 and F630 (in an IgG2 form) to native PNAG. MAb to *P. aeruginosa* MEP is used as a negative control.

It is to be understood that the Figures are not required for enablement of the invention.

BRIEF DESCRIPTION OF THE SEQUENCE LISTING

SEQ ID NO: 1 is the amino acid sequence of antibody F598 heavy chain variable region.

SEQ ID NO: 2 is the amino acid sequence of antibody F598 light chain variable region.

SEQ ID NO: 3 is the amino acid sequence of antibody F628 heavy chain variable region.

SEQ ID NO: 4 is the amino acid sequence of antibody F628 light chain variable region.

SEQ ID NO: 5 is the amino acid sequence of antibody F630 heavy chain variable region.

SEQ ID NO: 6 is the amino acid sequence of antibody F630 light chain variable region.

SEQ ID NO: 7 is the amino acid sequence of CDR1 of antibody F598 heavy chain.

SEQ ID NO: 8 is the amino acid sequence of CDR2 of antibody F598 heavy chain.

SEQ ID NO: 9 is the amino acid sequence of CDR3 of antibody F598 heavy chain.

SEQ ID NO: 10 is the amino acid sequence of CDR1 of antibody F598 light chain.

SEQ ID NO: 11 is the amino acid sequence of CDR2 of antibody F598 light chain.

SEQ ID NO: 12 is the amino acid sequence of CDR3 of antibody F598 light chain.

SEQ ID NO: 13 is the amino acid sequence of CDR1 of antibody F628 heavy chain.

SEQ ID NO: 14 is the amino acid sequence of CDR2 of antibody F628 heavy chain.

SEQ ID NO: 15 is the amino acid sequence of CDR3 of antibody F628 heavy chain.

SEQ ID NO: 16 is the amino acid sequence of CDR1 of antibody F628 light chain.

SEQ ID NO: 17 is the amino acid sequence of CDR2 of antibody F628 light chain.

SEQ ID NO: 18 is the amino acid sequence of CDR3 of antibody F628 light chain.

SEQ ID NO: 19 is the amino acid sequence of CDR1 of antibody F630 heavy chain.

SEQ ID NO: 20 is the amino acid sequence of CDR2 of antibody F630 heavy chain.

SEQ ID NO: 21 is the amino acid sequence of CDR3 of antibody F630 heavy chain.

SEQ ID NO: 22 is the amino acid sequence of CDR1 of antibody F630 light chain.

SEQ ID NO: 23 is the amino acid sequence of CDR2 of antibody F630 light chain.

SEQ ID NO: 24 is the amino acid sequence of CDR3 of antibody F630 light chain.

SEQ ID NO: 25 is the nucleotide sequence of antibody F598 heavy chain variable region.

SEQ ID NO: 26 is the nucleotide sequence of antibody F598 light chain variable region.

SEQ ID NO: 27 is the nucleotide sequence of antibody F628 heavy chain variable region.

SEQ ID NO: 28 is the nucleotide sequence of antibody F628 light chain variable region.

SEQ ID NO: 29 is the nucleotide sequence of antibody F630 heavy chain variable region.

SEQ ID NO: 30 is the nucleotide sequence of antibody F630 light chain variable region.

SEQ ID NO: 31 is the nucleotide sequence of CDR1 of antibody F598 heavy chain.

SEQ ID NO: 32 is the nucleotide sequence of CDR2 of antibody F598 heavy chain.

SEQ ID NO: 33 is the nucleotide sequence of CDR3 of antibody F598 heavy chain.

SEQ ID NO: 34 is the nucleotide sequence of CDR1 of antibody F598 light chain.

SEQ ID NO: 35 is the nucleotide sequence of CDR2 of antibody F598 light chain.

SEQ ID NO: 36 is the nucleotide sequence of CDR3 of antibody F598 light chain.

SEQ ID NO: 37 is the nucleotide sequence of CDR1 of antibody F628 heavy chain.

SEQ ID NO: 38 is the nucleotide sequence of CDR2 of antibody F628 heavy chain.

SEQ ID NO: 39 is the nucleotide sequence of CDR3 of antibody F628 heavy chain.

SEQ ID NO: 40 is the nucleotide sequence of CDR1 of antibody F628 light chain.

SEQ ID NO: 41 is the nucleotide sequence of CDR2 of antibody F628 light chain.

SEQ ID NO: 42 is the nucleotide sequence of CDR3 of antibody F628 light chain.

SEQ ID NO: 43 is the nucleotide sequence of CDR1 of antibody F630 heavy chain.

SEQ ID NO: 44 is the nucleotide sequence of CDR2 of antibody F630 heavy chain.

SEQ ID NO: 45 is the nucleotide sequence of CDR3 of antibody F630 heavy chain.

SEQ ID NO: 46 is the nucleotide sequence of CDR1 of antibody F630 light chain.

SEQ ID NO: 47 is the nucleotide sequence of CDR2 of antibody F630 light chain.

SEQ ID NO: 48 is the nucleotide sequence of CDR3 of antibody F630 light chain.

SEQ ID NO: 49 is the nucleotide sequence of primer lambda constant.

SEQ ID NO: 50 is the nucleotide sequence of primer Hu lambda sig 5.

SEQ ID NO: 51 is the nucleotide sequence of primer Heavy chain constant.

SEQ ID NO: 52 is the nucleotide sequence of primer VH7LDRHU.

SEQ ID NO: 53 is the nucleotide sequence of primer Hu lambda sig 1.

SEQ ID NO: 54 is the nucleotide sequence of primer VH1LDRHU.

SEQ ID NO: 55 is the amino acid sequence of F598 heavy chain variable region including some constant region sequence.

SEQ ID NO: 56 is the nucleotide sequence of F598 heavy chain variable region including some constant region sequence.

SEQ ID NO: 57 is the amino acid sequence of F598 light chain variable region including some constant region sequence.

SEQ ID NO: 58 is the amino acid sequence of F628 heavy chain variable region including some constant region sequence.

SEQ ID NO: 59 is the nucleotide sequence of F628 heavy chain variable region including some constant region sequence.

SEQ ID NO: 60 is the amino acid sequence of F630 light chain variable region including some constant region sequence.

SEQ ID NO: 61 is the nucleotide sequence of F630 light chain variable region including some constant region sequence.

DETAILED DESCRIPTION OF THE INVENTION

The invention provides compositions and methods useful, inter alia, for immunization of humans and animals against infection by bacterial strains that express poly-N-acetyl glucosamine (PNAG) as well as detection of such pathogens. Such bacterial strains include but are not limited to coagulase-negative and coagulase-positive Staphylococci such as S. aureus and S. epidermis. The invention further provides peptides that bind to various forms of PNAG expressed by some bacterial strains.

The invention is based in part on the discovery, isolation and characterization of a number of human monoclonal antibodies that bind to various forms of PNAG (including highly acetylated forms, poorly acetylated forms and deacetylated forms, as described below). These antibodies are produced by hybridomas deposited with the ATCC under ATCC Accession Nos. PTA-5931, PTA-5932 and PTA-5933 on Apr. 21, 2004 in accordance with the Budapest Patent Treaty. The hybridomas and the antibodies they produce are designated F598, F628 and F630. These hybridomas are referred to herein repeatedly. It is to be understood that reference to hybridomas (or antibodies produced by hybridomas) having ATCC Accession Nos. PTA-5931, PTA-5932 and PTA-5933 means the afore-mentioned hybridomas. The deposited hybridomas were produced from B cells harvested from a human subject recovering from a Staphylococcal infection. The B cells were transformed with the Epstein-Barr virus and then fused with the human-mouse myeloma cell line HMMA 2.5 to generate the deposited hybridomas.

PNAG exists in nature in various forms that differ according to the degree of acetate substitutions. Acetate substitutions can range from 0-100%. As used herein, PNAG refers to "native PNAG" corresponding to the naturally occurring mixture of PNAG with the aforementioned range of acetate substitutions. Poorly acetylated PNAG is a subpopulation of PNAG polysaccharides in which less than 50% of amino groups of glucosamine are substituted with acetate. As used herein, the term dPNAG embraces both poorly acetylated PNAG as well as completely deacetylated PNAG (i.e., dPNAG refers to a subset of PNAG polysaccharides that comprise 0—less than 50% acetate substituents).

PNAG has the following structure:

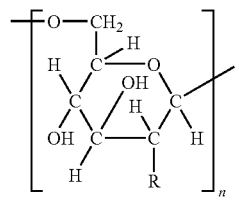

where, n is an integer ranging from 2 to greater than or equal to 300, R is selected from the group consisting of —NH—CO—CH$_3$ and —NH$_2$. PNAG has a beta (β) 1-6 linkage (i.e., it is comprised of glucosamine monomer units linked together by beta (β) 1-6 linkages).

PNAG may be a homo-polymer. A homo-polymer is one in which the R groups of the glucosamine residues are identical. The homo-polymer may comprise solely unsubstituted R groups (i.e., R=NH$_2$). PNAG can also be a hetero-polymer with a mixture of —NH$_2$ and —NH—CO—CH$_3$ groups at the R position. dPNAG has the identical structure as PNAG with the exception that less than 50% of the R groups are —NH—CO—CH$_3$.

PNAG and dPNAG can be naturally occurring and prepared from any bacterial strain carrying the ica locus (or a homologous locus such as the pga locus), producing the biosynthetic enzymes encoded by this locus, and using these enzymes to synthesize PNAG or dPNAG. Bacteria that express PNAG include Staphylococci such as S. aureus and S. epidermidis, E. coli such as E. coli strains O157:H7 and CFT073, Yersinia pestis, Yersinia entercolitica, Xanthomonas axonopodis, Pseudomonas fluorescens (all of which are sequenced species with complete pgaABCD loci), and Actinobacillus actinomycetemcomitans (AA), Actinobacillus pleuropneumoniae (Ap), Ralstonia solanacearum (e.g., megaplasmid form), Bordetella pertussis, Bordetella parapertussis and Bordetella bronchiseptica (all of which contain pgaABC genes but apparently lack a pgaD homologue). pgaD apparently is not required for PNAG expression as pgaABC encoding species such as AA and Ap (listed above) make PNAG.

Bacteria that express PNAG are bacteria that carry the ica locus or a homologous locus such as the pga locus. For example, PNAG-expressing Staphylococci are Staphylococci that carry the ica locus. PNAG-expressing bacterial strains include dPNAG-expressing bacterial strains. For example, PNAG-expressing Staphylococci include dPNAG-expressing Staphylococci. These strains include but are not limited to S. epidermis and S. aureus, as well as other strains (e.g., S. carnosus) that have been transformed with the genes in the ica locus or homologous locus such as the pga locus. In particular, PNAG can be prepared from specific strains including S. epidermis RP62A (ATCC number 35984), S. epidermis RP12 (ATCC number 35983), S. epidermis M187, S. carnosus TM300 (pCN27), S. aureus RN4220 (pCN27), S. aureus MN8 mucoid, E. coli O157:H7 and E. coli CFT073. dPNAG may also be synthesized de novo or via modification of native PNAG. PNAG and dPNAG can be prepared according to the methods described in Maira-Litran et al. Infect Immun. 2002 August; 70(8):4433, and in U.S. patent application Ser. No. 10/713,790 filed on Nov. 12, 2003.

PNAG is also expressed by other bacteria including but not limited to E. coli, Yersinia pestis (Y. pestis), Y. entercolitica, Xanthomonas axonopodis (X. axonopodis), Pseudomonas fluorescens (P. fluorescens), Actinobacillus actinomycetem-

*comitans* (*A. actinomycetemcomitans*), *A. pleuropneumoniae, Ralstonia solanacearum* (*R. solanacearum*), *Bordetella pertussis* (*B. pertussis*), *B. parapertussis* and *B. bronchiseptica*. As described in the Examples, 17 out of 18 urinary tract infection *E. coli* isolates carried the pga locus. Of these, about one third expressed relatively high levels of PNAG, about one third expressed relatively intermediate levels of PNAG, and the remaining third expressed relatively low levels of PNAG. The above analyses were carried out by immunoblot using antisera raised to *S. aureus* PNAG. This is evidence that PNAG from one species can be used to raise antibodies (and accordingly binding peptides) to other species that express PNAG.

Thus, in one aspect, the invention provides binding peptides and antibodies. The antibodies of the invention bind to Staphylococcal PNAG/dPNAG and enhance opsonophagocytosis of species that elaborate PNAG (i.e., opsonophagocytic human monoclonal antibodies specific for Staphylococcal PNAG/dPNAG). The antibodies are referred to herein as anti-Staphylococcal PNAG/dPNAG antibodies. It is to be understood, however, that such antibodies are able to bind PNAG/dPNAG regardless of its source. Accordingly, antibodies of the invention that are defined as binding to, for example, Staphylococcal PNAG/dPNAG and capable of detecting and/or enhancing opsonophagocytosis of, for example, Staphylococcal species are also capable of detecting and/or enhancing opsonophagocytosis of non-Staphylococcal PNAG-expressing bacteria.

An anti-Staphylococcal PNAG/dPNAG antibody is an antibody that a) binds to both PNAG and dPNAG, b) binds to PNAG but not dPNAG, or c) binds to dPNAG but not PNAG. Preferred antibodies bind to dPNAG.

Antibodies F598, F628 and F630 are all able to bind to native PNAG and some are also able to bind to dPNAG. Although not intending to be bound by any mechanism or theory, it is believed that antibodies that recognize dPNAG are more likely to bind specifically to parts of the PNAG molecule that do not contain acetate groups, rather than to parts of the molecule that include substituents such as the acetate substitutions. For example, antibodies that bind to dPNAG may recognize and bind to the backbone of PNAG rather than its acetate substituents. These antibodies are capable of mediating opsonophagocytic killing of PNAG-expressing bacteria such as but not limited to Staphylococcal or *E. coli* isolates from infected human subjects. When used in vivo in murine models of Staphylococcal infection, the antibodies provide protection to Staphylococcal challenge. The conditions under which each monoclonal antibody provides protection may vary. These and other findings are described in greater detail in the Examples.

Although not intending to be bound by any particular theory, it is believed that progression of infection by PNAG-expressing bacteria (such as Staphylococcal infection) is due to a failure to produce an adequate immune response that eliminates the pathogen. Specifically, one of the defects is a failure to produce opsonophagocytic antibodies specific for PNAG (such as that produced by Staphylococci.)

Opsonophagocytic antibodies are antibodies that deposit themselves onto an antigen or onto a bacterium with and without the ability to recruit additional deposition of components of the complement system and facilitate the phagocytosis of the antigen or bacterium by phagocytic cells such as antigen presenting cells (e.g., macrophages or dendritic cells), or polymorphonuclear neutrophils. Phagocytosis can proceed in an Fc-mediated manner that involves only the antibody bound to the antigen or bacterium. Phagocytosis can also proceed by binding of complement receptors on phagocytes to complement opsonins on bacterial surfaces to which antibodies have deposited. Phagocytosis can also proceed by a combination of these two mechanisms. The ability to provide opsonophagocytic antibodies to the site of infection should therefore contribute to the eradication of the infection more effectively than previously possible.

Both PNAG and dPNAG are highly immunogenic in vivo and are capable of eliciting antibodies that mediate opsonic killing and protection from infection, it is hypothesized that dPNAG preferentially elicits antibodies that mediate opsonic killing and protection from infection. The dPNAG polysaccharide is therefore useful, inter alia, in the generation of immune responses, including antibody dependent immune responses, to PNAG-expressing bacterial strains such as but not limited to Staphylococci. The antibodies elicited following dPNAG administration recognize dPNAG and in important embodiments also recognize highly acetylated forms of PNAG.

Thus, the invention relates to the identification and use of peptides that bind to PNAG and/or dPNAG. Peptides that bind to Staphylococcal PNAG and/or dPNAG are referred to herein as PNAG/dPNAG-binding peptides. Again, it is to be understood that such binding peptides are able to bind PNAG/dPNAG regardless of source. PNAG/dPNAG-binding peptides include a) peptides that bind to both PNAG and dPNAG, b) peptides that bind to PNAG and not to dPNAG (referred to herein as PNAG-binding peptides), and c) peptides that bind to dPNAG and not to PNAG (referred to herein as dPNAG-binding peptides). In preferred embodiments, the peptides at least bind to dPNAG (thereby embracing afore-mentioned categories (a) and (c)).

The peptides of the invention minimally comprise regions that bind to PNAG/dPNAG (i.e., Staphylococcal PNAG/dPNAG-binding regions). As used herein, a Staphylococcal PNAG/dPNAG-binding region is a region that a) binds to both PNAG and dPNAG, b) binds to PNAG but not dPNAG (referred to herein as a PNAG-binding region), or c) binds to dPNAG but not PNAG (referred to herein as a dPNAG-binding region), regardless of the source of PNAG/dPNAG. Preferably, the PNAG/dPNAG binding region is a region that at least binds dPNAG (and therefore embraces categories (a) and (c)). Staphylococcal PNAG/dPNAG-binding regions derive from the PNAG/dPNAG-binding regions of the antibodies of the invention, or alternatively, they are functionally equivalent variants of such regions.

Accordingly, two particularly important classes of antibody-derived PNAG/dPNAG-binding regions are variable regions and CDRs of the antibodies described herein or produced by hybridomas deposited with the ATCC under ATCC Accession Nos. PTA-5931, PTA-5932 and PTA-5933 on Apr. 21, 2004. CDR and variable region nucleic acids can be cloned from antibody-producing cells such as those on deposit as described in the Examples.

An antibody, as is well known in the art, is an assembly of polypeptide chains linked by disulfide bridges. Two principle amino acid chains, referred to as the light chain and heavy chain, make up all major structural isotypes of antibody. Both heavy chains and light chains are further divided into subregions referred to as variable regions and constant regions. In some instances, the peptides encompass the antibody heavy and light chain variable regions of the foregoing antibodies. The heavy chain variable region is a peptide which generally ranges from 100 to 150 amino acids in length. The light chain variable region is a peptide which generally ranges from 80 to 130 amino acids in length.

As is also well-known in the art, CDRs of an antibody are the portions of the antibody variable region which are largely responsible for the binding specificity of an antibody for a given antigen or antigenic epitope. The CDRs directly interact with the epitope of the antigen (see, in general, Clark, 1986; Roitt, 1991). In both the heavy chain and the light chain variable regions of IgG immunoglobulins, there are four framework regions (FR1 through FR4) separated respectively by three complementarity determining regions (CDR1, CDR 2 and CDR3). The framework regions (FRs) maintain the tertiary structure of the paratope, which is the portion of the antibody which is involved in the interaction with the antigen or antigenic epitope. CDRs, and in particular CDR3, and more particularly heavy chain CDR3, contribute substantially to antibody specificity. Because CDRs, and in particular CDR3, confer a large proportion of antigenic specificity on the antibody, these regions may be incorporated into other antibodies or peptides to confer the identical antigenic specificity onto that antibody or peptide.

Preferably, the PNAG/dPNAG-binding peptides minimally encompass at least one CDR from those described herein or those that can be derived from the deposited hybridomas (i.e., a Staphylococcal PNAG/dPNAG-binding CDR). As used herein, a Staphylococcal PNAG/dPNAG-binding CDR is a CDR described herein or is a CDR derived from hybridomas deposited under ATCC Accession Nos. PTA-5931, PTA-5932 and PTA-5933. Staphylococcal PNAG/dPNAG-binding CDRs include a) CDRs that bind to both PNAG and dPNAG, b) CDRs that bind to PNAG and not to dPNAG (referred to herein as PNAG-binding CDRs), and c) CDRs that bind to dPNAG and not to PNAG (referred to herein as dPNAG-binding CDRs), regardless of the source of the PNAG/dPNAG. These peptides preferably contain at least one Staphylococcal PNAG/dPNAG-binding CDR.

The Staphylococcal PNAG/dPNAG-binding region may be a Staphylococcal PNAG/dPNAG-binding CDR1, a Staphylococcal PNAG/dPNAG-binding CDR2, or a Staphylococcal PNAG/dPNAG-binding CDR3, all of which are derived from the antibodies and antibody variable chains disclosed herein.

As used herein, a "Staphylococcal PNAG/dPNAG-binding CDR1" is a CDR1 that binds, preferably specifically, to Staphylococcal PNAG/dPNAG, and is derived from either the heavy or light chain variable regions of the antibodies described herein or produced by hybridomas deposited under ATCC Accession Nos. PTA-5931, PTA-5932 and PTA-5933. It may have an amino acid sequence selected from the group consisting of SEQ ID NO: 7, SEQ ID NO: 10, SEQ ID NO: 13, SEQ ID NO: 16, SEQ ID NO: 19 and SEQ ID NO: 22. Similar respective definitions apply to Staphylococcal PNAG/dPNAG-binding CDR2 and CDR3.

A "Staphylococcal PNAG/dPNAG-binding CDR2" is a CDR2 that binds, preferably specifically, to Staphylococcal PNAG/dPNAG, and is derived from either the heavy or light chain variable regions of the antibodies described herein or produced by the hybridomas deposited under ATCC Accession Nos. PTA-5931, PTA-5932 and PTA-5933. It may have an amino acid sequence selected from the group consisting of SEQ ID NO: 8, SEQ ID NO: 11, SEQ ID NO: 14, SEQ ID NO: 17, SEQ ID NO: 20 and SEQ ID NO: 23.

A "Staphylococcal PNAG/dPNAG-binding CDR3" is a CDR3 that binds, preferably specifically, to Staphylococcal PNAG/dPNAG, and is derived from either the heavy or light chain variable regions of the antibodies described herein or produced by the hybridomas deposited under ATCC Accession Nos. PTA-5931, PTA-5932 and PTA-5933. It may have an amino acid sequence selected from the group consisting of SEQ ID NO: 9, SEQ ID NO: 12, SEQ ID NO: 15, SEQ ID NO: 18, SEQ ID NO: 21 and SEQ ID NO: 24.

In addition to the sequences listed above, the invention intends to embrace functionally equivalent variants of these sequences including conservative substitution variants in either the amino acid or nucleotide sequence, as described in greater detail below.

The peptides of the invention, including but not limited to the opsonophagocytic antibodies discussed herein, are useful inter alia in diagnostic methods aimed at detecting, in a sample in or from a subject, the PNAG/dPNAG antigen or PNAG-expressing bacteria (such as but not limited to Staphylococcal bacteria that express PNAG). At a minimum, peptides useful in these methods need only recognize and bind to PNAG/dPNAG (such as Staphylococcal PNAG/dPNAG) regardless of whether they also enhance opsonization and phagocytosis. In important embodiments, the antibodies and fragments thereof bind to PNAG/dPNAG selectively. Accordingly, they need only possess one or more of the CDRs derived from the antibody clones described herein or produced by the hybridomas deposited under ATCC Accession Nos. PTA-5931, PTA-5932 and PTA-5933. In preferred embodiments, the peptides comprise a PNAG/dPNAG-binding CDR3, and even more preferably, the peptides comprise a heavy chain PNAG/dPNAG-binding CDR3. It is to be understood that not all of the CDRs are required in order to effect binding to PNAG/dPNAG. However, in some embodiments the peptides comprise all of the CDRs of a given antibody clone disclosed herein or produced by hybridomas deposited under ATCC Accession Nos. PTA-5931, PTA-5932 and PTA-5933.

In addition, it should be understood that the invention also embraces the exchange of CDRs between the variable regions provided herein. Preferably, a heavy chain CDR is exchanged with another heavy chain variable region CDR, and likewise, a light chain CDR is exchanged with another light chain variable region CDR.

The amino acid sequences of the CDRs of the variable chains disclosed in the present invention are as follows:

| Clone | Chain | CDR | SEQ ID NO: | Sequence |
|---|---|---|---|---|
| F598 | Hv | CDR1 | 7 | GYYWS |
| F598 | Hv | CDR2 | 8 | YIHYSRSTNSNPALKS |
| F598 | Hv | CDR3 | 9 | DTYYYDSGDYEDAFDI |
| F598 | Lt | CDR1 | 10 | TLSSGHSNYAIA |
| F598 | Lt | CDR2 | 11 | VNRDGSHIRGD |
| F598 | Lt | CDR3 | 12 | QTWGAGIRV |
| F628 | Hv | CDR1 | 13 | NYYWS |
| F628 | Hv | CDR2 | 14 | YIHYSGSTNSNPSLKS |
| F628 | Hv | CDR3 | 15 | DTYYESSGHWFDGLDV |
| F628 | Lt | CDR1 | 16 | TLDSEHSRYTIA |
| F628 | Lt | CDR2 | 17 | VKSDGSHSKGD |
| F628 | Lt | CDR3 | 18 | QTWGPGIRV |
| F630 | Hv | CDR1 | 19 | NFGIS |
| F630 | Hv | CDR2 | 20 | WVSTYNGRTNYAQKFRG |
| F630 | Hv | CDR3 | 21 | DYYETSGYAYDDFAI |
| F630 | Lt | CDR1 | 22 | TLSSGHSTYAIA |
| F630 | Lt | CDR2 | 23 | VNSDGSHTKGD |
| F630 | Lt | CDR3 | 24 | QTWGPGIRV |

The nucleotide sequences of the CDRs of the variable chains disclosed in the present invention are as follows:

| Clone | Chain | CDR | SEQ ID NO: | Sequence |
|---|---|---|---|---|
| F598 | Hv | CDR1 | 31 | GGT TAC TAC TGG AGT |
| F598 | Hv | CDR2 | 32 | TAT ATT CAT TAT AGT AGG AGC ACC AAC TCC AAC CCC GCC CTC AAG AGT |
| F598 | Hv | CDR3 | 33 | GAT ACC TAT TAC TAT GAT AGT GGT GAT TAT GAG GAT GCT TTT GAT ATT |
| F598 | Lt | CDR1 | 34 | ACT CTG AGC AGT GGC CAC AGC AAC TAC GCC ATC GCT |
| F598 | Lt | CDR2 | 35 | GTT AAC AGA GAT GGC AGC CAC ATC AGG GGG GAC |
| F598 | Lt | CDR3 | 36 | CAG ACC TGG GGC GCT GGC ATT CGA GTG |
| F628 | Hv | CDR1 | 37 | AAT TAC TAC TGG AGT |
| F628 | Hv | CDR2 | 38 | TAT ATC CAT TAT AGT GGG AGC ACC AAC TCC AAT CCA TCC CTC AAG AGT |
| F628 | Hv | CDR3 | 39 | GAT ACT TAC TAT GAA AGT AGT GGT CAT TGG TTC GAC GGT TTG GAC GTC |
| F628 | Lt | CDR1 | 40 | ACT CTG GAC AGT GAA CAC AGC AGA TAC ACC ATC GCA |
| F628 | Lt | CDR2 | 41 | GTT AAG AGT GAT GGC AGT CAC AGC AAG GGG GAC |
| F628 | Lt | CDR3 | 42 | CAG ACT TGG GGC CCT GGC ATT CGA GTG |
| F630 | Hv | CDR1 | 43 | AAC TTT GGT ATC AGT |
| F630 | Hv | CDR2 | 44 | TGG GTC AGC ACT TAC AAT GGT CGC ACA AAT TAT GCA CAG AAG TTC CGG GGC |
| F630 | Hv | CDR3 | 45 | GAT TAC TAT GAG ACT AGT GGT TAC GCC TAT GAT GAT TTT GCG ATC |
| F630 | Lt | CDR1 | 46 | ACT CTG AGC AGT GGG CAC AGC ACC TAC GCC ATC GCG |
| F630 | Lt | CDR2 | 47 | GTC AAC AGT GAT GGC AGC CAC ACC AAG GGG GAC |
| F630 | Lt | CDR3 | 48 | CAG ACG TGG GGC CCT GGC ATT CGA GTG |

The peptides may also comprise a Staphylococcal PNAG/dPNAG-binding variable region. A Staphylococcal PNAG/dPNAG-binding variable region is a variable region (preferably an antibody variable region as described herein or as derived from hybridomas deposited under ATCC Accession Nos. PTA-5931, PTA-5932 and PTA-5933) that a) binds to both PNAG and dPNAG, b) binds to PNAG but not dPNAG (referred to herein as a PNAG-binding variable region), or c) binds to dPNAG but not PNAG (referred to herein as a dPNAG-binding variable region), regardless of the PNAG/dPNAG source.

The present invention provides at least six different variable regions, at least three of which are heavy chain variable regions and at least three of which are light chain variable regions. SEQ ID NO: 1 and SEQ ID NO: 25 correspond to the amino acid and nucleotide sequence of the heavy chain variable region derived from antibody clone F598. SEQ ID NO: 2 and SEQ ID NO: 26 correspond to the amino acid and nucleotide sequence of the light chain variable region derived from antibody clone F598. SEQ ID NO: 3 and SEQ ID NO: 27 correspond to the amino acid and nucleotide sequence of the heavy chain variable region derived from antibody clone F628. SEQ ID NO: 4 and SEQ ID NO: 28 correspond to the amino acid and nucleotide sequence of the light chain variable region derived from antibody clone F628. SEQ ID NO: 5 and SEQ ID NO: 29 correspond to the amino acid and nucleotide sequence of the heavy chain variable region derived from antibody clone F630. SEQ ID NO: 6 and SEQ ID NO: 30 correspond to the amino acid and nucleotide sequence of the light chain variable region derived from antibody clone F630.

It is to be understood that the nucleic acids or peptides of the invention may be derived from the sequences provided herein or from the deposited hybridomas. These sequences can be cloned (e.g., by PCR) and inserted into a vector and/or cells in order to produce peptides corresponding to full length variable regions or fragments of full length variable regions, and antibodies comprising the variable regions. It is therefore possible to generate antibodies or fragments thereof that comprise a combination of light and heavy chain variable regions. For example, an antibody of the invention may comprise the heavy chain variable region from MAb F598 (or from the antibody produced by the deposited F598 hybridoma) and the light chain variable region of F630 (or from the antibody produced by the deposited F630 hybridoma). It is to be understood that any combination of heavy and light chain variable regions (as disclosed herein or as comprised in antibodies produced by hybridomas deposited under ATCC Accession Nos. PTA-5931, PTA-5932 and PTA-5933) can be used in the synthesis of an antibody or antibody fragment according to the invention.

Accordingly, the invention embraces antibodies or antibody fragments that are comprised of the following variable region combinations: SEQ ID NO:1 and SEQ ID NO:2; SEQ ID NO:1 and SEQ ID NO:4; SEQ ID NO:1 and SEQ ID NO:6; SEQ ID NO:3 and SEQ ID NO:2; SEQ ID NO:3 and SEQ ID NO:4; SEQ ID NO:3 and SEQ ID NO:6; SEQ ID NO:5 and SEQ ID NO:2; SEQ ID NO:5 and SEQ ID NO:4; and SEQ ID NO:5 and SEQ ID NO:6.

Similarly, the invention embraces antibodies or antibody fragments that are comprised of the following variable region combinations:

1. heavy chain variable region from hybridoma F598 having ATCC Accession No. PTA-5931 and light chain variable region from hybridoma F598 having ATCC Accession No. PTA-5931;
2. heavy chain variable region from hybridoma F598 having ATCC Accession No. PTA-5931 and light chain variable region from hybridoma F628 having ATCC Accession No. PTA-5932;
3. heavy chain variable region from hybridoma F598 having ATCC Accession No. PTA-5931 and light chain variable region from hybridoma F630 having ATCC Accession No. PTA-5933;
4. heavy chain variable region from hybridoma F628 having ATCC Accession No. PTA-5932 and light chain variable region from hybridoma F598 having ATCC Accession No. PTA-5931;
5. heavy chain variable region from hybridoma F628 having ATCC Accession No. PTA-5932 and light chain variable region from hybridoma F628 having ATCC Accession No. PTA-5932;
6. heavy chain variable region from hybridoma F628 having ATCC Accession No. PTA-5932 and light chain variable region from hybridoma F630 having ATCC Accession No. PTA-5933;
7. heavy chain variable region from hybridoma F630 having ATCC Accession No. PTA-5933 and light chain variable region from hybridoma F598 having ATCC Accession No. PTA-5931;
8. heavy chain variable region from hybridoma F630 having ATCC Accession No. PTA-5933 and light chain variable region from hybridoma F628 having ATCC Accession No. PTA-5932; and
9. heavy chain variable region from hybridoma F630 having ATCC Accession No. PTA-5933 and light chain variable region from hybridoma F630 having ATCC Accession No. PTA-5933.

The invention intends to capture antibody and antibody fragments of various isotypes. The deposited hybridomas produce IgG2 isotype antibodies. However, the recombined immunoglobulin (Ig) genes, particularly the variable region genes, can be isolated from the deposited hybridomas, as described in the Examples, and cloned into an Ig recombination vector that codes for human Ig constant region genes of both heavy and light chains. Using this technique, IgG1 isotype antibodies that bind to Staphylococcal PNAG/dPNAG and thereby enhance opsonophagocytosis of PNAG-expressing bacteria (such as Staphylococci) have been identified, synthesized and isolated.

The antibodies may be of an IgG1, IgG2, IgG3, IgG4, IgD, IgE, IgM, IgA1, IgA2, or sIgA isotype. The invention intends to capture isotypes found in non-human species as well such as but not limited to IgY in birds and sharks. Vectors encoding the constant regions of various isotypes are known and previously described. (See, for example, Preston et al. Production and characterization of a set of mouse-human chimeric immunoglobulin G (IgG) subclass and IgA monoclonal antibodies with identical variable regions specific for *P. aeruginosa* serogroup O6 lipopolysaccharide. Infect Immun. 1998 September; 66(9):4137-42; Coloma et al. Novel vectors for the expression of antibody molecules using variable regions generated by polymerase chain reaction. J Immunol Methods. 1992 Jul. 31; 152(1):89-104; Guttieri et al. Cassette vectors for conversion of Fab fragments into full-length human IgG1 monoclonal antibodies by expression in stably transformed insect cells. Hybrid Hybridomics. 2003 June; 22(3):135-45; McLean et al. Human and murine immunoglobulin expression vector cassettes. Mol Immunol. 2000 October; 37(14): 837-45; Walls et al. Vectors for the expression of PCR-amplified immunoglobulin variable domains with human constant regions. Nucleic Acids Res. 1993 Jun. 25; 21(12): 2921-9; Norderhaug et al. Versatile vectors for transient and stable expression of recombinant antibody molecules in mammalian cells. J Immunol Methods. 1997 May 12; 204(1): 77-87.)

As used herein, the term "peptide" includes monoclonal antibodies, functionally active and/or equivalent antibody fragments, and functionally active and/or equivalent peptides and polypeptides.

The peptides of the invention are isolated peptides. As used herein, the term "isolated peptides" means that the peptides are substantially pure and are essentially free of other substances with which they may be found in nature or in vivo systems to an extent practical and appropriate for their intended use. In particular, the peptides are sufficiently pure and are sufficiently free from other biological constituents of their hosts cells so as to be useful in, for example, producing pharmaceutical preparations or sequencing. Because an isolated peptide of the invention may be admixed with a pharmaceutically acceptable carrier in a pharmaceutical preparation, the peptide may comprise only a small percentage by weight of the preparation. The peptide is nonetheless substantially pure in that it has been substantially separated from the substances with which it may be associated in living systems.

The peptides of the invention bind to PNAG and/or dPNAG, preferably in a selective manner. As used herein, the terms "selective binding" and "specific binding" are used interchangeably to refer to the ability of the peptide to bind with greater affinity to PNAG and/or dPNAG and fragments thereof than to non-PNAG derived compounds. That is, peptides that bind selectively to PNAG and/or dPNAG will not bind to non-PNAG derived compounds to the same extent and with the same affinity as they bind to PNAG and/or dPNAG and fragments thereof, with the exception of cross reactive antigens or molecules made to be mimics of PNAG/dPNAG such as peptide mimetics of carbohydrates or variable regions of anti-idiotype antibodies that bind to the PNAG/dPNAG-binding peptides in the same manner as PNAG/dPNAG. Antibodies that bind selectively to PNAG bind to PNAG with greater affinity than to dPNAG. Antibodies that bind to dPNAG may also bind to dPNAG with lesser, comparable or greater affinity than to PNAG. In preferred embodiments, the peptides of the invention bind solely to PNAG and/or dPNAG and fragments thereof, and even more preferably, they at least bind to dPNAG. As used herein, a binding peptide that binds selectively or specifically to Staphylococcal PNAG/dPNAG may also bind PNAG/dPNAG from other sources and will bind with lesser affinity (if at all) to non-PNAG/dPNAG derived compounds. Lesser affinity may include at least 10% less, 20% less, 30% less, 40% less, 50% less, 60% less, 70% less, 80% less, 90% less, or 95% less. Thus, "selective" in this sense refers to the binding to PNAG/dPNAG rather than to the *Staphylococcus*-derived form of PNAG/dPNAG.

As stated earlier, the invention provides peptides e.g., antibodies or antibody fragments, that bind to Staphylococcal PNAG and/or dPNAG. Such antibodies preferably enhance opsonization and phagocytosis (i.e., opsonophagocytosis) of PNAG-expressing bacteria (such as PNAG-expressing Staphylococci), and as a result are useful in the prevention and therapy of some forms of bacterial infections in a subject.

Opsonization refers to a process by which phagocytosis is facilitated by the deposition of opsonins (e.g., antibody and/or opsonic complement factors such as C4b or C3b or any other factor capable of promoting opsonophagocytosis) on the antigen. Phagocytosis and opsonophagocytosis refer to the process by which phagocytic cells (e.g., macrophages, dendritic cells, and polymorphonuclear leukocytes (PMNL)) engulf material and enclose it within a vacuole (e.g., a phagosome) in their cytoplasm. Thus, antibodies or antibody fragments that opsonize bacteria and enhance phagocytosis are antibodies or antibody fragments that recognize and deposit onto an antigen, and in doing so, facilitate the uptake and engulfment of the antigen (and the antigen-bearing substance, e.g., Staphylococcal bacteria) by phagocytic cells. Generally, in order to enhance phagocytosis and opsonization, the antibody comprises an Fc domain or region. The Fc domain is recognized by Fc receptor bearing cells (e.g., antigen presenting cells such as macrophages, or PMNL). As used herein, "to enhance opsonophagocytosis" means to increase the likelihood that an antigen or an antigen bearing substrate will be recognized and engulfed by a phagocytic cell, via antibody deposition. This enhancement can be measured by reduction in bacterial load in vivo or by bacterial cell killing in vitro using the in vitro methods described below.

Opsonization assays are standard in the art. Generally such assays measure the amount of bacterial killing in the presence of an antibody, an antigen (expressed on the target bacterial cell), complement, and phagocytic cells. Serum from either animals or humans is commonly used as a source of complement, and polymorphonuclear cells from animals or humans are commonly used as a source of phagocytic cells. The target cell for opsonophagocytic killing can be prokaryotic (as in the present invention) or eukaryotic, depending upon which cell type expresses the antigen. Cell killing can be measured by viable cell counts prior to and following incubation of the reaction components. Alternatively, cell killing can be quantitated by measuring cell contents in the supernatant of the reaction mixture (e.g., release of radioactive chromium or release of intracellular enzymes such as lactate dehydrogenase). Other assays will be apparent to those of skill in the art, having read the present specification, which are useful for determining whether an antibody or antibody fragment that binds to Staphylococcal PNAG and/or dPNAG also stimulates opsonization and phagocytosis.

The present invention provides, inter alia, PNAG/dPNAG-specific human monoclonal antibodies that enhance opsonic killing of PNAG-expressing bacteria such as but not limited to Staphylococci. These antibodies are named F598, F628 and F630. When used in vivo in humans, human monoclonal antibodies are far less likely to be immunogenic (as compared to antibodies from another species). As a result, these antibodies represent novel agents useful in the design of vaccines as well as passive immunotherapy targeting bacterial strains that express PNAG such as but not limited to Staphylococci.

The synthesis of these monoclonal antibodies is described in the Examples. Briefly, the antibodies were derived as follows: B cells were harvested from individuals recovering from a Staphylococcal infection. Harvested B cells were transformed using Epstein-Barr virus and, after a period of growth and screening for secretion of antibody to PNAG/dPNAG, fused with the immortalized human-mouse myeloma cell line partner designated HMMA 2.5. After an initial period of growth of the fused cells, single antibody producing clones were isolated, grown and analyzed separately using a binding assay (e.g., ELISA). Three hybridomas were selected based on the ability of their secreted antibody to bind to Staphylococcal PNAG and/or dPNAG. All three antibodies were of the IgG2 isotype and were used as a source of antibody of the IgG2 isotype. Variable regions were cloned from the hybridomas by PCR as described above.

Variable region nucleic acids for the heavy and light chains of the antibodies were cloned into an human Ig expression vector (i.e., TCAE6) that contained the IgG1 (gamma 1) constant region coding sequences for the heavy chain and the lambda constant region for the light chains. (See, for example, Preston et al. Production and characterization of a set of mouse-human chimeric immunoglobulin G (IgG) subclass and IgA monoclonal antibodies with identical variable regions specific for P. aeruginosa serogroup O6 lipopolysaccharide. Infect Immun. 1998 September; 66(9):4137-42.) The variable regions can be placed in any vector that encodes constant region coding sequences. For example, human Ig heavy-chain constant-region expression vectors containing genomic clones of the human IgG2, IgG3, IgG4 and IgA heavy-chain constant-region genes and lacking variable-region genes have been described in Coloma, et al. 1992 J. Immunol. Methods 152:89-104.)

These expression vectors were then transfected into cells (e.g., CHO DG44 cells), the cells were grown in vitro, and IgG1 was subsequently harvested from the supernatant. Resultant antibodies possessed human variable regions and human IgG1 and lambda constant regions. Their ability to bind to PNAG and/or dPNAG and to enhance opsonization and phagocytosis of PNAG-expressing bacteria such as Staphylococci was evaluated using binding and opsonophagocytic killing assays such as those described herein.

"Isolated antibodies" as used herein refer to antibodies that are substantially physically separated from other cellular material (e.g., separated from cells which produce the antibodies) or from other material that hinders their use either in the diagnostic or therapeutic methods of the invention. Preferably, the isolated antibodies are present in a homogenous population of antibodies (e.g., a population of monoclonal antibodies). Compositions of isolated antibodies can however be combined with other components such as but not limited to pharmaceutically acceptable carriers, adjuvants, and the like.

"Isolated antibody producing cells" including isolated hybridomas and isolated recombinant cells (such as those described herein), as used herein, refer to antibody-producing cells that are substantially physically separated from other cells, other bodily material (e.g., ascites tissue and fluid), and other material that hinders their use in the production of, for example, an isolated and preferably homogenous antibody population. The hybridomas deposited with the ATCC under the Budapest Treaty as ATCC Accession Nos. PTA-5931, PTA-5932 and PTA-5933 on Apr. 21, 2004 are considered to be examples of isolated antibody producing cells and more specifically isolated hybridomas.

Thus in one embodiment, the peptide of the invention is an isolated intact soluble monoclonal antibody specific for Staphylococcal PNAG and/or dPNAG. As used herein, the term "monoclonal antibody" refers to a homogenous population of immunoglobulins that specifically bind to an identical epitope (i.e., antigenic determinant). The peptide of the invention in one embodiment is, for example, a monoclonal antibody having a heavy chain variable region having an amino acid sequence of SEQ ID NO: 1, SEQ ID NO:3 or SEQ ID NO:5. The monoclonal antibody can have a light chain variable region having an amino acid sequence of SEQ ID NO:2, SEQ ID NO:4 or SEQ ID NO:6. Monoclonal antibodies having any combination of light chain and heavy chain variable regions are embraced by the invention.

The invention intends to encompass antibodies other than, for example, clones F598, F628 and F630, provided that such antibodies have the binding characteristics of the monoclonal antibodies described herein. Optionally, these additional antibodies also enhance opsonophagocytosis of PNAG-expressing bacterial strains such as but not limited to PNAG-expressing Staphylococci. One of ordinary skill in the art can easily identify antibodies having the functional characteristics (e.g., binding, opsonizing and phagocytosing attributes) of these monoclonal antibody using the screening and binding assays set forth in detail herein.

In other embodiments, the peptide is an antibody fragment. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford; and Pier G B, Lyczak J B, Wetzler L M, (eds). Immunology, Infection and Immunity (2004) 1$^{st}$ Ed. American Society for Microbiology Press, Washington D.C.). The pFc' and Fc regions of the antibody, for example, are effectors of the complement cascade and can mediate binding to Fc receptors on phagocytic cells, but are not involved in antigen binding. An antibody from which the pFc' region has been enzymatically cleaved, or which has been produced without the pFc' region, designated an F(ab')$_2$ fragment, retains both of the antigen binding sites of an intact antibody. An isolated F(ab')$_2$ fragment is referred to as a bivalent monoclonal fragment because of its two antigen binding sites. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd (heavy chain variable region). The Fd fragments are the major determinant of antibody specificity (a single Fd fragment may be associated with up to ten different light chains without altering antibody specificity) and Fd fragments retain epitope-binding ability in isolation.

The terms Fab, Fc, pFc', F(ab')$_2$ and Fv are employed with either standard immunological meanings [Klein, *Immunology* (John Wiley, New York, N.Y., 1982); Clark, W. R. (1986) *The Experimental Foundations of Modern Immunology* (Wiley & Sons, Inc., New York); Roitt, I. (1991) *Essential Immunology*, 7th Ed., (Blackwell Scientific Publications, Oxford); and Pier G B, Lyczak J B, Wetzler L M, (eds). Immunology, Infection and Immunity (2004) 1$^{st}$ Ed. American Society for Microbiology Press, Washington D.C.].

In other embodiments, the Fc portions of the antibodies of the invention may be replaced so as to produce IgM as well as human IgG antibodies bearing some or all of the CDRs of the monoclonal antibodies described herein or produced by the hybridomas deposited under ATCC Accession Nos. PTA-5931, PTA-5932 and PTA-5933. Of particular importance is the inclusion of a Staphylococcal PNAG/dPNAG-binding CDR3 region and, to a lesser extent, the other CDRs and portions of the framework regions of the monoclonal antibodies described herein or produced by the hybridomas deposited under ATCC Accession Nos. PTA-5931, PTA-5932 and PTA-5933. Such human antibodies will have particular clinical utility in that they will recognize and bind, preferably selectively, to Staphylococcal PNAG and/or dPNAG, but will not evoke an immune response in humans against the antibody itself.

The invention also intends to include functionally equivalent variants of the Staphylococcal PNAG/dPNAG-binding peptides. A "functionally equivalent variant" is a compound having the same function (i.e., the ability to bind to Staphylococcal PNAG and/or dPNAG and in some embodiments to facilitate opsonization of PNAG-expressing bacterial strains) as the peptides of the invention. A functionally equivalent variant may be peptide in nature but it is not so limited. For example, it may be a carbohydrate, a peptidomimetic, etc. In important embodiments, the functionally equivalent variant is a peptide having the amino acid sequence of a variable region or a CDR with conservative substitutions therein, that is still capable of binding to Staphylococcal PNAG and/or dPNAG. An example of a functionally equivalent variant of Staphylococcal PNAG/dPNAG-binding CDR3 from the heavy chain variable region of clone F598 (i.e., SEQ ID NO: 1) is a peptide having conservative substitutions in SEQ ID NO:1 which bind, preferably specifically, to Staphylococcal PNAG and/or dPNAG, and optionally which enhances opsonization of PNAG-expressing bacterial strains such as PNAG-expressing Staphylococci. As used herein, "conservative substitution" refers to an amino acid substitution which does not alter the relative charge or size characteristics of the peptide in which the amino acid substitution is made. Conservative substitutions of amino acids include substitutions made amongst amino acids with the following groups: (1) M,I,L,V; (2) F,Y,W; (3) K,R,H; (4) A,G; (5) S,T; (6) Q,N; and, (7) E,D.

Functional equivalent variants can have identity to the peptides explicitly recited herein. That is, such variants may have at least 99% identity, at least 98% identity, at least 97% identity, at least 96% identity, at least 95% identity, at least 94% identity, at least 93% identity, at least 92% identity, at least 91% identity, at least 90% identity, at least 85% identity, at least 80% identity, at least 75% identity, at least 70% identity, at least 65% identity, at least 60% identity, at least 55% identity, at least 50% identity, at least 45% identity, at least 40% identity, at least 35% identity, at least 30% identity, at least 25% identity, at least 20% identity, at least 10% identity, or at least 5% identity to the amino acid sequences provided herein.

Functional equivalence refers to an equivalent activity (e.g., binding to Staphylococcal PNAG and/or dPNAG, or enhancing opsonophagocytosis of PNAG-expressing bacteria such as PNAG-expressing Staphylococci), however it also embraces variation in the level of such activity. For example, a functional equivalent is a variant that binds to Staphylococcal PNAG and/or dPNAG with lesser, equal, or greater affinity than the monoclonal antibody clones described herein, provided that the variant is still useful in the invention (i.e., it binds to Staphylococcal PNAG and/or dPNAG and optionally enhances opsonophagocytosis of PNAG-expressing bacteria such as PNAG-expressing Staphylococci).

Such substitutions can be made by a variety of methods known to one of ordinary skill in the art. For example, amino acid substitutions may be made by PCR-directed mutation, site-directed mutagenesis according to the method of Kunkel (Kunkel, *Proc. Nat. Acad. Sci. U.S.A.* 82: 488-492, 1985), or by chemical synthesis of a gene encoding the particular CDR or a peptide comprising the CDR amino acid sequences described herein. These and other methods for altering a CDR containing peptide will be known to those of ordinary skill in the art and may be found in references which compile such methods, e.g. Sambrook or Ausubel, noted above. In some embodiments, however, due to the size of the CDRs, it may be more convenient to synthesize the variant peptides using a peptide synthesizer such as those commercially available. The activity of functionally equivalent variants of the Staphylococcal PNAG/dPNAG-binding CDR can be tested by the binding assays, and in some cases biological activity assays, discussed in more detail below. As used herein, the terms "functional variant", "functionally equivalent variant" and "functionally active variant" are used interchangeably.

As used herein the term "functionally active antibody fragment" means a fragment of an antibody molecule including a Staphylococcal PNAG-binding or dPNAG-binding region of the invention which retains the ability to bind to Staphylococcal PNAG or dPNAG respectively, preferably in a specific manner. Such fragments can be used both in vitro and in vivo. In particular, well-known functionally active antibody fragments include but are not limited to F(ab')$_2$, Fab, Fv and Fd fragments of antibodies. These fragments which lack the Fc fragment of intact antibody, clear more rapidly from the circulation, and may have less non-specific tissue binding than an intact antibody (Wahl et al., *J. Nucl. Med.* 24:316-325 (1983)). As another example, single-chain antibodies can be constructed in accordance with the methods described in U.S. Pat. No. 4,946,778 to Ladner et al. Such single-chain antibodies include the variable regions of the light and heavy chains joined by a flexible linker moiety. Methods for obtaining a single domain antibody ("Fd") which comprises an isolated variable heavy chain single domain, also have been reported (see, for example, Ward et al., *Nature* 341:644-646 (1989), disclosing a method of screening to identify an antibody heavy chain variable region ($V_H$ single domain antibody) with sufficient affinity for its target epitope to bind thereto in isolated form). Methods for making recombinant Fv fragments based on known antibody heavy chain and light chain variable region sequences are known in the art and have been described, e.g., Moore et al., U.S. Pat. No. 4,462,334. Other references describing the use and generation of antibody fragments include e.g., Fab fragments (Tijssen, Practice and Theory of Enzyme Immunoassays (Elsevier, Amsterdam, 1985)), Fv fragments (Hochman et al., Biochemistry 12: 1130 (1973); Sharon et al., Biochemistry 15: 1591 (1976); Ehrlich et al., U.S. Pat. No. 4,355,023) and portions of antibody molecules (Audilore-Hargreaves, U.S. Pat. No. 4,470,925). Thus, those skilled in the art may construct antibody fragments from various portions of intact antibodies without destroying the specificity of the antibodies for Staphylococcal PNAG and/or dPNAG.

In important aspects of the invention, the functionally active antibody fragment also retains the ability to opsonize and phagocytose PNAG-expressing bacteria such as PNAG-expressing Staphylococci. In this latter instance, the antibody fragment includes an Fc region as well as an epitope binding domain. The Fc region allows the antibody fragment to bind to Fc receptor positive cells, which subsequently phagocytose the epitope bound by the Fab region of the antibody.

Additionally small peptides including those containing the Staphylococcal PNAG/dPNAG-binding CDR3 region may easily be synthesized or produced by recombinant means to produce the peptide of the invention. Such methods are well known to those of ordinary skill in the art. Peptides can be synthesized, for example, using automated peptide synthesizers which are commercially available. The peptides can be produced by recombinant techniques by incorporating the DNA expressing the peptide into an expression vector and transforming cells with the expression vector to produce the peptide.

Peptides, including antibodies, can be tested for their ability to bind to Staphylococcal PNAG and/or dPNAG using standard binding assays known in the art. As an example of a suitable assay, PNAG and/or dPNAG, such as Staphylococcal PNAG and/or dPNAG, can be immobilized on a surface (such as in a well of a multi-well plate) and then contacted with a labeled peptide. The amount of peptide that binds to the PNAG and/or dPNAG (and thus becomes itself immobilized onto the surface) may then be quantitated to determine whether a particular peptide binds to PNAG and/or dPNAG. Alternatively, the amount of peptide not bound to the surface may also be measured. In a variation of this assay, the peptide can be tested for its ability to bind directly to a PNAG-expressing colony grown in vitro.

Peptide binding can also be tested using a competition assay. If the peptide being tested (including an antibody) competes with the monoclonal antibodies or antibody fragments described herein, as shown by a decrease in binding of the monoclonal antibody or fragment, then it is likely that the peptide and the monoclonal antibody bind to the same, or at least an overlapping, epitope. In this assay system, the antibody or antibody fragment is labeled and the PNAG and/or dPNAG is immobilized onto the solid surface. These and other assays are described in more detail herein. In this way, competing peptides including competing antibodies can be identified. The invention embraces peptides and in particular antibodies (and fragments thereof) that compete with antibody F598, F628 or F630 for binding to PNAG/dPNAG (i.e., antibodies that recognize and bind to the same epitopes as F598, F628 or F630).

Standard binding assays are well known in the art, and a number of these are suitable in the present invention including ELISA, competition binding assay (as described above), sandwich assays, radioreceptor assays using radioactively labeled peptides or radiolabeled antibodies, immunoassays, etc. The nature of the assay is not essential provided it is sufficiently sensitive to detect binding of a small number of peptides.

A variety of other reagents also can be included in the binding mixture. These include reagents such as salts, buffers, neutral proteins (e.g., albumin), detergents, etc. which may be used to facilitate optimal binding. Such a reagent may also reduce non-specific or background interactions of the reaction components. Other reagents that improve the efficiency of the assay may also be used. The mixture of the foregoing assay materials is incubated under conditions under which the monoclonal antibody normally specifically binds PNAG and/or dPNAG such as Staphylococcal PNAG and/or dPNAG. Such conditions will preferably mimic physiological conditions. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours. After incubation, the presence or absence of specific binding between the peptide and PNAG and/or dPNAG is detected by any convenient method available to the user.

Typically, a plurality of assay mixtures are run in parallel with different peptides or different peptide concentrations to obtain a different response to the various concentrations. One of these concentrations serves as a negative control, i.e., at zero concentration of PNAG and/or dPNAG or at a concentration of PNAG and/or dPNAG below the limits of assay detection.

A separation step is often used to separate bound from unbound peptide or antibody. The separation step may be accomplished in a variety of ways. Conveniently, at least one of the components (e.g., peptide or antibody) is immobilized on a solid substrate via binding to PNAG and/or dPNAG. The unbound components may be easily separated from the bound fraction. The solid substrate can be made of a wide variety of materials and in a wide variety of shapes, e.g., columns or gels of polyacrylamide, agarose or sepharose, microtiter plates, microbeads, resin particles, etc. The separation step preferably includes multiple rinses or washes. For example, when the solid substrate is a microtiter plate, the wells may be washed several times with a washing solution, which typically includes those components of the incubation mixture that do not participate in specific bindings such as salts, buffer, detergent, non-specific protein, etc. Where the solid substrate is a magnetic bead, the beads may be washed one or more times with a washing solution and isolated using a magnet.

The peptides can be used alone or in conjugates with other molecules such as detection or cytotoxic agents in the detection and treatment methods of the invention, as described in more detail herein.

Typically, one of the components usually comprises, or is coupled or conjugated to a detectable label. A detectable label is a moiety, the presence of which can be ascertained directly or indirectly. Generally, detection of the label involves an emission of energy by the label. The label can be detected directly by its ability to emit and/or absorb photons or other atomic particles of a particular wavelength (e.g., radioactivity, luminescence, optical or electron density, etc.). A label can be detected indirectly by its ability to bind, recruit and, in some cases, cleave another moiety which itself may emit or absorb light of a particular wavelength (e.g., epitope tag such as the FLAG epitope, enzyme tag such as horseradish peroxidase, etc.). An example of indirect detection is the use of a first enzyme label which cleaves a substrate into visible products. The label may be of a chemical, peptide or nucleic acid molecule nature although it is not so limited. Other detectable labels include radioactive isotopes such as $P^{32}$ or $H^3$, luminescent markers such as fluorochromes, optical or electron density markers, etc., or epitope tags such as the FLAG epitope or the HA epitope, biotin, avidin, and enzyme tags such as horseradish peroxidase, β-galactosidase, etc. The label may be bound to a peptide during or following its synthesis. There are many different labels and methods of labeling known to those of ordinary skill in the art. Examples of the types of labels that can be used in the present invention include enzymes, radioisotopes, fluorescent compounds, colloidal metals, chemiluminescent compounds, and bioluminescent compounds. Those of ordinary skill in the art will know of other suitable labels for the peptides described herein, or will be able to ascertain such, using routine experimentation. Furthermore, the coupling or conjugation of these labels to the peptides of the invention can be performed using standard techniques common to those of ordinary skill in the art.

Another labeling technique which may result in greater sensitivity consists of coupling the peptides to low molecular weight haptens. These haptens can then be specifically altered by means of a second reaction. For example, it is common to use haptens such as biotin, which reacts with avidin, or dinitrophenol, pyridoxal, or fluorescein, which can react with specific anti-hapten antibodies.

Conjugation of the peptides including antibodies or fragments thereof to a detectable label facilitates, among other things, the use of such agents in diagnostic assays. Another category of detectable labels includes diagnostic and imaging labels (generally referred to as in vivo detectable labels) such as for example magnetic resonance imaging (MRI): Gd(DOTA); for nuclear medicine: $^{201}$Tl, gamma-emitting radionuclide 99 mTc; for positron-emission tomography (PET): positron-emitting isotopes, (18)F-fluorodeoxyglucose ((18)FDG), (18)F-fluoride, copper-64, gadodiamide, and radioisotopes of Pb(II) such as 203Pb; 111In.

The conjugations or modifications described herein employ routine chemistry, which chemistry does not form a part of the invention and which chemistry is well known to those skilled in the art of chemistry. The use of protecting groups and known linkers such as mono- and hetero-bifunctional linkers are well documented in the literature and will not be repeated here.

As used herein, "conjugated" means two entities stably bound to one another by any physiochemical means. It is important that the nature of the attachment is such that it does not impair substantially the effectiveness of either entity. Keeping these parameters in mind, any covalent or non-covalent linkage known to those of ordinary skill in the art may be employed. In some embodiments, covalent linkage is preferred. Noncovalent conjugation includes hydrophobic interactions, ionic interactions, high affinity interactions such as biotin-avidin and biotin-streptavidin complexation and other affinity interactions. Such means and methods of attachment are well known to those of ordinary skill in the art.

A variety of methods may be used to detect the label, depending on the nature of the label and other assay components. For example, the label may be detected while bound to the solid substrate or subsequent to separation from the solid substrate. Labels may be directly detected through optical or electron density, radioactive emissions, nonradiative energy transfers, etc. or indirectly detected with antibody conjugates, streptavidin-biotin conjugates, etc. Methods for detecting the labels are well known in the art.

The monoclonal antibodies described herein can also be used to produce anti-idiotypic antibodies that can be used to screen and identify other antibodies having the same binding specificity as the monoclonal antibodies of the invention. An anti-idiotypic antibody is an antibody which recognizes unique determinants present on a monoclonal antibody of the invention. These determinants are located in the hypervariable region of the antibody. It is this region that binds to a given epitope and is thereby responsible for the specificity of the antibody. Such anti-idiotypic antibodies can be produced using well-known hybridoma techniques (Kohler and Milstein, *Nature,* 256:495, 1975). As an example, an anti-idiotypic antibody can be prepared by immunizing a subject with the monoclonal antibody. The immunized subject will recognize and respond to the idiotypic determinants of the immunizing monoclonal antibody and produce an antibody to these idiotypic determinants. By using the anti-idiotypic antibodies of the immunized animal, which are specific for the monoclonal antibody of the invention, it is possible to identify other clones with the same idiotype as the monoclonal antibody used for immunization. Idiotypic identity between monoclonal antibodies of two cell lines demonstrates that the two monoclonal antibodies are the same with respect to their recognition of the same epitopic determinant. Thus, by using anti-idiotypic antibodies, it is possible to identify other hybridomas expressing monoclonal antibodies having the same epitopic specificity. The invention intends to embrace all the fore-going antibody types.

The anti-idiotypic antibodies can also be used for active immunization (Herlyn, et al., *Science,* 232:100, 1986), since it is possible to use the anti-idiotype technology to produce monoclonal antibodies that mimic an epitope. For example, an anti-idiotypic monoclonal antibody made to a first monoclonal antibody will have a binding domain in the hypervariable region which is the image of the epitope bound by the first monoclonal antibody. Thus, the anti-idiotypic monoclonal antibody can be used for immunization, since the anti-idiotype monoclonal antibody binding domain effectively acts as an antigen.

The invention further contemplates bi-specific antibodies that include a first antigen-binding domain specific for PNAG/dPNAG and a second antigen binding domain specific for another moiety. The first antigen binding domain specific for PNAG/dPNAG may comprise any of the PNAG/dPNAG binding peptides (including CDRs, variable regions, Fab fragments described herein or produced or derived from deposited hybridomas having ATCC Accession Nos. PTA-5931, PTA-5932 and PTA-5933). The second antigen binding domain may be specific for a moiety on a cell such as a bacterial cell or a host cell. Host cells may be immune system cells or cells from the infected tissue. Antibodies for cell surface molecules expressed by immune system cells or from various host tissue cells are generally commercially available from sources such as Sigma or BD Biosciences Pharmingen. Those of ordinary skill in the art will be able to generate such bi-specific antibodies based on the teaching herein and the knowledge in the art. In a similar manner, the invention contemplates tri-specific antibodies also. (See, for example, U.S. Pat. Nos. 5,945,311 and 6,551,592 for bi-specific and tri-specific antibody generation.)

The sequences responsible for the specificity of the monoclonal antibodies of the invention have been determined. Accordingly, peptides according to the invention can be prepared using recombinant DNA technology. There are entities in the United States which will perform this function commercially, such as Thomas Jefferson University and the Scripps Protein and Nucleic Acids Core Sequencing Facility (La Jolla, Calif.). For example, the variable region cDNA can be prepared by polymerase chain reaction from the deposited hybridoma RNA using degenerate or non-degenerate primers (derived from the amino acid sequence). The cDNA can be subcloned to produce sufficient quantities of double stranded DNA for sequencing by conventional sequencing reactions or equipment.

With knowledge of the nucleic acid sequences of the heavy chain and light chain variable domains of the anti-Staphylococcal PNAG/dPNAG monoclonal antibody, one of ordinary skill in the art is able to produce nucleic acids which encode this antibody or which encode the various antibody fragments, humanized antibodies, or polypeptides described above. It is contemplated that such nucleic acids will be operably joined to other nucleic acids forming a recombinant vector for cloning or for expression of the peptides of the invention. The present invention includes any recombinant vector containing the coding sequences, or part thereof, whether for prokaryotic or eukaryotic transformation, transfection or gene therapy. Such vectors may be prepared using conventional molecular biology techniques, known to those with skill in the art, and would comprise DNA coding sequences for the CDR region (and preferably the CDR3 region) and additional variable sequences contributing to the specificity of the antibodies or parts thereof, as well as other non-specific peptide sequences and a suitable promoter either with (Whittle et al., *Protein Eng.* 1:499, 1987 and Burton et al., *Science* 266:1024-1027, 1994) or without (Marasco et al., *Proc. Natl. Acad. Sci.* (*USA*) 90:7889, 1993 and Duan et al., *Proc. Natl. Acad. Sci.* (*USA*) 91:5075-5079, 1994) a signal sequence for export or secretion. Such vectors may be transformed or transfected into prokaryotic (Huse et al., *Science* 246:1275, 1989, Ward et al., *Nature* 341: 644-646, 1989; Marks et al., *J. Mol. Biol.* 222:581, 1991 and Barbas et al., *Proc. Natl. Acad. Sci.* (*USA*) 88:7978, 991) or eukaryotic (Whittle et al., 1987 and Burton et al., 1994) cells or used for gene therapy (Marasco et al., 1993 and Duan et al., 1994) by conventional techniques, known to those with skill in the art.

As used herein, a "vector" may be any of a number of nucleic acids into which a desired sequence may be inserted by restriction and ligation for transport between different genetic environments or for expression in a host cell. Vectors are typically composed of DNA although RNA vectors are also available. Vectors include, but are not limited to, plasmids and phagemids. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase. An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase or alkaline phosphatase), and genes which visibly affect the phenotype of transformed or transfected cells, hosts, colonies or plaques. Preferred vectors are those capable of autonomous replication and expression of the structural gene products present in the DNA segments to which they are operably joined.

The expression vectors of the present invention include regulatory sequences operably joined to a nucleotide sequence encoding one of the peptides of the invention. As used herein, the term "regulatory sequences" means nucleotide sequences which are necessary for, or conducive to, the transcription of a nucleotide sequence which encodes a desired polypeptide and/or which are necessary for or conducive to the translation of the resulting transcript into the desired polypeptide. Regulatory sequences include, but are not limited to, 5' sequences such as operators, promoters and ribosome binding sequences, and 3' sequences such as polyadenylation signals. The vectors of the invention may optionally include 5' leader or signal sequences, 5' or 3' sequences encoding fusion products to aid in protein purification, and various markers which aid in the identification or selection of transformants. The choice and design of an appropriate vector is within the ability and discretion of one of ordinary skill in the art. The subsequent purification of the peptides may be accomplished by any of a variety of standard means known in the art.

A preferred vector for screening peptides, but not necessarily preferred for the mass production of the peptides of the invention, is a recombinant DNA molecule containing a nucleotide sequence that codes for and is capable of expressing a fusion polypeptide containing, in the direction of amino- to carboxy-terminus, (1) a prokaryotic secretion signal domain, (2) a polypeptide of the invention, and, optionally, (3) a fusion protein domain. The vector includes DNA regulatory sequences for expressing the fusion polypeptide, preferably prokaryotic regulatory sequences. Such vectors can be constructed by those with skill in the art and have been described by Smith et al. (*Science* 228:1315-1317, 1985), Clackson et al. (*Nature* 352:624-628, 1991); Kang et al. (in "Methods: A Companion to Methods in Enzymology: Vol. 2", R. A. Lerner and D. R. Burton, ed. Academic Press, NY, pp 111-118, 1991); Barbas et al. (*Proc. Natl. Acad. Sci.* (*USA*) 88:7978-7982, 1991), Roberts et al. (*Proc. Natl. Acad. Sci.* (*USA*) 89:2429-2433, 1992)

A fusion polypeptide may be useful for purification of the peptides of the invention. The fusion domain may, for example, include a poly-His tail which allows for purification on Ni+ columns or the maltose binding protein of the commercially available vector pMAL (New England BioLabs, Beverly, Mass.). A currently preferred, but by no means necessary, fusion domain is a filamentous phage membrane anchor. This domain is particularly useful for screening phage display libraries of monoclonal antibodies but may be of less utility for the mass production of antibodies. The filamentous phage membrane anchor is preferably a domain of the cpIII or cpVIII coat protein capable of associating with the matrix of a filamentous phage particle, thereby incorporating the fusion polypeptide onto the phage surface, to enable solid phase binding to specific antigens or epitopes and thereby allow enrichment and selection of the specific antibodies or fragments encoded by the phagemid vector.

The secretion signal is a leader peptide domain of a protein that targets the protein membrane of the host cell, such as the periplasmic membrane of gram negative bacteria. A preferred secretion signal for *E. coli* is a pelB secretion signal. The predicted amino acid residue sequences of the secretion signal domain from two pelB gene producing variants from *Erwinia carotova* are described in Lei, et al. (*Nature* 381:543-546, 1988). The leader sequence of the pelB protein has previously been used as a secretion signal for fusion proteins (Better, et al., *Science* 240:1041-1043, 1988; Sastry, et al., *Proc. Natl. Acad. Sci* (*USA*) 86:5728-5732, 1989; and Mullinax, et al., *Proc. Natl. Acad. Sci.* (*USA*) 87:8095-8099, 1990). Amino acid residue sequences for other secretion signal polypeptide domains from *E. coli* useful in this invention can be found in Oliver, In Neidhard, F. C. (ed.), *Escherichia coli* and *Salmonella Typhimurium*, American Society for Microbiology, Washington, D.C., 1:56-69 (1987).

To achieve high levels of gene expression in *E. coli*, it is necessary to use not only strong promoters to generate large quantities of mRNA, but also ribosome binding sites to ensure that the mRNA is efficiently translated. In *E. coli*, the ribosome binding site includes an initiation codon (AUG) and a sequence 3-9 nucleotides long located 3-11 nucleotides upstream from the initiation codon (Shine, et al., *Nature* 254:34, 1975). The sequence, AGGAGGU, which is called the Shine-Dalgarno (SD) sequence, is complementary to the 3' end of *E. coli* 16S rRNA. Binding of the ribosome to mRNA and the sequence at the 3' end of the mRNA can be affected by several factors: (i) the degree of complementarity between the SD sequence and 3' end of the 16S rRNA; (ii) the spacing and possibly the DNA sequence lying between the SD sequence and the AUG (Roberts, et al., *Proc. Natl. Acad. Sci.* (*USA*) 76:760, 1979a: Roberts, et al., *Proc. Natl. Acad. Sci.* (*USA*) 76:5596, 1979b; Guarente, et al., *Science* 209:1428, 1980; and Guarente, et al., *Cell* 20:543, 1980). Optimization is achieved by measuring the level of expression of genes in plasmids in which this spacing is systematically altered. Comparison of different mRNAs shows that there are statistically preferred sequences from positions −20 to +13 (where the A of the AUG is position 0) (Gold, et al., *Annu. Rev. Microbiol.* 35:365, 1981). Leader sequences have been shown to influence translation dramatically (Roberts, et al., 1979a, b supra); and (iii) the nucleotide sequence following the AUG, which affects ribosome binding (Taniguchi, et al., *J. Mol. Biol.*, 118:533, 1978).

The 3' regulatory sequences define at least one termination (stop) codon in frame with and operably joined to the heterologous fusion polypeptide.

In preferred embodiments with a prokaryotic expression host, the vector utilized includes a prokaryotic origin of replication or replicon, i.e., a DNA sequence having the ability to direct autonomous replication and maintenance of the recombinant DNA molecule extra-chromosomally in a prokaryotic host cell, such as a bacterial host cell, transformed therewith. Such origins of replication are well known in the art. Preferred origins of replication are those that are efficient in the host organism. A preferred host cell is *E. coli*. For use of a vector in *E. coli*, a preferred origin of replication is ColE1 found in pBR322 and a variety of other common plasmids. Also preferred is the p15A origin of replication found on pACYC and its derivatives. The ColE1 and p15A replicons have been extensively utilized in molecular biology, are available on a variety of plasmids and are described by Sambrook. et al., *Molecular Cloning: A Laboratory Manual,* 2nd edition, Cold Spring Harbor Laboratory Press, 1989).

In addition, those embodiments that include a prokaryotic replicon preferably also include a gene whose expression confers a selective advantage, such as drug resistance, to a bacterial host transformed therewith. Typical bacterial drug resistance genes are those that confer resistance to ampicillin, tetracycline, neomycin/kanamycin or chloramphenicol. Vectors typically also contain convenient restriction sites for insertion of translatable DNA sequences. Exemplary vectors are the plasmids pUC18 and pUC19 and derived vectors such as pcDNAII available from Invitrogen (San Diego, Calif.).

When the peptide of the invention is an antibody including both heavy chain and light chain sequences, these sequences may be encoded on separate vectors or, more conveniently, may be expressed by a single vector. The heavy and light chain may, after translation or after secretion, form the heterodimeric structure of natural antibody molecules. Such a heterodimeric antibody may or may not be stabilized by disulfide bonds between the heavy and light chains.

A vector for expression of heterodimeric antibodies, such as the intact antibodies of the invention or the F(ab')$_2$, Fab or Fv fragment antibodies of the invention, is a recombinant DNA molecule adapted for receiving and expressing translatable first and second DNA sequences. That is, a DNA expression vector for expressing a heterodimeric antibody provides a system for independently cloning (inserting) the two translatable DNA sequences into two separate cassettes present in the vector, to form two separate cistrons for expressing the first and second polypeptides of a heterodimeric antibody. The DNA expression vector for expressing two cistrons is referred to as a dicistronic expression vector.

Preferably, the vector comprises a first cassette that includes upstream and downstream DNA regulatory sequences operably joined via a sequence of nucleotides adapted for directional ligation to an insert DNA. The upstream translatable sequence preferably encodes the secretion signal as described above. The cassette includes DNA regulatory sequences for expressing the first antibody polypeptide that is produced when an insert translatable DNA sequence (insert DNA) is directionally inserted into the cassette via the sequence of nucleotides adapted for directional ligation.

The dicistronic expression vector also contains a second cassette for expressing the second antibody polypeptide. The second cassette includes a second translatable DNA sequence that preferably encodes a secretion signal, as described above, operably joined at its 3' terminus via a sequence of nucleotides adapted for directional ligation to a downstream DNA sequence of the vector that typically defines at least one stop codon in the reading frame of the cassette. The second translatable DNA sequence is operably joined at its 5' terminus to DNA regulatory sequences forming the 5' elements. The second cassette is capable, upon insertion of a translatable DNA sequence (insert DNA), of expressing the second fusion polypeptide comprising a secretion signal with a polypeptide coded by the insert DNA.

The peptides of the present invention may also be produced by eukaryotic cells such as CHO cells, human hybridomas, immortalized B-lymphoblastoid cells, and the like. In this case, a vector is constructed in which eukaryotic regulatory sequences are operably joined to the nucleotide sequences encoding the peptide. The design and selection of an appropriate eukaryotic vector is within the ability and discretion of one of ordinary skill in the art. The subsequent purification of the peptides may be accomplished by any of a variety of standard means known in the art.

In another embodiment, the present invention provides host cells, both prokaryotic and eukaryotic, transformed or transfected with, and therefore including, the vectors of the present invention.

As used herein with respect to nucleic acids, the term "isolated" means: (i) amplified in vitro by, for example, polymerase chain reaction (PCR); (ii) recombinantly produced by cloning; (iii) purified, as by cleavage and gel separation; or (iv) synthesized by, for example, chemical synthesis. An isolated nucleic acid is one which is readily manipulable by recombinant DNA techniques well known in the art. Thus, a nucleotide sequence contained in a vector in which 5' and 3' restriction sites are known or for which polymerase chain reaction (PCR) primer sequences have been disclosed is considered isolated but a nucleic acid sequence existing in its native state in its natural host is not. An isolated nucleic acid may be substantially purified, but need not be. For example, a nucleic acid that is isolated within a cloning or expression vector is not pure in that it may comprise only a tiny percentage of the material in the cell in which it resides. Such a nucleic acid is isolated, however, as the term is used herein because it is readily manipulable by standard techniques known to those of ordinary skill in the art.

As used herein, a coding sequence and regulatory sequences are said to be "operably joined" when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribing and 5' non-translating sequences involved with initiation of transcription and translation respectively, such as a TATA box, capping sequence, CAAT sequence, and the like. Especially, such 5' non-transcribing regulatory sequences will include a promoter region which includes a promoter sequence for transcriptional control of the operably joined gene. Regulatory sequences may also include enhancer sequences or upstream activator sequences, as desired.

The invention also intends to embrace the use of the peptides described herein in in vivo and in vitro methods. The methods of the invention are useful for diagnosing as well as treating infections by PNAG-expressing bacteria such as Staphylococcal infections. "Staphylococci" as used herein refers to all Staphylococcal bacterial species expressing the PNAG antigen. Bacteria that are classified as Staphylococci are well known to those of skill in the art and are described in the microbiology literature. Staphylococci expressing PNAG include but are not limited to *Staphylococcus epidermidis* (including RP62A (ATCC Number 35984), RP12 (ATCC Number 35983), and M187), *Staphylococcus aureus* (including RN4220 (pCN27) and MN8 mucoid), and strains such as *Staphylococcus carnosus* transformed with the genes in the ica locus (including TM300 (pCN27)). Other bacterial strains expressing PNAG naturally carry or are transformed with the pga locus. Examples include *E. coli*, *Yersinia pestis* (*Y. pestis*), *Y. entercolitica*, *Xanthomonas axonopodis*, *Pseudomonas fluorescens* (all of which are sequenced species with complete pgaABCD loci), and *Actinobacillus actinomycetemcomitans* (*A. actinomycetemcomitans*), *A. pleuropneumoniae*, *Ralstonia solanacearum* (e.g., megaplasmid form), *Bordetella pertussis* (*B. pertussis*), *B. parapertussis* and *B. bronchiseptica*. Other bacterial strains expressing PNAG can be identified easily by those of ordinary skill in the art. For instance, bacteria that carry the ica or pga locus can produce PNAG. One of ordinary skill in the art can easily screen for the expression of mRNA or protein related to the ica or pga locus since the nucleic acid sequences of the ica and pga locus are known (described in Heilmann, C., O. Schweitzer, C. Gerke, N. Vanittanakom, D. Mack and F. Gotz (1996) Molecular basis of intercellular adhesion in the biofilm-forming *Staphylococcus epidermidis*. Molec. Microbiol. 20:1083 for *S. epidermidis* and in Cramton S E, Gerke C, Schnell N F, Nichols W W, Gotz F. The intercellular adhesion (ica) locus is present in *Staphylococcus aureus* and is required for biofilm formation. Infect Immun. 1999 October; 67(10):5427-33) for *S. aureus*; Blattner, F. R., G. Plunkett III, C. A. Bloch, N. T. Perna, V. Burland, M. Riley, J. Collado-Vides, J. D. Glasner, C. K. Rode, G. F. Mayhew, J. Gregor, N. W. Davis, H. A. Kirkpatrick, M. A. Goeden, D. J. Rose, B. Mau, and Y. Shao. 1997. The complete genome sequence of *Escherichia coli* K-12. Science 277:1453-1474. The genes reported by Blattner et al. were designated ycdSRQP in and renamed pgaABCD in Wang et al., J. Bacteriology, May 2004, p. 2724-2734, Vol. 186, No. 9.) Additionally the capsule of bacterial strains can be isolated and analyzed using liquid chromatography and mass spectroscopy.

The detection or diagnosis methods provided by the invention generally involve contacting one or more peptides of the invention with a sample in or from a subject. Preferably, the sample is first harvested from the subject, although in vivo detection methods are also envisioned. The sample may include any body tissue or fluid that is suspected of harboring the bacteria. For example, a Staphylococcal infection can occur in essentially all tissues, organs and fluids of the human body but are most commonly found infecting the skin, bones, joints lungs and blood. An *E. coli* infection can occur, for example, in the genito-urinary tract, as well as other tissues and locations. *Y. pestis* infection is the cause of bubonic plague in the skin and pneumonic plague in the lung. *B. pertussis* infection causes whopping cough in the respiratory tract. Essentially any bodily fluid, tissue or organ such as skin, bone, joints, lungs, mucous such as phlegm and blood can be tested for the presence of the bacteria.

As used herein, the term "treatment" refers to the administration of peptides to a subject for the purpose of achieving a medically desirable benefit. Accordingly, "treatment" intends to embrace both "prophylactic" and "therapeutic" treatment methods. Prophylactic treatment methods refer to treatment administered to a subject prior to the diagnosis of an infection (such as a Staphylococcal infection). In other words, the subject does not present with symptoms of an infection (such as a Staphylococcal infection) although the subject may be at risk thereof. Therapeutic treatment methods refer to treatment administered to a subject after the diagnosis of an infection (such as a Staphylococcal infection). In other words, the subject has been diagnosed as having an infection (such as a Staphylococcal infection) or alternatively, the subject may exhibit symptoms associated with such an infection.

The anti-PNAG/dPNAG antibodies of the invention are useful for inducing passive immunization in a subject to prevent or limit the development of systemic infection and disease in those subjects at risk of exposure to infectious agents. The method for inducing passive immunity to infection by PNAG-expressing bacteria, such as Staphylococci such as *S. aureus*, is performed by administering to a subject an effective amount of an anti-PNAG/dPNAG antibody (e.g., one that causes opsonization of Staphylococci such as *S. aureus*). "Passive immunity" as used herein involves the administration of antibodies to a subject, wherein the antibodies are produced in a different subject (including subjects of the same and different species), such that the antibodies attach to the surface of the bacteria and cause the bacteria to be phagocytosed.

The anti-PNAG/dPNAG antibody may be administered to any subject at risk of developing an infection by bacteria that express PNAG (e.g., PNAG-expressing Staphylococcal infection) to induce passive immunity, and in some embodiments may be particularly suited for subjects incapable of inducing active immunity to PNAG and/or dPNAG. A subject that is incapable of inducing an immune response is an immunocompromised subject (e.g. patient undergoing chemotherapy, AIDS patient, etc.) or a subject that has not yet developed an immune system (e.g. pre-term neonate).

A "subject" as used herein is a warm-blooded mammal and includes but is not limited to humans, primates, agricultural animals such as horses, cows, swine, goats, sheep and chicken, and domestic animals such as dogs and cats. In some embodiments, the subject is a non-rodent subject. A non-rodent subject is any subject as defined above, but specifically excluding rodents such as mice, rats, and rabbits. In some embodiments, the preferred subject is a human. In some instances, the subject may be one that has or will receive a prosthesis such as a hip or knee replacement since such devices are especially prone to colonization by bacteria. As stated herein, some aspects of the invention provide for detection and treatment of infections in plants also.

The anti-PNAG/dPNAG antibody of the invention is administered to the subject in an effective amount for inducing immunity to PNAG-expressing bacteria (e.g., Staphylococci such as *S. aureus*). An "effective amount for inducing immunity to PNAG-expressing bacteria" is an amount of anti-PNAG/dPNAG antibody that is sufficient to (i) prevent infection by such bacteria from occurring in a subject that is exposed to such bacteria; (ii) inhibit the development of infection, i.e., arresting or slowing its development; and/or (iii) relieve the effects of the infection, i.e., reduction in bacterial load or complete eradication of the bacteria in infected subjects. As an example, an "effective amount for inducing immunity to Staphylococci" as used herein is an amount of anti-PNAG/dPNAG antibody that is sufficient to (i) prevent infection by Staphylococci from occurring in a subject that is exposed to Staphylococci; (ii) inhibit the development of infection, i.e., arresting or slowing its development; and/or (iii) relieve the effects of the infection, i.e., reduction in bacterial load or complete eradication of the bacteria in infected subjects.

Using routine procedures known to those of ordinary skill in the art, one can determine whether an amount of anti-PNAG/dPNAG antibody is an "effective amount for inducing immunity to infection" by using an in vitro opsonization assay which is predictive of the degree of opsonization of an antibody. An antibody that opsonizes PNAG-expressing bacteria such as PNAG-expressing Staphylococcal bacteria is one that when added to a sample of such bacteria causes phagocytosis of the bacteria. An opsonization assay may be a colorimetric assay, a chemiluminescent assay, a fluorescent or radiolabel uptake assay, a cell mediated bactericidal assay or other assay which measures the opsonic potential of a material.

Antibody doses ranging from 1 ng/kg to 100 mg/kg, depending upon the mode of administration, will be effective. The preferred range is believed to be between 500 ng and 500 µg/kg, and most preferably between 1-100 µg/kg. The absolute amount will depend upon a variety of factors including whether the administration is performed on a high risk subject not yet infected with the bacteria or on a subject already having an infection, the concurrent treatment, the number of doses and the individual patient parameters including age, physical condition, size and weight. These are factors well known to those of ordinary skill in the art and can be addressed with no more than routine experimentation. It is preferred generally that a maximum dose be used, that is, the highest safe dose according to sound medical judgment.

Multiple doses of the antibodies of the invention are also contemplated. Generally immunization schemes involve the administration of a high dose of an antibody followed by subsequent lower doses of antibody after a waiting period of several weeks. Further doses may be administered as well. The dosage schedule for passive immunization may require more frequent administration. Desired time intervals for delivery of multiple doses of a particular PNAG/dPNAG antibody can be determined by one of ordinary skill in the art employing no more than routine experimentation.

A variety of administration routes are available. The particular mode selected will depend, of course, upon the particular anti-PNAG/dPNAG antibody selected, the particular condition being treated and the dosage required for therapeutic efficacy. The methods of this invention, generally speaking, may be practiced using any mode of administration that is medically acceptable, meaning any mode that produces effective levels of protection without causing clinically unacceptable adverse effects. Preferred modes of administration are parenteral routes. The term "parenteral" includes subcutaneous, intravenous, intramuscular, intraperitoneal, and intrasternal injection, or infusion techniques. Other routes include but are not limited to oral, nasal, dermal, sublingual, and local.

The anti-PNAG/dPNAG antibodies of the invention may be delivered in conjunction with other anti-bacterial drugs (e.g., antibiotics) or with other anti-bacterial antibodies. The use of antibiotics in the treatment of bacterial infection is routine. A common administration vehicle (e.g., tablet, implant, injectable solution, etc.) may contain both the antibody of the invention and the anti-bacterial drug and/or antibody. Alternatively, the anti-bacterial drug and/or antibody can be separately dosed. The anti-bacterial drug or antibody can also be conjugated to the anti-PNAG/dPNAG antibody.

Anti-bacterial drugs are well known and include: penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefinenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's, Pharmacological Basics of Therapeutics, 8th Ed., 1993, McGraw Hill Inc.).

According to the methods of the invention, the peptide may be administered in a pharmaceutical composition. In general, a pharmaceutical composition comprises the peptide of the invention and a pharmaceutically-acceptable carrier. Pharmaceutically-acceptable carriers for peptides, monoclonal antibodies, and antibody fragments are well-known to those of ordinary skill in the art. As used herein, a pharmaceutically-acceptable carrier means a non-toxic material that does not interfere with the effectiveness of the biological activity of the active ingredients, e.g., the ability of the peptide to bind to Staphylococcal PNAG and/or dPNAG and optionally to enhance opsonization and phagocytosis.

Pharmaceutically acceptable carriers include diluents, fillers, salts, buffers, stabilizers, solubilizers and other materials which are well-known in the art. Exemplary pharmaceutically acceptable carriers for peptides in particular are described in U.S. Pat. No. 5,211,657. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The peptides of the invention may be formulated into preparations in solid, semi-solid, liquid or gaseous forms such as tablets, capsules, powders, granules, ointments, solutions, depositories, inhalants and injections, and usual ways for oral, parenteral or surgical administration. The invention also embraces pharmaceutical compositions which are formulated for local administration, such as by implants.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

When the compounds described herein (including peptide and non-peptide varieties) are used therapeutically, in certain embodiments a desirable route of administration may be by pulmonary aerosol. Techniques for preparing aerosol delivery systems containing compounds are well known to those of skill in the art. Generally, such systems should utilize components which will not significantly impair the biological properties of the peptides (see, for example, Sciarra and Cutie, "Aerosols," in *Remington's Pharmaceutical Sciences*, 18th edition, 1990, pp 1694-1712; incorporated by reference). Those of skill in the art can readily determine the various parameters and conditions for producing aerosols without resort to undue experimentation.

The methods of the invention also encompass the step of administering the peptides of the invention in conjunction with conventional therapies for treating the underlying bacterial infection. For example, the method of the invention may be practiced simultaneously with a conventional treatment, such as for example antibiotic therapy. In some embodiments, the peptides may be administered substantially simultaneously with the conventional treatment. By substantially simultaneously, it is meant that a peptide of the invention is administered to a subject close enough in time with the administration of the conventional treatment (e.g., antibiotic), whereby the two compounds may exert an additive or even synergistic effect. In some instances, the peptide and the agent of the conventional treatment are conjugated to each other. In others, the compounds are physically separate.

The peptides of the invention may be administered directly to a tissue. Preferably, the tissue is one in which the bacterial infection exists. Alternatively, the tissue is one in which the infection is likely to arise. Direct tissue administration may be achieved by direct injection. The peptides may be administered once, or alternatively they may be administered in a plurality of administrations. If administered multiple times, the peptides may be administered via different routes. For example, the first (or the first few) administrations may be made directly into the affected tissue while later administrations may be systemic.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day are contemplated to achieve appropriate systemic levels of compounds.

In yet other embodiments, the preferred vehicle is a biocompatible microparticle or implant that is suitable for implantation into the mammalian recipient. Exemplary bioerodible implants that are useful in accordance with this method are described in PCT International Application No. PCT/US/03307 (Publication No. WO 95/24929, entitled "Polymeric Gene Delivery System", claiming priority to U.S. patent application Ser. No. 213,668, filed Mar. 15, 1994). PCT/US/0307 describes a biocompatible, preferably biodegradable polymeric matrix for containing a biological macromolecule. The polymeric matrix may be used to achieve sustained release of the agent in a subject. In accordance with one aspect of the instant invention, the agent described herein may be encapsulated or dispersed within the biocompatible, preferably biodegradable polymeric matrix disclosed in PCT/US/03307. The polymeric matrix preferably is in the form of a microparticle such as a microsphere (wherein the agent is dispersed throughout a solid polymeric matrix) or a microcapsule (wherein the agent is stored in the core of a polymeric shell). Other forms of the polymeric matrix for containing the agent include films, coatings, gels, implants, and stents. The size and composition of the polymeric matrix device is selected to result in favorable release kinetics in the tissue into which the matrix device is implanted. The size of the polymeric matrix device further is selected according to the method of delivery which is to be used, typically injection into a tissue or administration of a suspension by aerosol into the nasal and/or pulmonary areas. The polymeric matrix composition can be selected to have both favorable degradation rates and also to be formed of a material which is bioadhesive, to further increase the effectiveness of transfer when the device is administered to a vascular, pulmonary, or other surface. The matrix composition also can be selected not to degrade, but rather, to release by diffusion over an extended period of time.

Both non-biodegradable and biodegradable polymeric matrices can be used to deliver the agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multivalent ions or other polymers.

In general, the agents of the invention may be delivered using the bioerodible implant by way of diffusion, or more preferably, by degradation of the polymeric matrix. Exemplary synthetic polymers which can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, poly-vinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly(ethyl methacrylate), poly (butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly (octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein, polyhyaluronic acids, casein, gelatin, glutin, polyanhydrides, polyacrylic acid, alginate, chitosan, poly(methyl methacrylates), poly (ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

Other delivery systems can include time-release, delayed release or sustained release delivery systems. Such systems can avoid repeated administrations of the peptide, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the platelet reducing agent is contained in a form within a matrix such as those described in U.S. Pat. Nos. 4,452,775, 4,675,189, and 5,736,152 and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

Use of a long-term sustained release implant may be particularly suitable for prophylactic treatment of subjects at risk of developing an infection such as a Staphylococcal infection. Long-term release, as used herein, means that the implant is constructed and arranged to delivery therapeutic levels of the active ingredient for at least 30 days, and preferably 60 days. Long-term sustained release implants are well-known to those of ordinary skill in the art and include some of the release systems described above.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

*S. aureus* and *S. epidermidis* are associated with a wide range of hospital and community acquired infections. The rise of antibiotic resistance drives the development of new therapies to treat and prevent these infections. Adhesion of the bacteria to host tissues or to implanted prosthetic devices is often important for a successful Staphylococcal infection. One such adhesion molecule expressed on the surface of Staphylococci in vivo and found to be a target of protective antibodies is poly-N acetyl-glucosamine (PNAG). This adhesion molecule is expressed and employed by other bacteria such as but not limited to *E. coli*.

Experimental Procedures

Hybridomas:

Blood was collected from patients after the onset of *S. aureus* infection and peripheral blood mononuclear cells (PBMC) were isolated from the blood samples using Ficoll Hypaque sedimentation. B cells were stimulated by overnight exposure to Epstein-Barr virus (EBV) produced from the B95.8 cell line as described by Posner et al. (Posner et al. Epstein Barr virus transformation of peripheral blood B cells secreting antibodies reactive with cell surface antigens. Autoimmunity. 1990; 8(2):149-58.) After 24 hours, the cells were washed and dispersed into 96 well plates at a concentration of $1 \times 10^6$ PBMC/well in 100 µl of growth media (RPMI1640 supplemented with 20% FBS) containing 10% Lymphocyte Conditioned Medium (LyCM, prepared from human PBMC stimulated for 48 hours with phytohemagglutinin). After 5 days, an additional 100 µl of growth media supplemented with 10% LyCM was added. EBV stimulated cells were then fed weekly by removal of 100 µl of spent media and the addition of 100 µl of growth media supplemented with 10% LyCM.

When the wells were densely seeded (as evidenced by growth over 80% of the bottom of the well surface and the appearance of a pH change in the media indicative of cellular growth), the cultures were screened for production of specific antibody to PNAG/dPNAG by ELISA. The cells from single individual wells giving a positive reaction for antibody were then dispersed into 48 wells of a tissue culture plate and after several days of growth the supernates tested for reactivity with PNAG/dPNAG antigen.

Cultures that continued to test positive by ELISA were then fused with the human-mouse myeloma cell line HMMA 2.5 to generate hybridomas as previously described (Posner et al. The construction and use of a human-mouse myeloma analogue suitable for the routine production of hybridomas secreting human monoclonal antibodies. Hybridoma. 1987 December; 6(6):611-25). After fusion, cells were cultured in microwell plates with growth medium (RPMI 1640 supplemented with 20% FBS and hypoxanthine-aminopterin-thymidine (HAT) and oubain) for selection of fused cells. These cultures were fed at weekly intervals and screened by ELISA for antibody production.

Hybridomas were cloned at a density of 1 cell/well, wells with positive growth screened by ELISA for specific antibody, and wells containing positive antibody-producing hybridomas expanded into wells in tissue culture plates of increasing volume, then flasks of increasing volume to obtain cloned cell lines. Three hybridomas, designated F598, F628 and F630, producing human IgG2 antibodies that bound to either PNAG, dPNAG or both were recovered.

Chemical Modification of PNAG:

To remove the majority of the N- and O-substituents, purified PNAG was dissolved in 5M NaOH to a final concentration of 0.5 mg/ml and incubated for 18 hr at 37° C. with stirring. The strong base solution was then neutralized with 5N HCl, to a final pH between 6 and 8, and dialyzed against $dH_2O$ for 24 hrs. The final product was obtained by freeze drying the sample.

ELISAs:

Immulon 4 microtiter plates were coated with 100 µl of the optimal binding concentration of each antigen (0.6 µg/ml for native PNAG and 3 µg/ml for dPNAG) in sensitizing buffer (0.2M $NaH_2PO_4$, 0.2M $Na_2HPO_4$, 0.02% azide) and incubated overnight at 4° C. Plates were washed 3× with PBS/0.05% tween and blocked with 200 µl of 5% skim milk in PBS, and then incubated overnight at 4° C. The plates were washed and purified MAbs were added at various concentrations, diluted in 5% skim milk/0.05% tween in PBS (dilution buffer). The plates were then incubated for 1 hr at 37° C. and washed. 100 µl of secondary antibody (anti-human IgG whole molecule-conjugated to alkaline phosphatase (AP) and obtained from ICN) was added at a 1:1000 dilution made in the dilution buffer. The plates were incubated at 37° C. for 1 hr and washed. 100 µl of p-Nitrophenyl Phosphate at a concentration of 1 mg/ml in substrate buffer (800 mg $NaHCO_3$, 1.46 g $Na_2CO_3$, 10 mg $MgCl$, 20 mg $Na_3N$ in 500 ml $H_2O$) was added and the plates were incubated at room temperature for 30 min. The plates were read at 405 nm. Purified human IgG from Sigma was used as a standard to quantify MAbs on plates sensitized with anti-human IgG.

Complement Deposition Assay:

Microtiter plates were prepared as for the ELISA assay. After incubation with the MAb and washing, normal human sera absorbed with three different *S. aureus* strains was used as a source of complement at a dilution of 1:50 in dilution buffer. The plates were incubated for 15 min at 37° C. After washing the plate, goat anti-human C3 antibody was added at a concentration of 1:2000 and incubated for one hour at 37° C. An anti goat IgG-AP conjugate was added at 1:2000 and incubated at 37° C. for one hour. The plates were developed essentially as for the ELISA assay, except only for a 15 min duration.

Opsonophagocytic Assays:

Opsonophagocytic killing assays have been described previously. (See Ames et al. Infection and Immunity 49:281-285, 1985 and Maira-Litran et al. Infect Immun. 70(8):4433-4440, 2002.) The target strain used is Mn8 (*S. aureus*). The target strain was grown to an optical density at a wavelength of 650 nm ($OD_{650}$) of 0.4 and diluted to 1:100 for the assay. Complement (obtained from an infant rabbit via a commercial source such as Accurate Chemical And Scientific Corp. Westbury, N.Y. 11590, and used at a 1:15 dilution) was absorbed for 1 hr with the Mn8m strain of *S. aureus* (resuspended to an $OD_{650}$ of 1.0). Polymorphonuclear cells (PMNs) were separated from freshly drawn human blood using Heparin/dextran (1:1 mix). PMNs were used at a concentration of $5 \times 10^6$ cells/ml. Solutions with the monoclonal antibodies at various concentrations are used as the antibody source. One hundred µl of each component (monoclonal antibody solution, PMNs, complement, target bacteria) were added together and then incubated for 1.5 hr at 37° C., while rotating. Supernates were taken and dilutions made and then aliquots plated on trypic soy agar (TSA), generally using supernate dilutions of 1:100 and 1:1000. After incubating overnight at 37° C., bacterial colonies were counted and levels of killing calculated.

Cloning of Antibody Variable Regions:

RNA extraction from each hybridoma was performed on $\sim 6 \times 10^6$ cells using the RNAeasy kit from Qiagen. 1 µg of total RNA was reverse transcribed into cDNA using a Qiagen Omniscript kit. 1 µl of cDNA product was used as a template for the PCR reactions. Each reaction consisted of 50 µl of Invitrogen Hi fi mix, 100 pmoles of each nucleotide primer and 1 µl of cDNA template. ~30 PCR cycles were performed with the following protocol: 94° C. for 30 sec, cycle: 94° C. for 30 sec, 65° C. for 30 sec, 72° C. for 1 min, final extension 72° C. for 5 min. PCR products were sequenced and searched using the Ig BLAST program against known germline sequences available on the NCBI database.

Primers used to clone antibody variable regions from the hybridoma cell lines deposited with the ATCC under Accession No. PTA-5931, PTA-5932 and PTA-5933 on Apr. 21, 2004, are as follows: (5'-3' with restriction sites underlined and starting ATGs in bold):

```
F598 light chain
lambda constant:      GACCGAGGGGGCAGCCTTGGGCTGACCTAGG    (SEQ ID NO: 49)
Hu lambda sig 5:      AGATCTCTCACCATGGCATGGATCCCTCTCTTC  (SEQ ID NO: 50)

F598 heavy chain
Heavy chain constant: TGGGCCCTTGGTGCTAGCTGAGGAGAC        (SEQ ID NO: 51)
VH7LDRHU:             GTCGACATGAAACATCTGTGGTTCTTC        (SEQ ID NO: 52)

F628 light chain
lambda constant:      GACCGAGGGGGCAGCCTTGGGCTGACCTAGG    (SEQ ID NO: 49)
Hu lambda sig 1:      AGATCTCTCACCATGGCCRGCTTCCCTCTCCTC  (SEQ ID NO: 53)

F628 heavy chain
Heavy chain constant: TGGGCCCTTGGTGCTAGCTGAGGAGAC        (SEQ ID NO: 51)
VH7LDRHU:             GTCGACATGAAACATCTGTGGTTCTTC        (SEQ ID NO: 52)

F630 light chain
lambda constant:      GACCGAGGGGGCAGCCTTGGGCTGACCTAGG    (SEQ ID NO: 49)
Hu lambda sig 5:      AGATCTCTCACCATGGCATGGATCCCTCTCTTC  (SEQ ID NO: 50)

F630 heavy chain
Heavy chain constant: TGGGCCCTTGGTGCTAGCTGAGGAGAC        (SEQ ID NO: 51)
VH1LDRHU:             GTCGACATGGACTGGACCTGGA             (SEQ ID NO: 54)
```

In Vivo Bacterial Challenge Assays:

Mice were intravenously (IV) administered MAb F598 which binds to both PNAG and dPNAG, or a control, non-PNAG/dPNAG binding human IgG1 MAb to *P. aeruginosa* alginate or MEP (designated MAb F429) to induce passive immunity. Twenty-four hours later, mice were challenged with *S. aureus* ($5 \times 10^7$ CFU/mouse) by the same route of administration as the MAb.

CFU levels in blood 2 hours after infection were used as the measure of efficacy of the MAb administered for inducing passive immunity against *S. aureus*.

Results

MAb Sequences:

The amino acid and nucleotide sequences for the variable regions and CDR of the MAbs F598, F628 and F630 are shown below. CDR regions are underlined and constant regions are italicized.

Ia. F598 HEAVY CHAIN VARIABLE REGION NUCLEOTIDE AND AMINO ACID SEQUENCE
ALIGNMENT

```
CAG GTG CAG CTG CAG GAG TCG GGC CCA GGA CTG GTG AAG CCT TCG    (SEQ ID NO: 25)
 Q   V   Q   L   Q   E   S   G   P   G   L   V   K   P   S    (SEQ ID NO: 1)

GAG ACC CTG TCC CTC ACC TGC ACT GTT TCT GGT GGC TCC ATC AGT
 E   T   L   S   L   T   C   T   V   S   G   G   S   I   S

GGT TAC TAC TGG AGT TGG ATC CGG CAG CCC CCA GGG AAG GGA CTG
 G   Y   Y   W   S   W   I   R   Q   P   P   G   K   G   L

GAG TGG ATT GGG TAT ATT CAT TAT AGT AGG AGC ACC AAC TCC AAC
 E   W   I   G   Y   I   H   Y   S   R   S   T   N   S   N

CCC GCC CTC AAG AGT CGA GTC ACC ATA TCA TCA GAC ACG TCC AAG
 P   A   L   K   S   R   V   T   I   S   S   D   T   S   K

AAC CAG CTC TCC CTG AGA CTG AGC TCA GTG ACC GCT GCG GAC ACG
 N   Q   L   S   L   R   L   S   S   V   T   A   A   D   T

GCC GTG TAT TAC TGT GCG AGA GAT ACC TAT TAC TAT GAT AGT GGT
 A   V   Y   Y   C   A   R   D   T   Y   Y   Y   D   S   G

GAT TAT GAG GAT GCT TTT GAT ATT TGG GGC CAA GGG ACA ATG GTC
 D   Y   E   D   A   F   D   I   W   G   Q   G   T   M   V

ACC GTC TCC TCA
 T   V   S   S
```

Ib. F598 HEAVY CHAIN VARIABLE REGION AMINO ACID SEQUENCE

QVQLQESGPGLVKPSETLSLTCTVSGGSISGYYWSWIRQPPGKGLEWIGYIHYSRSTNSNPA (SEQ ID NO: 1)
LKSRVTISSDTSKNQLSLRLSSVTAADTAVYYCARDTYYYDSGDYEDAFDIWGQGTMVTVSS

QVQLQESGPGLVKPSETLSLTCTVSGGSISGYYWSWIRQPPGKGLEWIGYIHYSRSTNSNPA (SEQ ID NO: 55)
LKSRVTISSDTSKNQLSLRLSSVTAADTAVYYCARDTYYYDSGDYEDAFDIWGQGTMVTVSS
AS

Ic. F598 HEAVY CHAIN VARIABLE REGION NUCLEOTIDE SEQUENCE

```
CAG GTG CAG CTG CAG GAG TCG GGC CCA GGA CTG GTG AAG CCT TCG    (SEQ ID NO: 25)
GAG ACC CTG TCC CTC ACC TGC ACT GTT TCT GGT GGC TCC ATC AGT
GGT TAC TAC TGG AGT TGG ATC CGG CAG CCC CCA GGG AAG GGA CTG
GAG TGG ATT GGG TAT ATT CAT TAT AGT AGG AGC ACC AAC TCC AAC
CCC GCC CTC AAG AGT CGA GTC ACC ATA TCA TCA GAC ACG TCC AAG
AAC CAG CTC TCC CTG AGA CTG AGC TCA GTG ACC GCT GCG GAC ACG
GCC GTG TAT TAC TGT GCG AGA GAT ACC TAT TAC TAT GAT AGT GGT
GAT TAT GAG GAT GCT TTT GAT ATT TGG GGC CAA GGG ACA ATG GTC
ACC GTC TCC TCA

CAG GTG CAG CTG CAG GAG TCG GGC CCA GGA CTG GTG AAG CCT TCG    (SEQ ID NO: 56)
GAG ACC CTG TCC CTC ACC TGC ACT GTT TCT GGT GGC TCC ATC AGT
GGT TAC TAC TGG AGT TGG ATC CGG CAG CCC CCA GGG AAG GGA CTG
GAG TGG ATT GGG TAT ATT CAT TAT AGT AGG AGC ACC AAC TCC AAC
CCC GCC CTC AAG AGT CGA GTC ACC ATA TCA TCA GAC ACG TCC AAG
AAC CAG CTC TCC CTG AGA CTG AGC TCA GTG ACC GCT GCG GAC ACG
GCC GTG TAT TAC TGT GCG AGA GAT ACC TAT TAC TAT GAT AGT GGT
GAT TAT GAG GAT GCT TTT GAT ATT TGG GGC CAA GGG ACA ATG GTC
ACC GTC TCC TCA GCT AGC
```

IIa. F598 LIGHT CHAIN VARIABLE REGION AMINO ACID AND NUCLEOTIDE SEQUENCE
ALIGNMENT

```
CAG CTT GTG CTG ACT CAG TCG CCC TCT GCC TCT GCC TCC CTG GGA    (SEQ ID NO: 26)
 Q   L   V   L   T   Q   S   P   S   A   S   A   S   L   G    (SEQ ID NO: 2)

GCC TCG GTC AAG CTC ACC TGC ACT CTG AGC AGT GGC CAC AGC AAC
 A   S   V   K   L   T   C   T   L   S   S   G   H   S   N

TAC GCC ATC GCT TGG CAT CAG CAG CAG CCA GGG AAG GGC CCT CGC
 Y   A   I   A   W   H   Q   Q   Q   P   G   K   G   P   R

TAC TTG ATG AAG GTT AAC AGA GAT GGC AGC CAC ATC AGG GGG GAC
 Y   L   M   K   V   N   R   D   G   S   H   I   R   G   D

GGG ATC CCT GAT CGC TTC TCA GGC TCC ACC TCT GGG GCT GAG CGT
 G   I   P   D   R   F   S   G   S   T   S   G   A   E   R

TAC CTC ACC ATC TCC AGT CTC CAG TCT GAA GAT GAG GCT GAC TAT
 Y   L   T   I   S   S   L   Q   S   E   D   E   A   D   Y

TAC TGT CAG ACC TGG GGC GCT GGC ATT CGA GTG TTC GGC GGA GGG
 Y   C   Q   T   W   G   A   G   I   R   V   F   G   G   G
```

```
ACC AAG CTG ACC GTC CTA GGT
 T   K   L   T   V   L   G
```

IIb. F598 LIGHT CHAIN VARIABLE REGION AMINO ACID SEQUENCE
QLVLTQSPSASASLGASVKLTCTLSSGHSNYAIAWHQQQPGKGPRYLMKVNRDGSHIRGDGI    (SEQ ID NO: 2)
PDRFSGSTSGAERYLTISSLQSEDEA DYYCQTWGAGIRVFGGGTKLTVLG

QLVLTQSPSASASLGASVKLTCTLSSGHSNYAIAWHQQQPGKGPRYLMKVNRDGSHIRGDGI    (SEQ ID NO: 57)
PDRFSGSTSGAERYLTISSLQSEDEA DYYCQTWGAGIRVFGGGTKLTVLG*QPKAAPSV*

IIc. F598 LIGHT CHAIN VARIABLE REGION NUCLEOTIDE SEQUENCE
```
CAG CTT GTG ACT CAG TCG CCC TCT GCC TCT GCC TCC CTG GGA    (SEQ ID NO: 26)
GCC TCG GTC AAG CTC ACC TGC ACT CTG AGC AGT GGC CAC AGC AAC
TAC GCC ATC GCT TGG CAT CAG CAG CAG CCA GGG AAG GGC CCT CGC
TAC TTG ATG AAG GTT AAC AGA GAT GGC AGC CAC ATC AGG GGG GAC
GGG ATC CCT GAT CGC TTC TCA GGC TCC ACC TCT GGG GCT GAG CGT
TAC CTC ACC ATC TCC AGT CTC CAG TCT GAA GAT GAG GCT GAC TAT
TAC TGT CAG ACC TGG GGC GCT GGC ATT CGA GTG TTC GGC GGA GGG
ACC AAG CTG ACC GTC CTA GGT
```

IIIa. F628 HEAVY CHAIN VARIABLE REGION AMINO ACID AND NUCLEOTIDE SEQUENCE
ALIGNMENT
```
CAG GTG CAG CTG CAG GAG TCG GGC CCA GGA CTG GTG AAG CCT TCG    (SEQ ID NO: 27)
 Q   V   Q   L   Q   E   S   G   P   G   L   V   K   P   S     (SEQ ID NO: 3)

GAG ACC CTG TCC CTC ACG TGC ACT GTC TCT GGT GGC TCC ATC AGT
 E   T   L   S   L   T   C   T   V   S   G   G   S   I   S

AAT TAC TAC TGG AGT TGG ATC CGG CAG TCC CCA GGG AGG GGA CTG
 N   Y   Y   W   S   W   I   R   Q   S   P   G   R   G   L

GAG TGG ATT GGG TAT ATC CAT TAT AGT GGG AGC ACC AAC TCC AAT
 E   W   I   G   Y   I   H   Y   S   G   S   T   N   S   N

CCA TCC CTC AAG AGT CGA GTC ACC ATA TCA GTT GAC ACG TCC AAG
 P   S   L   K   S   R   V   T   I   S   V   D   T   S   K

AAC CAG GTC TCC CTG AAG CTG GGC TCT GTG ACC GCT GCG GAC ACG
 N   Q   V   S   L   K   L   G   S   V   T   A   A   D   T

GCC ATA TAT TAC TGT GCG AGA GAT ACT TAC TAT GAA AGT AGT GGT
 A   I   Y   Y   C   R   D   T   Y   Y   E   S   S   G

CAT TGG TTC GAC GGT TTG GAC GTC TGG GGC CAA GGG ACC TCG GTC
 H   W   F   D   G   L   D   V   W   G   Q   G   T   S   V

ACC GTC TCC TCA
 T   V   S   S
```

IIIb. F628 HEAVY CHAIN VARIABLE REGION AMINO ACID SEQUENCE
QVQLQESGPGLVKPSETLSLTCTVSGGSISNYYWSWIRQSPGRGLEWIGYIHYSGSTNSNPS    (SEQ ID NO: 3)
LKSRVTISVDTSKNQVSLKLGSVTAADTAIYYCARDTYYESSGHWFDGLDVWGQGTSVTVSS

QVQLQESGPGLVKPSETLSLTCTVSGGSISNYYWSWIRQSPGRGLEWIGYIHYSGSTNSNPS    (SEQ ID NO: 58)
LKSRVTISVDTSKNQVSLKLGSVTAADTAIYYCARDTYYESSGHWFDGLDVWGQGTSVTVSS
*ASTKGP*

IIIc. F628 HEAVY CHAIN VARIABLE REGION NUCLEOTIDE SEQUENCE
```
CAG GTG CAG CTG CAG GAG TCG GGC CCA GGA CTG GTG AAG CCT TCG    (SEQ ID NO: 27)
GAG ACC CTG TCC CTC ACG TGC ACT GTC TCT GGT GGC TCC ATC AGT
AAT TAC TAC TGG AGT TGG ATC CGG CAG TCC CCA GGG AGG GGA CTG
GAG TGG ATT GGG TAT ATC CAT TAT AGT GGG AGC ACC AAC TCC AAT
CCA TCC CTC AAG AGT CGA GTC ACC ATA TCA GTT GAC ACG TCC AAG
AAC CAG GTC TCC CTG AAG CTG GGC TCT GTG ACC GCT GCG GAC ACG
GCC ATA TAT TAC TGT GCG AGA GAT ACT TAC TAT GAA AGT AGT GGT
CAT TGG TTC GAC GGT TTG GAC GTC TGG GGC CAA GGG ACC TCG GTC
ACC GTC TCC TCA

CAG GTG CAG CTG CAG GAG TCG GGC CCA GGA CTG GTG AAG CCT TCG    (SEQ ID NO: 59)
GAG ACC CTG TCC CTC ACG TGC ACT GTC TCT GGT GGC TCC ATC AGT
AAT TAC TAC TGG AGT TGG ATC CGG CAG TCC CCA GGG AGG GGA CTG
GAG TGG ATT GGG TAT ATC CAT TAT AGT GGG AGC ACC AAC TCC AAT
CCA TCC CTC AAG AGT CGA GTC ACC ATA TCA GTT GAC ACG TCC AAG
AAC CAG GTC TCC CTG AAG CTG GGC TCT GTG ACC GCT GCG GAC ACG
GCC ATA TAT TAC TGT GCG AGA GAT ACT TAC TAT GAA AGT AGT GGT
CAT TGG TTC GAC GGT TTG GAC GTC TGG GGC CAA GGG ACC TCG GTC
ACC GTC TCC TCA GCT AGC ACC
```

IVa. F628 LIGHT CHAIN VARIABLE REGION AMINO ACID AND NUCLEOTIDE SEQUENCE

```
                                    -continued
ALIGNMENT
CAG CCT GTG CTG ACT CAG TCG CCC TCT GCC TCT GCC TCC CTG GGA        (SEQ ID NO: 28)
 Q   P   V   L   T   Q   S   P   S   A   S   A   S   L   G        (SEQ ID NO: 4)

GCC TCG GTC AAG CTC ACC TGC ACT CTG GAC AGT GAA CAC AGC AGA
 A   S   V   K   L   T   C   T   L   D   S   E   H   S   R

TAC ACC ATC GCA TGG CAT CAG CAG CCA GAG AAG GGC CCT CGG
 Y   T   I   A   W   H   Q   Q   P   E   K   G   P   R

TAC CTG ATG AAG GTT AAG AGT GAT GGC AGT CAC AGC AAG GGG GAC
 Y   L   M   K   V   K   S   D   G   S   H   S   K   G   D

GGC ATT ACT GAT CGC TTC TCA GGC TCC AGC TCT GGG GCT GAG CGC
 G   I   T   D   R   F   S   G   S   S   S   G   A   E   R

TAC CTC ACC ATC TCC AGC CTC CAG TCT GAG GAT GAG GCT GAC TAT
 Y   L   T   I   S   S   L   Q   S   E   D   E   A   D   Y

TAC TGT CAG ACT TGG GGC CCT GGC ATT CGA GTG TTC GGC GGA GGG
 Y   C   Q   T   W   G   P   G   I   R   V   F   G   G   G

ACC AAG CTG ACC GTC CTA
 T   K   L   T   V   L

IVb. F628 LIGHT CHAIN VARIABLE REGION AMINO ACID SEQUENCE
QPVLTQSPSASASLGASVKLTCTLDSEHSRYTIAWHQQQPEKGPRYLMKVKSDGSHSKGDGI   (SEQ ID NO: 4)
TDRFSGSSSGAERYLTISSLQSEDEA DYYCQTWGPGIRVFGGGTKLTVL

IVc. F628 LIGHT CHAIN VARIABLE REGION NUCLEOTIDE SEQUENCE
CAG CCT GTG CTG ACT CAG TCG CCC TCT GCC TCT GCC TCC CTG GGA        (SEQ ID NO: 28)
GCC TCG GTC AAG CTC ACC TGC ACT CTG GAC AGT GAA CAC AGC AGA
TAC ACC ATC GCA TGG CAT CAG CAG CCA GAG AAG GGC CCT CGG
TAC CTG ATG AAG GTT AAG AGT GAT GGC AGT CAC AGC AAG GGG GAC
GGC ATT ACT GAT CGC TTC TCA GGC TCC AGC TCT GGG GCT GAG CGC
TAC CTC ACC ATC TCC AGC CTC CAG TCT GAG GAT GAG GCT GAC TAT
TAC TGT CAG ACT TGG GGC CCT GGC ATT CGA GTG TTC GGC GGA GGG
ACC AAG CTG ACC GTC CTA

Va. F630 HEAVY CHAIN VARIABLE REGION AMINO ACID AND NUCLEOTIDE SEQUENCE
ALIGNMENT
CAG GTT CAG CTG GTG CAG TCT GGA GCT GAG ATG AAG AGG CCT GGG        (SEQ ID NO: 29)
 Q   V   Q   L   V   Q   S   G   A   E   M   K   R   P   G        (SEQ ID NO: 5)

GCC TCA GTG AAG GTC TCC TGC AAG GCT TCT GGT TAC ACC TTT ACC
 A   S   V   K   V   S   C   K   A   S   G   Y   T   F   T

AAC TTT GGT ATC AGT TGG GTG CGA CAG GCC CCT GGA CAA GGG CTT
 N   F   G   I   S   W   V   R   Q   A   P   G   Q   G   L

GAG TGG ATA GGA TGG GTC AGC ACT TAC AAT GGT CGC ACA AAT TAT
 E   W   I   G   W   V   S   T   Y   N   G   R   T   N   Y

GCA CAG AAG TTC CGG GGC AGA GTC ACC ATG ACC ACA GAC ACA TCC
 A   Q   K   F   R   G   R   V   T   M   T   T   D   T   S

ACG AAC ACA GCG TAC ATG GAA CTG AGG AGC CTG GGA TCT GAC GAC
 T   N   T   A   Y   M   E   L   R   S   L   G   S   D   D

ACG GCC GTC TTT TAC TGT GCG AGA GAT TAC TAT GAG ACT AGT GGT
 T   A   V   F   Y   C   A   R   D   Y   Y   E   T   S   G

TAC GCC TAT GAT GAT TTT GCG ATC TGG GGC CAA GGG ACA TTG GTC
 Y   A   Y   D   D   F   A   I   W   G   Q   G   T   L   V

ACC GTC TCC TCA
 T   V   S   S

Vb. F630 HEAVY CHAIN VARIABLE REGION AMINO ACID SEQUENCE
QVQLVQSGAEMKRPGASVKVSCKASGYTFTNFGISWVRQAPGQGLEWIGWVSTYNGRTNYAQ   (SEQ ID NO: 5)
KFRGRVTMTTDTSTNTAYMELRSLGSDDTAVFYCARDYYETSGYAYDDFAIWGQGTLVTVSS

Vc. F630 HEAVY CHAIN VARIABLE REGION NUCLEOTIDE SEQUENCE
CAG GTT CAG CTG GTG CAG TCT GGA GCT GAG ATG AAG AGG CCT GGG        (SEQ ID NO: 29)
GCC TCA GTG AAG GTC TCC TGC AAG GCT TCT GGT TAC ACC TTT ACC
AAC TTT GGT ATC AGT TGG GTG CGA CAG GCC CCT GGA CAA GGG CTT
GAG TGG ATA GGA TGG GTC AGC ACT TAC AAT GGT CGC ACA AAT TAT
GCA CAG AAG TTC CGG GGC AGA GTC ACC ATG ACC ACA GAC ACA TCC
ACG AAC ACA GCG TAC ATG GAA CTG AGG AGC CTG GGA TCT GAC GAC
ACG GCC GTC TTT TAC TGT GCG AGA GAT TAC TAT GAG ACT AGT GGT
```

```
                                       -continued
TAC GCC TAT GAT GAT TTT GCG ATC TGG GGC CAA GGG ACA TTG GTC
ACC GTC TCC TCA VIa. F630 LIGHT CHAIN VARIABLE REGION AMINO ACID AND NUCLEOTIDE SEQUENCE
ALIGNMENT
CAG CTT GTG CTG ACT CAA TCG CCC TCT GCC TCT GCT TCC CTG GGA      (SEQ ID NO: 30)
 Q   L   V   L   T   Q   S   P   S   A   S   A   S   L   G      (SEQ ID NO:  6)

GCC TCG GTC AAG CTC ACC TGC ACT CTG AGC AGT GGG CAC AGC ACC
 A   S   V   K   L   T   C   T   L   S   S   G   H   S   T

TAC GCC ATC GCG TGG CAT CAG CAG CAG CCA CTG AGG GGT CCT CGT
 Y   A   I   A   W   H   Q   Q   Q   P   L   R   G   P   R

TTC TTG ATG AAA GTC AAC AGT GAT GGC AGC CAC ACC AAG GGG GAC
 F   L   M   K   V   N   S   D   G   S   H   T   K   G   D

GGG ATC CCT GAT CGC TTC TCA GGC TCC AGT TCT GGG GCT GAG CGC
 G   I   P   D   R   F   S   G   S   S   S   G   A   E   R

TAC CTC TCC ATC TCC AGC CTC CAG TCT GAA GAT GAG TCT GAC TAT
 Y   L   S   I   S   S   L   Q   S   E   D   E   S   D   Y

TAC TGT CAG ACG TGG GGC CCT GGC ATT CGA GTG TTC GGC GGA GGG
 Y   C   Q   T   W   G   P   G   I   R   V   F   G   G   G

ACC AAG CTG ACC GTC CTA GGT
 T   K   L   T   V   L   G

VIb. F630 LIGHT CHAIN VARIABLE REGION NUCLEOTIDE SEQUENCE
QLVLTQSPSASASLGASVKLTCTLSSGHSTYAIAWHQQQPLRGPRFLMKVNSDGSHTKGDGI      (SEQ ID NO:  6)
PDRFSGSSSGAERYLSISSLQSEDESDYYCQTWGPGIRVFGGGTKLTVLG

QLVLTQSPSASASLGASVKLTCTLSSGHSTYAIAWHQQQPLRGPRFLMKVNSDGSHTKGDGI      (SEQ ID NO: 60)
PDRFSGSSSGAERYLSISSLQSEDESDYYCQTWGPGIRVFGGGTKLTVLG*QPKAAPSV*

VIc. F630 LIGHT CHAIN VARIABLE REGION NUCLEOTIDE SEQUENCE
CAG CTT GTG CTG ACT CAA TCG CCC TCT GCC TCT GCT TCC CTG GGA      (SEQ ID NO: 30)
GCC TCG GTC AAG CTC ACC TGC ACT CTG AGC AGT GGG CAC AGC ACC
TAC GCC ATC GCG TGG CAT CAG CAG CAG CCA CTG AGG GGT CCT CGT
TTC TTG ATG AAA GTC AAC AGT GAT GGC AGC CAC ACC AAG GGG GAC
GGG ATC CCT GAT CGC TTC TCA GGC TCC AGT TCT GGG GCT GAG CGC
TAC CTC TCC ATC TCC AGC CTC CAG TCT GAA GAT GAG TCT GAC TAT
TAC TGT CAG ACG TGG GGC CCT GGC ATT CGA GTG TTC GGC GGA GGG
ACC AAG CTG ACC GTC CTA GGT

CAG CTT GTG CTG ACT CAA TCG CCC TCT GCC TCT GCT TCC CTG GGA      (SEQ ID NO: 61)
GCC TCG GTC AAG CTC ACC TGC ACT CTG AGC AGT GGG CAC AGC ACC
TAC GCC ATC GCG TGG CAT CAG CAG CAG CCA CTG AGG GGT CCT CGT
TTC TTG ATG AAA GTC AAC AGT GAT GGC AGC CAC ACC AAG GGG GAC
GGG ATC CCT GAT CGC TTC TCA GGC TCC AGT TCT GGG GCT GAG CGC
TAC CTC TCC ATC TCC AGC CTC CAG TCT GAA GAT GAG TCT GAC TAT
TAC TGT CAG ACG TGG GGC CCT GGC ATT CGA GTG TTC GGC GGA GGG
ACC AAG CTG ACC GTC CTA GGT CAG CCC AAG GCT GCC CCA TCG GTC
ACC TGT TCC CGC CTC
```

Figure 2:
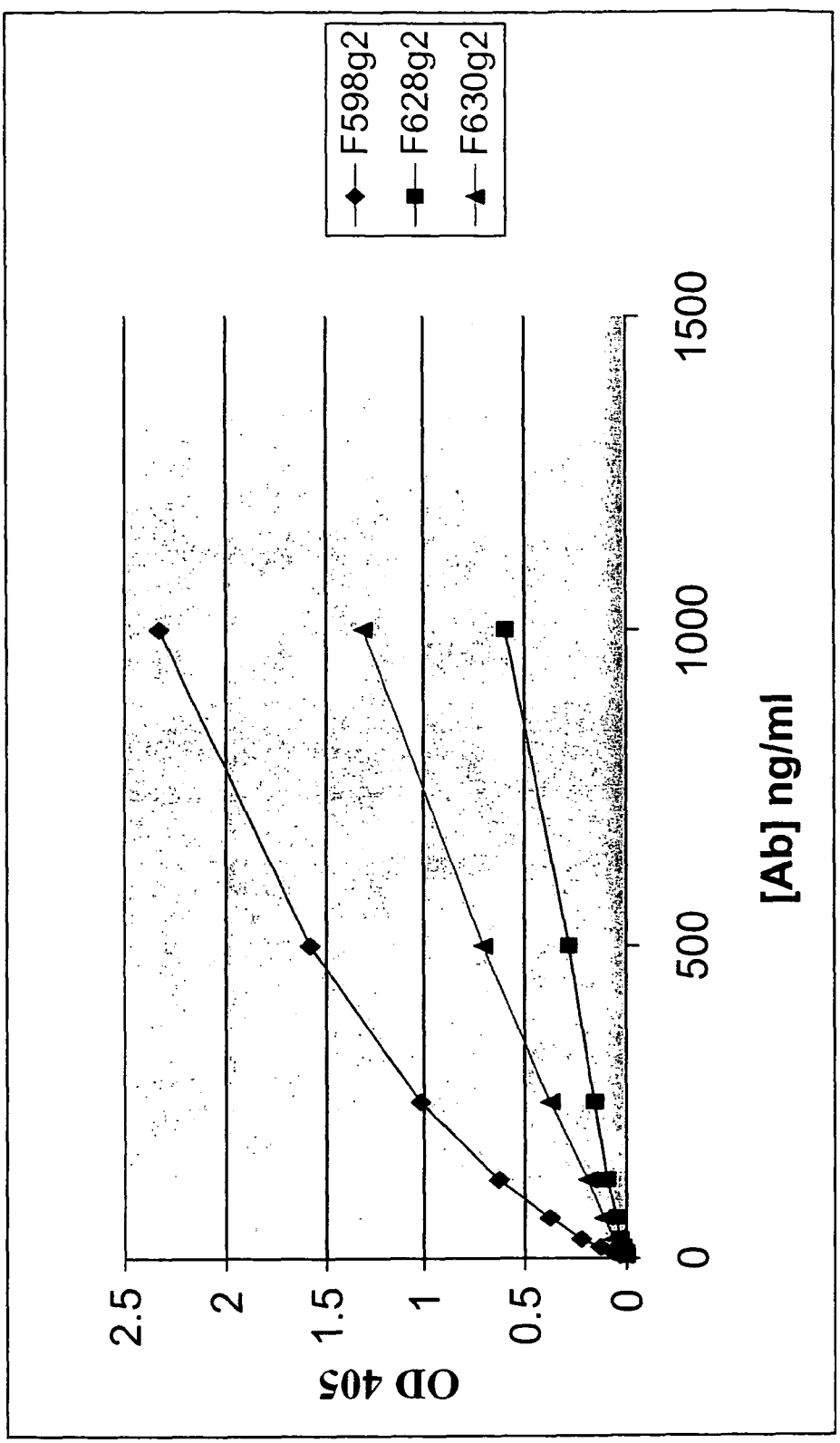
FIG. 2 is a graph showing the binding affinities of MAbs F598, F628 and F630 (in an IgG2 form) to dPNAG.

Characterization of IgG2 MAbs:

The hybridomas were named from their corresponding fusion numbers: F598, F628, and F630. The antibodies produced from these hybridomas were all IgG2 and lambda types. After purification of the antibodies using protein G columns, ELISAs were used to determine differences in epitope specificities of the MAbs. Chemical modification of native PNAG was performed in order to remove certain substituents. Strong base treatment (5M NaOH) results in removal of most of the N-acetyl groups. As seen in FIG. 1 all of the MAbs bind well to the native form of PNAG, although with different binding curves. When PNAG is treated with 5M NaOH to yield dPNAG, F598 MAb binds with the greatest activity (FIG. 2). This result suggests that F598 has specificity for the backbone epitopes of PNAG and does not require N- and O-acetylated groups to bind to the PNAG polymer. MAbs F630 and F628 bind poorly to dPNAG suggesting that their specificities require the acetates found in the native form of PNAG.

Figure 3:
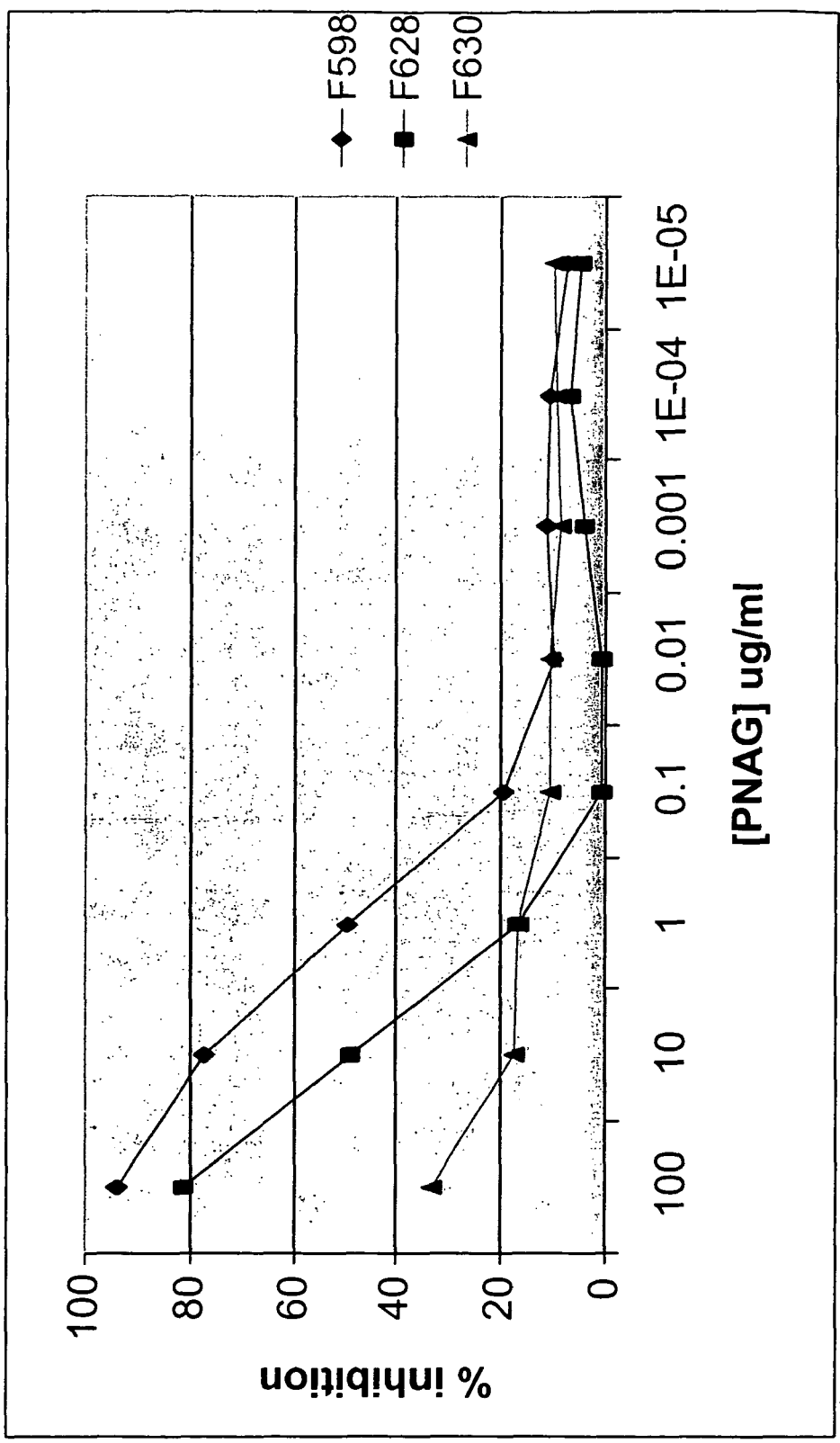
FIG. 3 is a graph showing the results of a competition ELISA using PNAG and MAbs F598, F628 and F630 (in an IgG2 form).

Competition ELISAs were used to determine the relative binding activities of the MAbs. FIG. 3 shows that the relative binding activity of the MAbs are: F598>F628>F630.

Creation and Characterization of IgG1 Switched MAbs:

Human IgG1 isotype antibodies can fix complement onto the surface of an antigen better than antibodies of the IgG2 isotype. Therefore, cloning of the MAb variable regions and production of the IgG1 isotype was performed. Primers directed at the IgG2 constant region and primers specific for the 5' end of the variable regions identified in the original hybridomas (see listing of primers herein under "Cloning of antibody variable regions") were used to obtain PCR products from cDNA preparations made from mRNA isolated from the original IgG2 hybridoma cell lines. PCR products were sequenced and analyzed to determine the germline genes that most likely gave rise to each antibody. As shown in Table 1, there are common germline genes that are used by the hybridomas in making antibodies directed to PNAG and/or dPNAG. As shown, MAbs F598, F628 and F630 use the same light chain germline genes and heavy chain D regions. The only difference is the V gene used to produce the heavy chain of MAb F630 and the J gene used to produce the heavy chain of MAb F628; the remainder of the germline genes are identical for the MAbs. Table 1.

TABLE 1

| Hybridoma H or L chain | Germline Genes | | |
|---|---|---|---|
| F598L | IGLV4-69 or V5-6 | | IGLJ3 or IGLJ2 |
| F598H | IGHV4-59 | IGHD3-22 | IGHJ3 |
| F628L | IGLV4-69 or V5-6 | | IGLJ3 or IGLJ2 |
| F628H | IGHV4-59 | IGHD3-22 | IGHJ6 |
| F630L | IGLV4-69 or V5-6 | | IGLJ3 or IGLJ2 |
| F630H | IGHV1-18 | IGHD3-22 | IGHJ3 |

Figure 4:
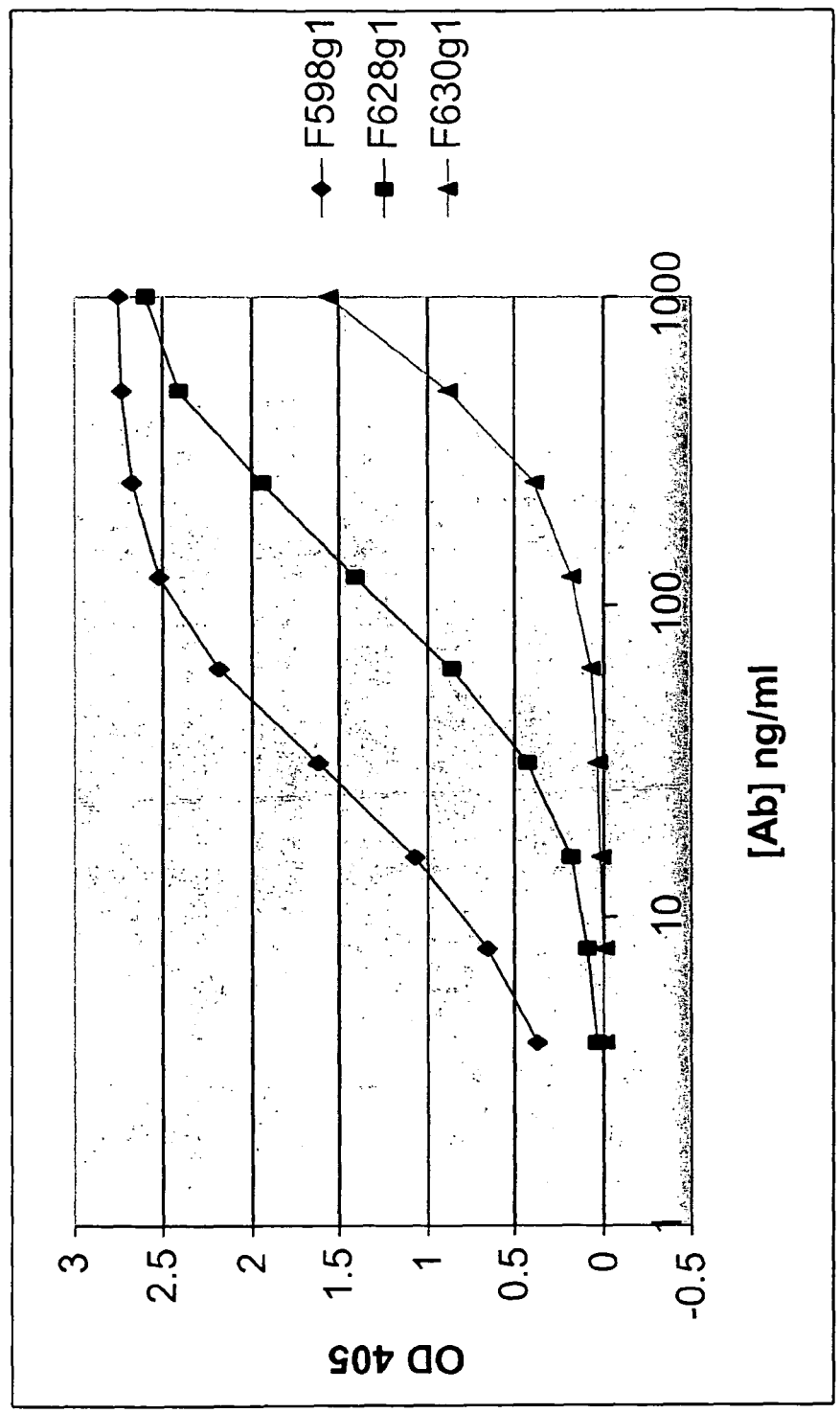
FIG. 4 is a graph showing the binding affinities of MAbs F598, F628 and F630 (in an IgG1 form) to native PNAG.
Figure 5:
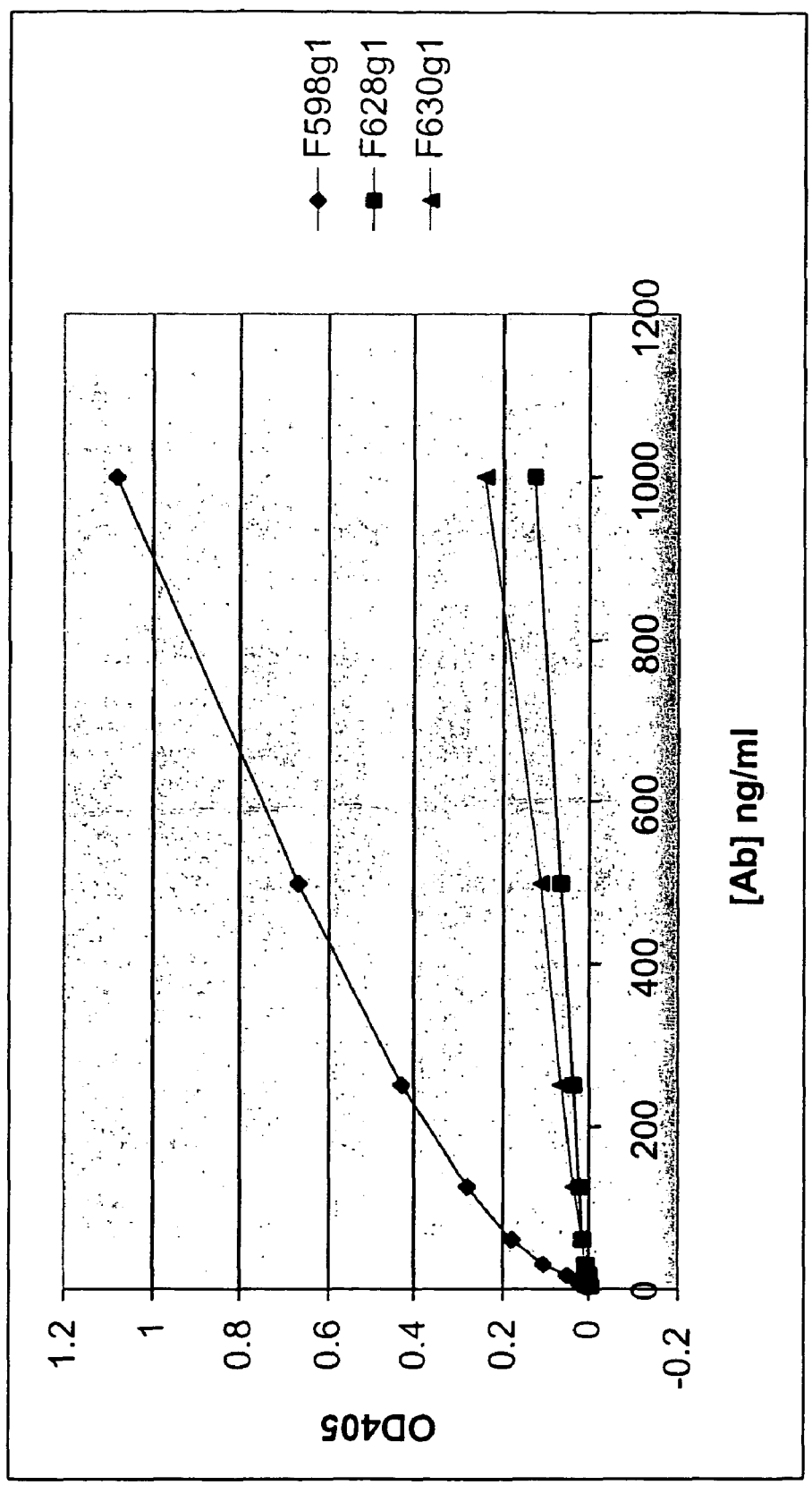
FIG. 5 is a graph showing the binding affinities of MAbs F598, F628 and F630 (in an IgG1 form) to dPNAG.

The DNA encoding the entire variable regions encompassing V, J and D segments for the heavy chain and V and J segments for the light chain of each of the MAbs (F598, F728 and F630) was cloned into the TCAE6 vector, which contains the kappa light chain and IgG1 heavy chain human constant regions. The initial constructs maintained the original pairing of the heavy and light chain genes obtained from the original hybridomas. Plasmid DNA containing each of the constructs were transfected into CHO cells and the resulting IgG1 MAbs were purified and characterized. As seen in FIGS. 4 and 5, all of the IgG1 MAbs have identical binding curves to PNAG when compared to the original IgG2 MAbs, however the IgG1 constructs of MAbs F628 and F630 have lost some of their ability to bind to dPNAG (e.g., compare with FIGS. 1 and 2).

Figure 6:
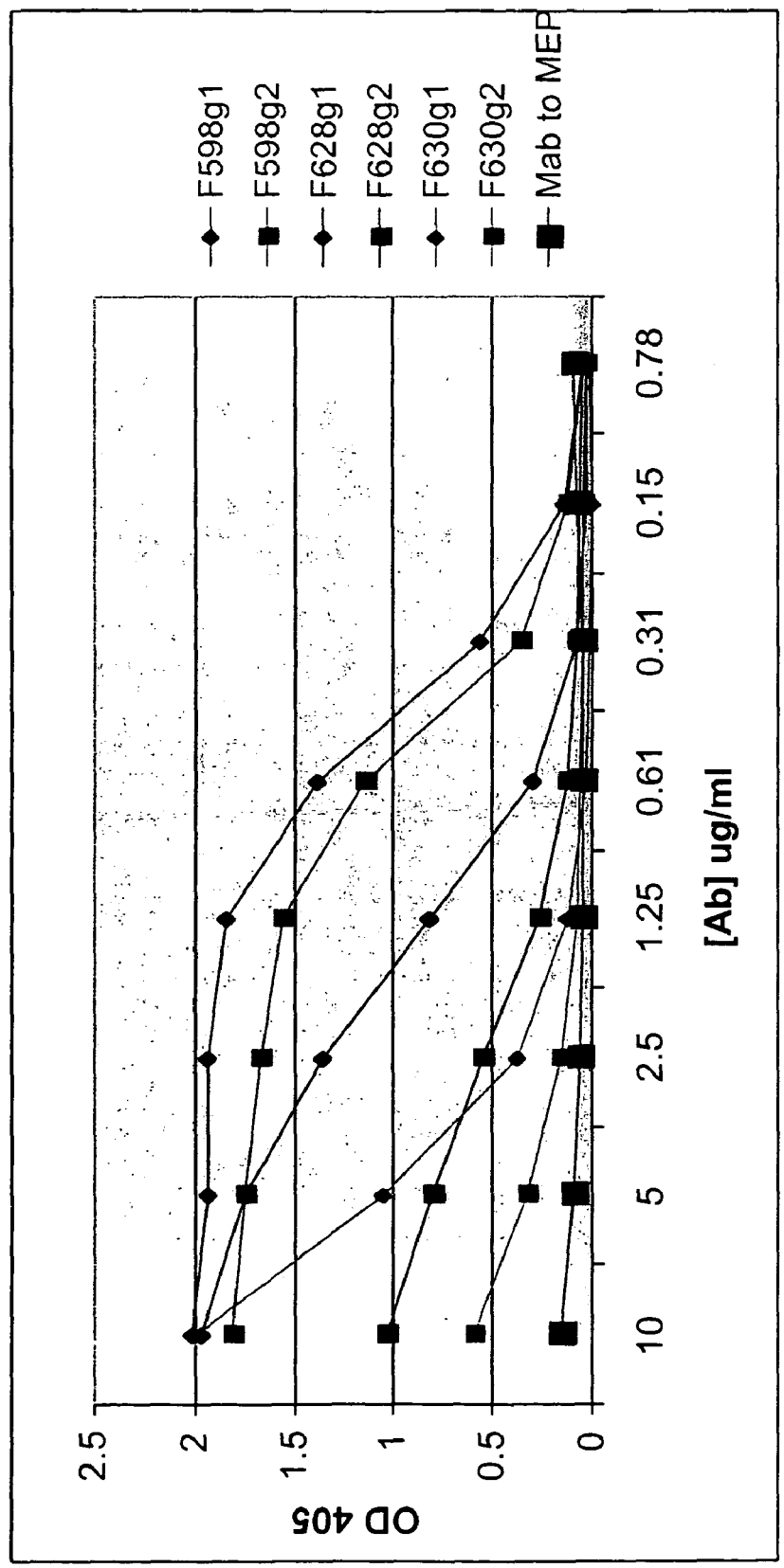
FIG. 6 is a graph showing complement fixation activity of MAbs F598, F628 and F630 in both IgG1 and IgG2 form on PNAG. MAb to *P. aeruginosa* MEP is used as a negative control.

To test whether the IgG1 MAbs have more functional complement activating activity than the IgG2 parental MAbs, complement deposition assays were performed. The complement deposition assay is essentially an ELISA assay that measures the deposition of complement protein C3 when human serum is added to the reaction mixture. As shown in FIG. 6, all of the IgG1 MAbs have better complement fixing activity than the parental IgG2 MAbs. The extent of the increase in complement fixation depends on the MAb. For MAb F598, which has the highest binding activity to PNAG and dPNAG, there is only a slight increase in activity of the IgG1 over the IgG2 isotype. For MAbs F628 and F630, the IgG1 MAbs have at least double the complement deposition activity than the parental IgG2 MAbs.

Figure 7:
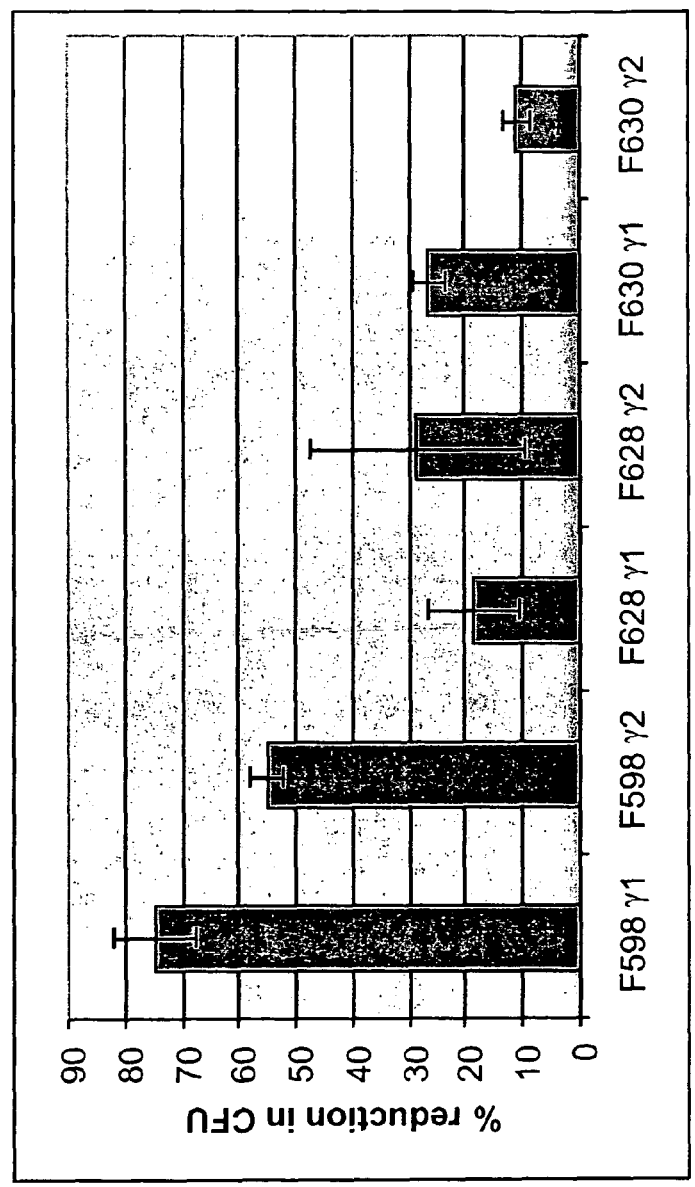
FIG. 7 is a graph showing the opsonophagocytic activity of MAbs F598, F628 and F630 in IgG1 and IgG2 form against *S. aureus* strain Mn8.

Opsonophagocytic Activity:

The opsonophagocytic activity of monoclonal antibodies F598, F628 and F630 in both the IgG1 and IgG2 forms (6 µg of MAb) was tested against S. aureus strain Mn8. Monoclonal antibody F598 showed the highest level of reduction (i.e., killing) in CFU when the IgG1 form was used (FIG. 7).

Figure 8A:
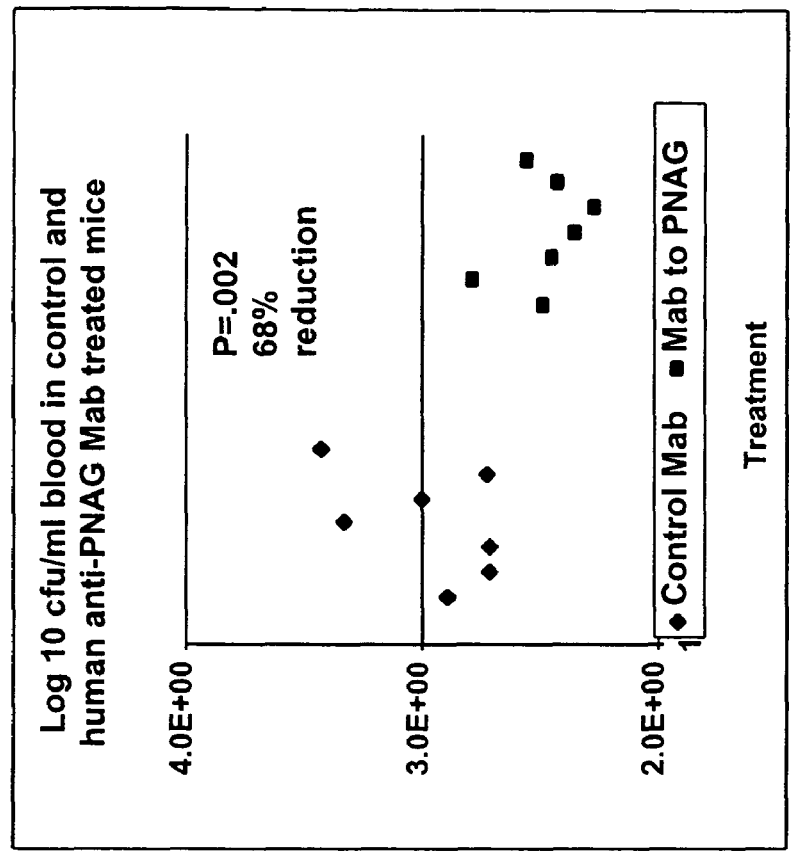
FIG. 8A is a bar graph showing averaged results comparing levels of Staphylococci in the blood of mice (8 per group) given either a control human IgG1 MAb to *P. aeruginosa* alginate or MAb F598 specific to PNAG/dPNAG (in an IgG1 form) and demonstrating that MAb F598 can provide passive protection against *S. aureus* challenge.
Figure 8B:
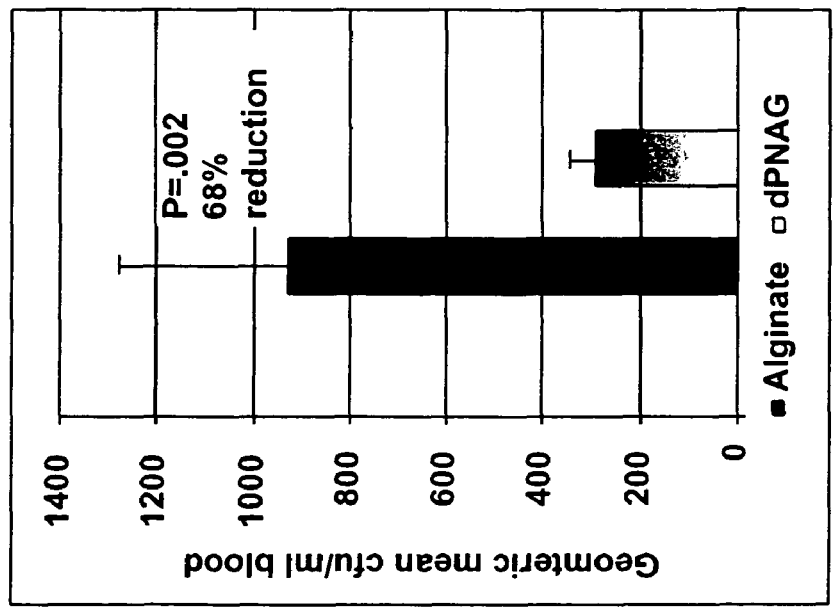
FIG. 8B is a graph showing the results of protection against *S. aureus* challenge in individual mice, reporting the CFU per ml of blood following administration of a control human IgG1 MAb to *P. aeruginosa* alginate and MAb F598 specific for PNAG/dPNAG (in an IgG1 form).
Figure 8C:
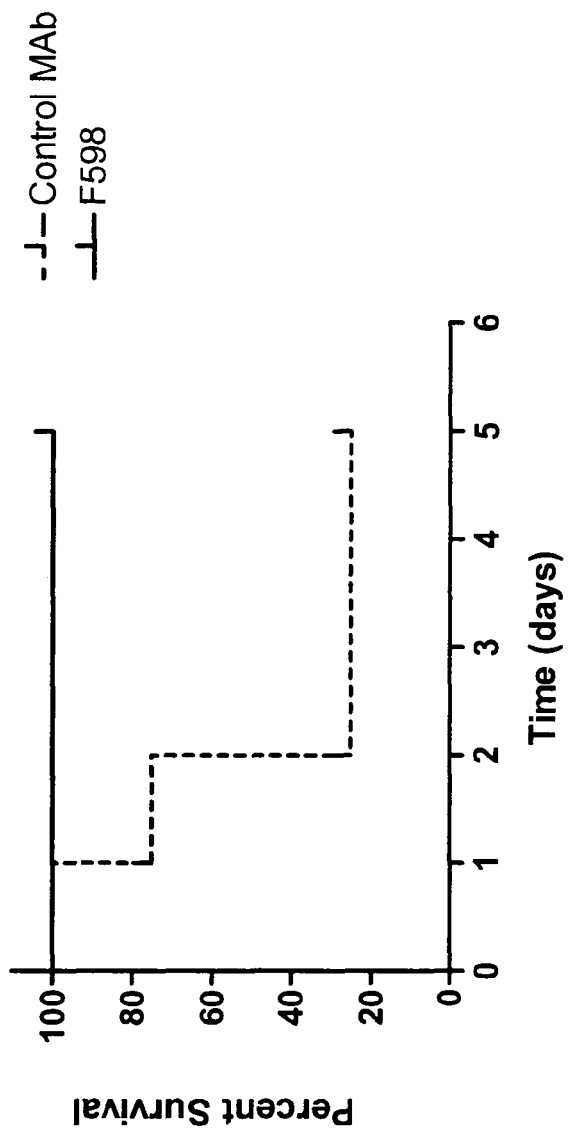
FIG. 8C is a graph showing the results of protection against *S. aureus* challenge in individual FVB mice using MAb F598 and control MAb to *P. aeruginosa* MEP.

Passive Protection Against Infection:

Administration of the MAb F598 that binds to both PNAG and dPNAG to mice 24 hours prior to challenge with S. aureus strain Mn8 resulted in a 68% reduction 2 hours following infection in the number of CFU/ml blood as compared to mice receiving a MAb to an irrelevant antigen, P. aeruginosa alginate (significance of P=0.002) (FIG. 8A). FIG. 8B shows the CFU of S. aureus per ml of blood for each individual animal given either the control MAb or the MAb F598g1. Administration of 800 µg MAb F598 per FVB mouse 4 hours prior to intraperitoneal (IP) challenge with $5 \times 10^8$ CFU S. aureus (Mn8 strain) resulted in increased survival compared to mice administered a control MAb (F429 specific to P. aeruginosa). FIG. 8C shows the results of these experiments. At five days after bacterial challenge, all mice that received F598 and only about 20% of mice receiving control MAb were alive (8 mice per group).

E. coli Urinary Tract Infection Isolates:

Eighteen E. coli clinical urinary tract infection (UTI) isolates were isolated and tested for the presence of the pga locus by PCR and PNAG expression by immunoblot using antisera raised to S. aureus PNAG. The clinical isolates were grown in culture and either DNA was extracted by standard techniques for use in PCR or cells were subjected to EDTA extraction (boiling for 5 minutes) once cells were in stationary phase. Seventeen of the eighteen isolates carried pga genes as determined by PCR. Based on the immunoblot results, of these seventeen, about one third were characterized as expressing relatively high levels of PNAG, about one third were characterized as expressing relatively intermediate (or moderate) levels of PNAG and the remaining one third were characterized as expressing relatively low levels of PNAG. In addition, over-expression of the pga locus resulted in enhanced production of PNAG. FIG. 9 shows the results of this immunoblot. Strain "H" expresses undetectable levels of PNAG and does not have apga locus. The slot at the upper right hand corner represents the pga over-expressing strain of E. coli.

Figure 10:
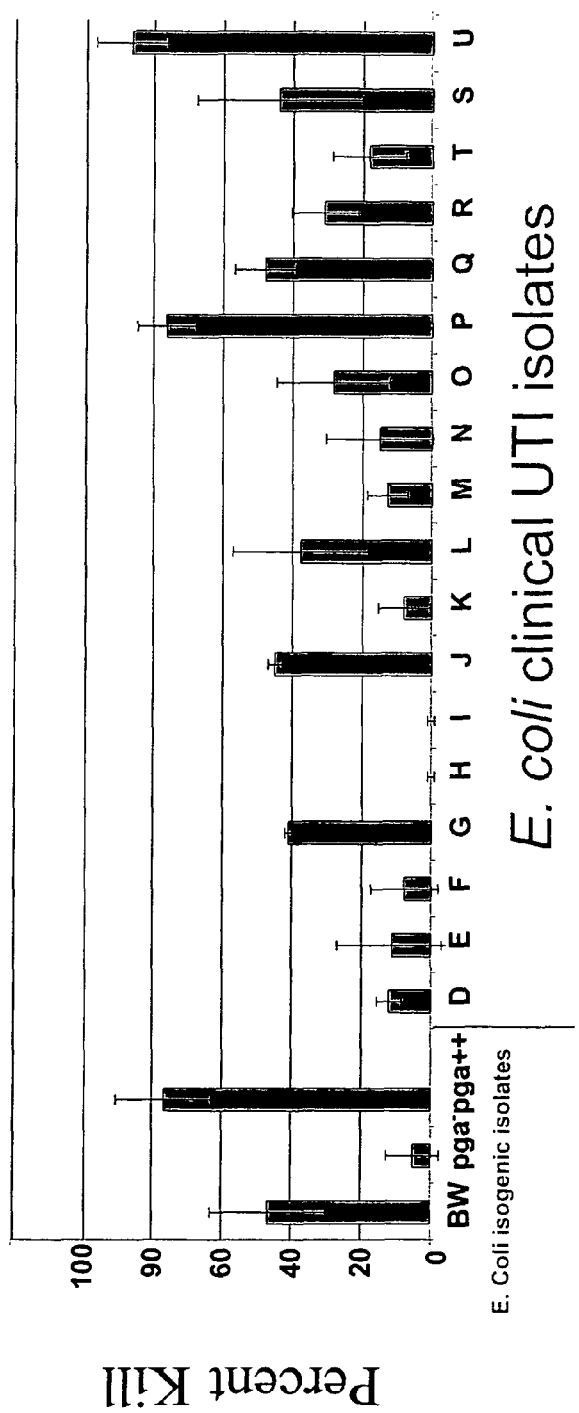
FIG. 10 is a bar graph showing the level of killing of *E. coli* isolates using polyclonal antiserum raised against *S. aureus* dPNAG.

FIG. 10 shows the level of opsonic killing of the aforementioned E. coli clinical UTI isolates using a polyclonal antiserum raised against S. aureus dPNAG. BW represents a wild type E. coli strain, pga⁻ represents an E. coli strain with the pga locus deleted, and pga represents a pga over-expressing strain of E. coli. The level of killing roughly correlates with the level of PNAG expression by the E. coli isolate.

Figures 11A, 11B:
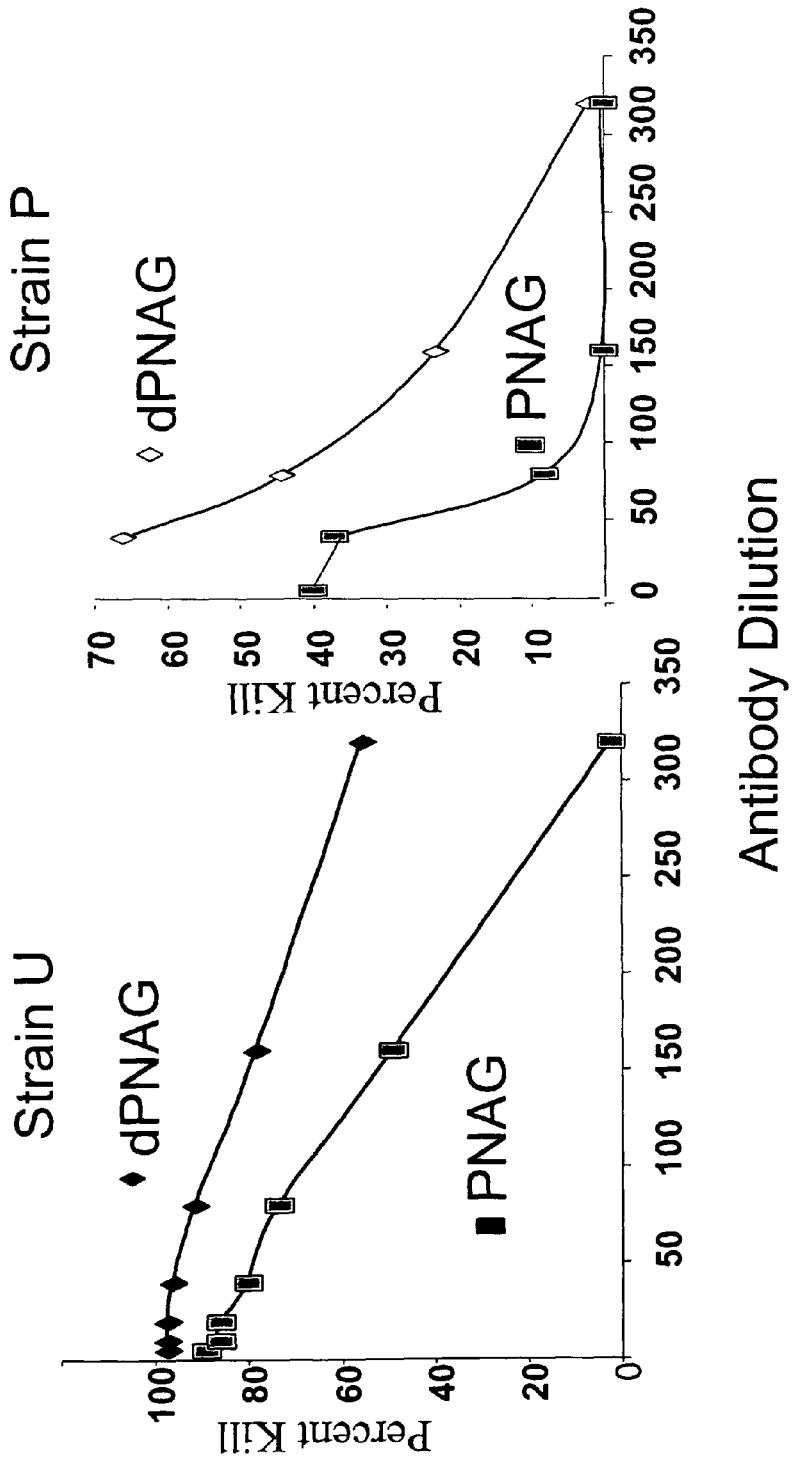
FIGS. 11A and 11B are graphs showing the level of killing of *E. coli* isolates expressing relatively high (strain U) and intermediate (strain P) levels of PNAG, respectively, using polyclonal antiserum raised against dPNAG and PNAG.

FIGS. 11A and 11B show the level of opsonic killing of a high PNAG expressing E. coli strain (strain U) and an intermediate PNAG expressing E. coli strain (strain P) by polyclonal antiserum raised against dPNAG and PNAG. At all antiserum dilutions tested, the anti-dPNAG was more effective at killing either strain than the anti-PNAG antiserum.

Figure 12:
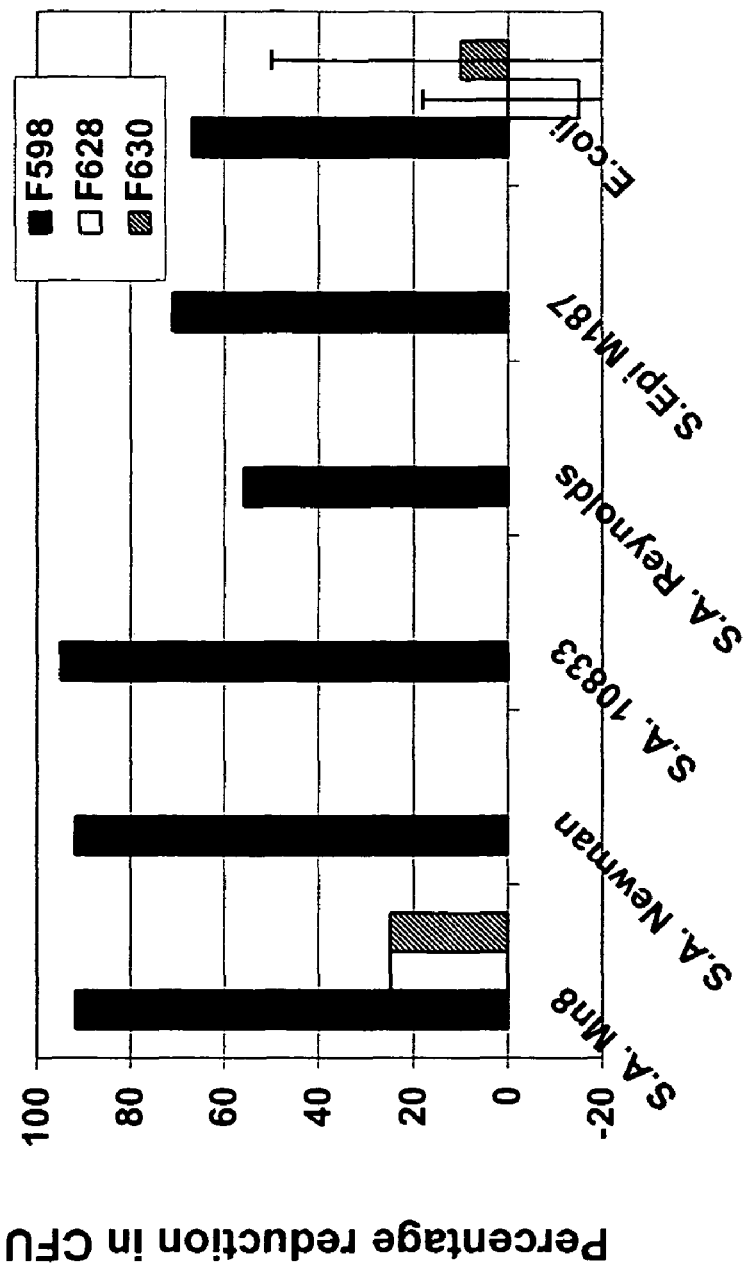
FIG. 12 is a bar graph showing reduction in CFU from different PNAG-expressing bacterial strains using F598, F628 and F630.

FIG. 12 shows the opsonophagocytic activity of MAb F598 against various Staphylococcal strains and an E. coli strain by MAb F598, F628 and F630 (6 µg/ml of MAb per assay).

Figure 13:
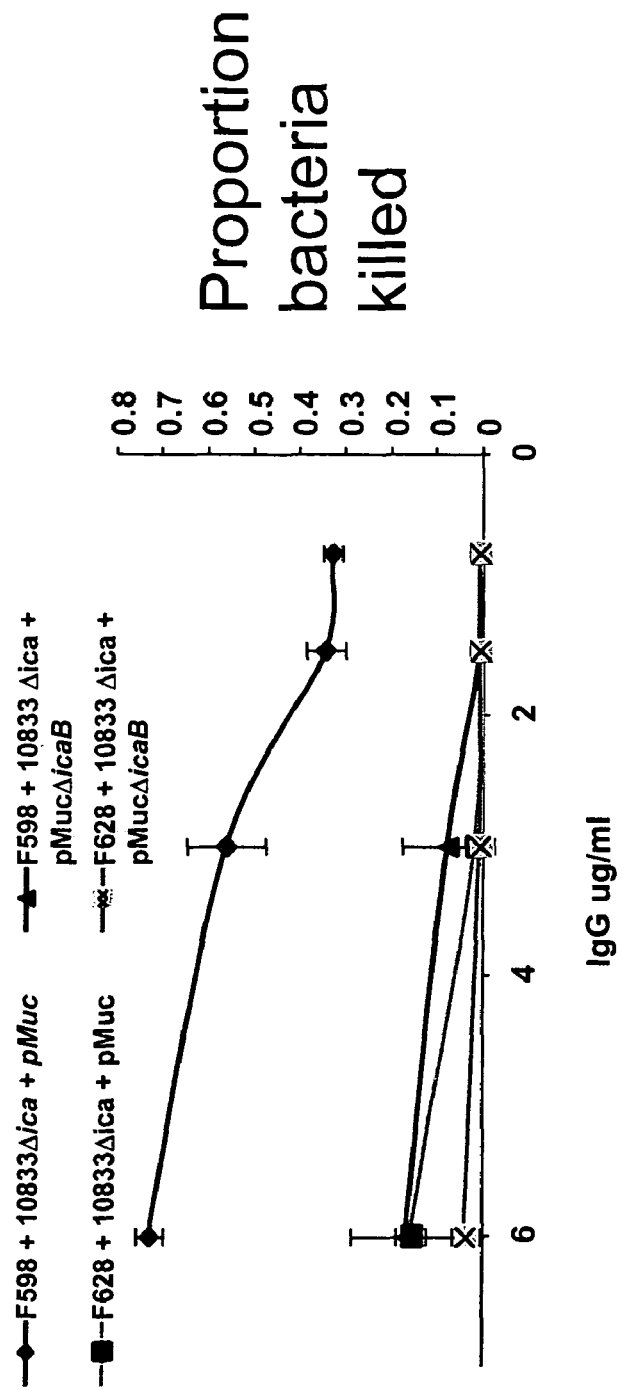
FIG. 13 is a graph showing proportion of *S. aureus* bacteria killed by F598 and F628 as a function of icaB gene presence or absence.
Figure 14:
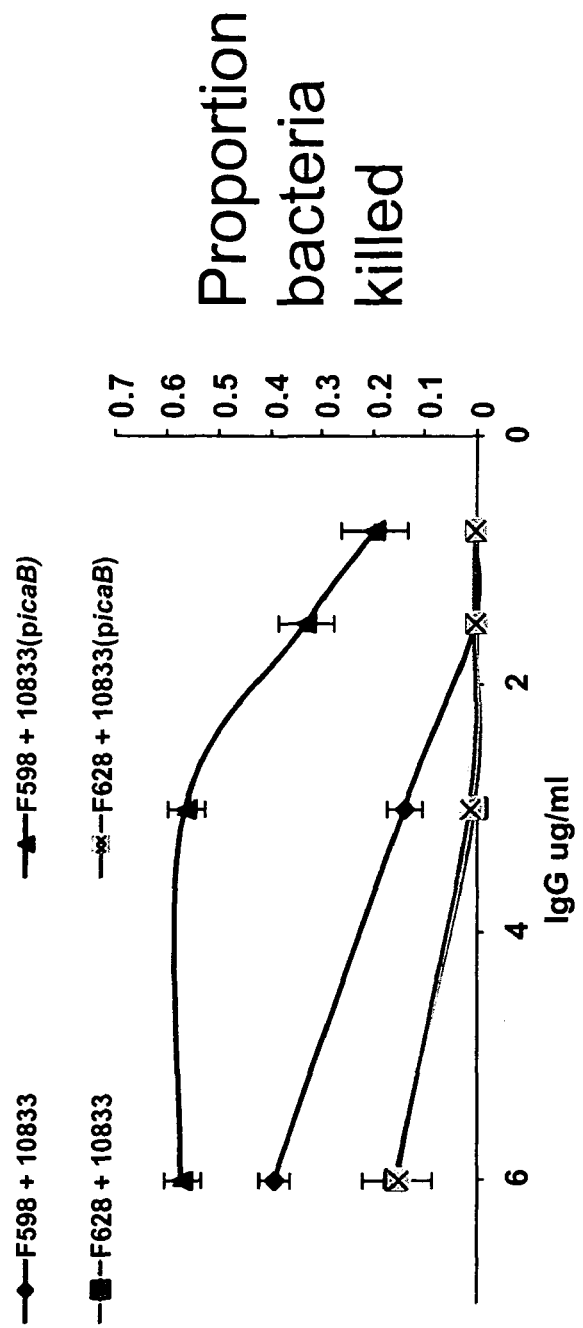
FIG. 14 is a graph showing proportion of *S. aureus* bacteria killed by F598 and F628 as a function of icaB gene over-expression.

Ica Locus Mutation:

FIGS. 13 and 14 shows the results of killing by MAbs F598 and F628 of S. aureus strains having mutant ica loci. S. aureus strain 10833 was deleted for the ica locus (10833Δica) then transformed with a plasmid carrying wild-type ica isolated from S. aureus Mn8m (pMuc, PNAG-over-producer) or with pMuc with the icaB gene deleted (pMucΔicaB), as shown in FIG. 13. S. aureus strain 10833 (wild type) and 10833 (picaB) are shown in FIG. 14. Strain 10833 (picaB) over-expresses the icaB gene from a plasmid using the constitutive promoter from the ica locus of S. aureus Mn8m (PNAG-over-producer). The icaB gene is the enzyme believed responsible for deacetylating PNAG. Deletion of the icaB gene affects killing by MAb F598 but not MAb F628. In the absence of the icaB gene, killing by MAb F598 is reduced (FIG. 13). Over-expression of the icaB gene results in enhanced killing by MAb F598 with little or no effect on MAb 628 killing.

CONCLUSIONS

ELISAs using chemically modified PNAG highlighted differences in the specificity of three fully human MAbs directed at the native form of PNAG. MAb F598 was found to recognize PNAG and dPNAG and so is specific for the backbone of the molecule. MAbs F628 and F630 apparently recognize acetate-specific epitopes. Competition ELISAs reveal that the relative binding activities of the MAbs ranks F598 with the highest binding activity followed by F628 and then F630. Cloning of the variable regions reveals that there is gene restriction usage for producing antibodies to PNAG and/or dPNAG. Changing the constant region of the MAbs from gamma 2 to gamma 1 resulted in identical binding to PNAG, but reduced the ability of 2 of the 3 MAbs to bind to dPNAG. Finally changing the constant region to gamma 1 resulted in an increased ability of the MAbs to fix complement, however this increase was most dramatic for MAbs F628 and F630 which have lower binding activity. Evaluation of the protective efficacy of MAb F598g1 showed administration this product to mice 24 hours before IV challenge with live *S. aureus* strain Mn8 resulted in a 68% reduction in the levels of Staphylococci in the blood 2 hours after infection. Administration of MAb F598 to mice 4 hours before IP challenge with live *S. aureus* strain Mn8 resulted in increased survival as compared to control MAb treated mice.

EQUIVALENTS

The foregoing written specification is to be considered to be sufficient to enable one skilled in the art to practice the invention. The particular antibodies and peptides disclosed herein are not to be construed as limiting of the invention as they are intended merely as illustrative of particular embodiments of the invention as enabled herein. Therefore, any peptides, antibodies, and antibody fragments that are functionally equivalent to those described herein are within the spirit and scope of the claims appended hereto. Indeed, various modifications of the invention in addition to those shown and described herein will become apparent to those skilled in the art from the foregoing description and fall within the scope of the appended claims.

All references, patents and patent publications that are recited in this application are incorporated in their entirety herein by reference.

---

SEQUENCE LISTING

```
<160> NUMBER OF SEQ ID NOS: 61

<210> SEQ ID NO 1
<211> LENGTH: 124
<212> TYPE: PRT
<213> ORGANISM: Homo sapiens

<400> SEQUENCE: 1

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Ile His Tyr Ser Arg Ser Thr Asn Ser Asn Pro Ala Leu Lys
    50                  55                  60

Ser Arg Val Thr Ile Ser Ser Asp Thr Ser Lys Asn Gln Leu Ser Leu
65                  70                  75                  80

Arg Leu Ser Ser Val Thr Ala Ala Asp Thr Ala Val Tyr Tyr Cys Ala
                85                  90                  95

Arg Asp Thr Tyr Tyr Tyr Asp Ser Gly Asp Tyr Glu Asp Ala Phe Asp
            100                 105                 110

Ile Trp Gly Gln Gly Thr Met Val Thr Val Ser Ser
        115                 120

<210> SEQ ID NO 2
<211> LENGTH: 112
<212> TYPE: PRT
<213> ORGANISM: Homo sapiens

<400> SEQUENCE: 2

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Asn Tyr Ala
```

```
                    20                  25                  30

Ile Ala Trp His Gln Gln Pro Gly Lys Gly Pro Arg Tyr Leu Met
         35                  40                  45

Lys Val Asn Arg Asp Gly Ser His Ile Arg Gly Asp Gly Ile Pro Asp
 50                  55                  60

Arg Phe Ser Gly Ser Thr Ser Gly Ala Glu Arg Tyr Leu Thr Ile Ser
65                   70                  75                  80

Ser Leu Gln Ser Glu Asp Glu Ala Asp Tyr Tyr Cys Gln Thr Trp Gly
                 85                  90                  95

Ala Gly Ile Arg Val Phe Gly Gly Gly Thr Lys Leu Thr Val Leu Gly
             100                 105                 110

<210> SEQ ID NO 3
<211> LENGTH: 124
<212> TYPE: PRT
<213> ORGANISM: Homo sapiens

<400> SEQUENCE: 3

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
             20                  25                  30

Tyr Trp Ser Trp Ile Arg Gln Ser Pro Gly Arg Gly Leu Glu Trp Ile
         35                  40                  45

Gly Tyr Ile His Tyr Ser Gly Ser Thr Asn Ser Asn Pro Ser Leu Lys
     50                  55                  60

Ser Arg Val Thr Ile Ser Val Asp Thr Ser Lys Asn Gln Val Ser Leu
65                   70                  75                  80

Lys Leu Gly Ser Val Thr Ala Ala Asp Thr Ala Ile Tyr Tyr Cys Ala
                 85                  90                  95

Arg Asp Thr Tyr Tyr Glu Ser Ser Gly His Trp Phe Asp Gly Leu Asp
             100                 105                 110

Val Trp Gly Gln Gly Thr Ser Val Thr Val Ser Ser
         115                 120

<210> SEQ ID NO 4
<211> LENGTH: 111
<212> TYPE: PRT
<213> ORGANISM: Homo sapiens

<400> SEQUENCE: 4

Gln Pro Val Leu Thr Gln Ser Pro Ser Ala Ser Ala Ser Leu Gly Ala
1               5                   10                  15

Ser Val Lys Leu Thr Cys Thr Leu Asp Ser Glu His Ser Arg Tyr Thr
             20                  25                  30

Ile Ala Trp His Gln Gln Pro Glu Lys Gly Pro Arg Tyr Leu Met
         35                  40                  45

Lys Val Lys Ser Asp Gly Ser His Ser Lys Gly Asp Gly Ile Thr Asp
     50                  55                  60

Arg Phe Ser Gly Ser Ser Ser Gly Ala Glu Arg Tyr Leu Thr Ile Ser
65                   70                  75                  80

Ser Leu Gln Ser Glu Asp Glu Ala Asp Tyr Tyr Cys Gln Thr Trp Gly
                 85                  90                  95

Pro Gly Ile Arg Val Phe Gly Gly Gly Thr Lys Leu Thr Val Leu
             100                 105                 110
```

```
<210> SEQ ID NO 5
<211> LENGTH: 124
<212> TYPE: PRT
<213> ORGANISM: Homo sapiens

<400> SEQUENCE: 5
```

Gln Val Gln Leu Val Gln Ser Gly Ala Glu Met Lys Arg Pro Gly Ala
1               5                   10                  15

Ser Val Lys Val Ser Cys Lys Ala Ser Gly Tyr Thr Phe Thr Asn Phe
            20                  25                  30

Gly Ile Ser Trp Val Arg Gln Ala Pro Gly Gln Gly Leu Glu Trp Ile
        35                  40                  45

Gly Trp Val Ser Thr Tyr Asn Gly Arg Thr Asn Tyr Ala Gln Lys Phe
    50                  55                  60

Arg Gly Arg Val Thr Met Thr Thr Asp Thr Ser Thr Asn Thr Ala Tyr
65                  70                  75                  80

Met Glu Leu Arg Ser Leu Gly Ser Asp Asp Thr Ala Val Phe Tyr Cys
                85                  90                  95

Ala Arg Asp Tyr Tyr Glu Thr Ser Gly Tyr Ala Tyr Asp Asp Phe Ala
            100                 105                 110

Ile Trp Gly Gln Gly Thr Leu Val Thr Val Ser Ser
        115                 120

```
<210> SEQ ID NO 6
<211> LENGTH: 112
<212> TYPE: PRT
<213> ORGANISM: Homo sapiens

<400> SEQUENCE: 6
```

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Thr Tyr Ala
            20                  25                  30

Ile Ala Trp His Gln Gln Gln Pro Leu Arg Gly Pro Arg Phe Leu Met
        35                  40                  45

Lys Val Asn Ser Asp Gly Ser His Thr Lys Gly Asp Gly Ile Pro Asp
    50                  55                  60

Arg Phe Ser Gly Ser Ser Ser Gly Ala Glu Arg Tyr Leu Ser Ile Ser
65                  70                  75                  80

Ser Leu Gln Ser Glu Asp Glu Ser Asp Tyr Tyr Cys Gln Thr Trp Gly
                85                  90                  95

Pro Gly Ile Arg Val Phe Gly Gly Gly Thr Lys Leu Thr Val Leu Gly
            100                 105                 110

```
<210> SEQ ID NO 7
<211> LENGTH: 5
<212> TYPE: PRT
<213> ORGANISM: Homo sapiens

<400> SEQUENCE: 7
```

Gly Tyr Tyr Trp Ser
1               5

```
<210> SEQ ID NO 8
<211> LENGTH: 16
<212> TYPE: PRT
<213> ORGANISM: Homo sapiens

<400> SEQUENCE: 8
```

```
Tyr Ile His Tyr Ser Arg Ser Thr Asn Ser Asn Pro Ala Leu Lys Ser
1               5                   10                  15

<210> SEQ ID NO 9
<211> LENGTH: 16
<212> TYPE: PRT
<213> ORGANISM: Homo sapiens

<400> SEQUENCE: 9

Asp Thr Tyr Tyr Tyr Asp Ser Gly Asp Tyr Glu Asp Ala Phe Asp Ile
1               5                   10                  15

<210> SEQ ID NO 10
<211> LENGTH: 12
<212> TYPE: PRT
<213> ORGANISM: Homo sapiens

<400> SEQUENCE: 10

Thr Leu Ser Ser Gly His Ser Asn Tyr Ala Ile Ala
1               5                   10

<210> SEQ ID NO 11
<211> LENGTH: 11
<212> TYPE: PRT
<213> ORGANISM: Homo sapiens

<400> SEQUENCE: 11

Val Asn Arg Asp Gly Ser His Ile Arg Gly Asp
1               5                   10

<210> SEQ ID NO 12
<211> LENGTH: 9
<212> TYPE: PRT
<213> ORGANISM: Homo sapiens

<400> SEQUENCE: 12

Gln Thr Trp Gly Ala Gly Ile Arg Val
1               5

<210> SEQ ID NO 13
<211> LENGTH: 5
<212> TYPE: PRT
<213> ORGANISM: Homo sapiens

<400> SEQUENCE: 13

Asn Tyr Tyr Trp Ser
1               5

<210> SEQ ID NO 14
<211> LENGTH: 16
<212> TYPE: PRT
<213> ORGANISM: Homo sapiens

<400> SEQUENCE: 14

Tyr Ile His Tyr Ser Gly Ser Thr Asn Ser Asn Pro Ser Leu Lys Ser
1               5                   10                  15

<210> SEQ ID NO 15
<211> LENGTH: 16
<212> TYPE: PRT
<213> ORGANISM: Homo sapiens

<400> SEQUENCE: 15

Asp Thr Tyr Tyr Glu Ser Ser Gly His Trp Phe Asp Gly Leu Asp Val
1               5                   10                  15
```

<210> SEQ ID NO 16
<211> LENGTH: 12
<212> TYPE: PRT
<213> ORGANISM: Homo sapiens

<400> SEQUENCE: 16

Thr Leu Asp Ser Glu His Ser Arg Tyr Thr Ile Ala
1               5                   10

<210> SEQ ID NO 17
<211> LENGTH: 11
<212> TYPE: PRT
<213> ORGANISM: Homo sapiens

<400> SEQUENCE: 17

Val Lys Ser Asp Gly Ser His Ser Lys Gly Asp
1               5                   10

<210> SEQ ID NO 18
<211> LENGTH: 9
<212> TYPE: PRT
<213> ORGANISM: Homo sapiens

<400> SEQUENCE: 18

Gln Thr Trp Gly Pro Gly Ile Arg Val
1               5

<210> SEQ ID NO 19
<211> LENGTH: 5
<212> TYPE: PRT
<213> ORGANISM: Homo sapiens

<400> SEQUENCE: 19

Asn Phe Gly Ile Ser
1               5

<210> SEQ ID NO 20
<211> LENGTH: 17
<212> TYPE: PRT
<213> ORGANISM: Homo sapiens

<400> SEQUENCE: 20

Trp Val Ser Thr Tyr Asn Gly Arg Thr Asn Tyr Ala Gln Lys Phe Arg
1               5                   10                  15

Gly

<210> SEQ ID NO 21
<211> LENGTH: 15
<212> TYPE: PRT
<213> ORGANISM: Homo sapiens

<400> SEQUENCE: 21

Asp Tyr Tyr Glu Thr Ser Gly Tyr Ala Tyr Asp Asp Phe Ala Ile
1               5                   10                  15

<210> SEQ ID NO 22
<211> LENGTH: 12
<212> TYPE: PRT
<213> ORGANISM: Homo sapiens

<400> SEQUENCE: 22

Thr Leu Ser Ser Gly His Ser Thr Tyr Ala Ile Ala
1               5                   10

```
<210> SEQ ID NO 23
<211> LENGTH: 11
<212> TYPE: PRT
<213> ORGANISM: Homo sapiens

<400> SEQUENCE: 23

Val Asn Ser Asp Gly Ser His Thr Lys Gly Asp
1               5                   10

<210> SEQ ID NO 24
<211> LENGTH: 9
<212> TYPE: PRT
<213> ORGANISM: Homo sapiens

<400> SEQUENCE: 24

Gln Thr Trp Gly Pro Gly Ile Arg Val
1               5

<210> SEQ ID NO 25
<211> LENGTH: 372
<212> TYPE: DNA
<213> ORGANISM: Homo sapiens

<400> SEQUENCE: 25
caggtgcagc tgcaggagtc gggcccagga ctggtgaagc cttcggagac cctgtccctc      60
acctgcactg tttctggtgg ctccatcagt ggttactact ggagttggat ccggcagccc     120
ccagggaagg gactggagtg gattgggtat attcattata gtaggagcac caactccaac     180
cccgccctca agagtcgagt caccatatca tcagacacgt ccaagaacca gctctccctg     240
agactgagct cagtgaccgc tgcggacacg gccgtgtatt actgtgcgag agataccctat    300 tactatgata gtggtgatta tgaggatgct tttgatattt ggggccaagg acaatggtc     360 accgtctcct ca                                                          372

<210> SEQ ID NO 26
<211> LENGTH: 336
<212> TYPE: DNA
<213> ORGANISM: Homo sapiens

<400> SEQUENCE: 26
cagcttgtgc tgactcagtc gccctctgcc tctgcctccc tgggagcctc ggtcaagctc      60
acctgcactc tgagcagtgg ccacagcaac tacgccatcg cttggcatca gcagcagcca     120
gggaagggcc ctcgctactt gatgaaggtt aacagagatg gcagccacat caggggggac     180
gggatccctg atcgcttctc aggctccacc tctggggctg agcgttacct caccatctcc     240
agtctccagt ctgaagatga ggctgactat tactgtcaga cctggggcgc tggcattcga    300
gtgttcggcg agggaccaa gctgaccgtc ctaggt                                336

<210> SEQ ID NO 27
<211> LENGTH: 372
<212> TYPE: DNA
<213> ORGANISM: Homo sapiens

<400> SEQUENCE: 27
caggtgcagc tgcaggagtc gggcccagga ctggtgaagc cttcggagac cctgtccctc      60
acgtgcactg tctctggtgg ctccatcagt aattactact ggagttggat ccggcagtcc     120
ccagggaggg gactggagtg gattgggtat atccattata gtgggagcac caactccaat     180
```

```
ccatccctca agagtcgagt caccatatca gttgacacgt ccaagaacca ggtctccctg      240
aagctgggct ctgtgaccgc tgcggacacg gccatatatt actgtgcgag agatacttac      300
tatgaaagta gtggtcattg gttcgacggt ttggacgtct ggggccaagg gacctcggtc      360
accgtctcct ca                                                          372

<210> SEQ ID NO 28
<211> LENGTH: 333
<212> TYPE: DNA
<213> ORGANISM: Homo sapiens

<400> SEQUENCE: 28
cagcctgtgc tgactcagtc gccctctgcc tctgcctccc tgggagcctc ggtcaagctc       60
acctgcactc tggacagtga acacagcaga tacaccatcg catggcatca gcagcagcca      120
gagaagggcc ctcggtacct gatgaaggtt aagagtgatg cagtcacag caaggggac        180 ggcattactg atcgcttctc aggctccagc tctggggctg agcgctacct caccatctcc      240
agcctccagt ctgaggatga ggctgactat tactgtcaga cttggggccc tggcattcga      300
gtgttcggcg agggaccaa gctgaccgtc cta                                    333

<210> SEQ ID NO 29
<211> LENGTH: 372
<212> TYPE: DNA
<213> ORGANISM: Homo sapiens

<400> SEQUENCE: 29
caggttcagc tggtgcagtc tggagctgag atgaagaggc ctggggcctc agtgaaggtc       60
tcctgcaagg cttctggtta ccctttacc aactttggta tcagttgggt gcgacaggcc      120
cctggacaag gcttgagtg gataggatgg gtcagcactt acaatggtcg cacaaattat      180
gcacagaagt tccggggcag agtcaccatg accacagaca catccacgaa cacagcgtac      240
atggaactga ggagcctggg atctgacgac acggccgtct tttactgtgc gagagattac      300
tatgagacta gtggttacgc ctatgatgat tttgcgatct ggggccaagg gacattggtc      360
accgtctcct ca                                                          372

<210> SEQ ID NO 30
<211> LENGTH: 336
<212> TYPE: DNA
<213> ORGANISM: Homo sapiens

<400> SEQUENCE: 30
cagcttgtgc tgactcaatc gccctctgcc tctgcttccc tgggagcctc ggtcaagctc       60
acctgcactc tgagcagtgg gcacagcacc tacgccatcg cgtggcatca gcagcagcca      120 ctgagggtc ctcgtttctt gatgaaagtc aacagtgatg cagccacac caaggggac        180 gggatccctg atcgcttctc aggctccagt tctggggctg agcgctacct ctccatctcc      240
agcctccagt ctgaagatga gtctgactat tactgtcaga cgtggggccc tggcattcga      300
gtgttcggcg agggaccaa gctgaccgtc ctaggt                                 336

<210> SEQ ID NO 31
<211> LENGTH: 15
<212> TYPE: PRT
<213> ORGANISM: Homo sapiens

<400> SEQUENCE: 31

Gly Gly Thr Thr Ala Cys Thr Ala Cys Thr Gly Gly Ala Gly Thr
```

<210> SEQ ID NO 32
<211> LENGTH: 48
<212> TYPE: PRT
<213> ORGANISM: Homo sapiens

<400> SEQUENCE: 32

Thr Ala Thr Ala Thr Thr Cys Ala Thr Thr Ala Thr Ala Gly Thr Ala
1               5                   10                  15

Gly Gly Ala Gly Cys Ala Cys Ala Ala Cys Thr Cys Cys Ala Ala
            20                  25                  30

Cys Cys Cys Cys Gly Cys Cys Thr Cys Ala Ala Gly Ala Gly Thr
        35                  40                  45

<210> SEQ ID NO 33
<211> LENGTH: 48
<212> TYPE: PRT
<213> ORGANISM: Homo sapiens

<400> SEQUENCE: 33

Gly Ala Thr Ala Cys Cys Thr Ala Thr Thr Ala Cys Thr Ala Thr Gly
1               5                   10                  15

Ala Thr Ala Gly Thr Gly Gly Thr Gly Ala Thr Thr Ala Thr Gly Ala
            20                  25                  30

Gly Gly Ala Thr Gly Cys Thr Thr Thr Thr Gly Ala Thr Ala Thr Thr
        35                  40                  45

<210> SEQ ID NO 34
<211> LENGTH: 36
<212> TYPE: PRT
<213> ORGANISM: Homosapiens

<400> SEQUENCE: 34

Ala Cys Thr Cys Thr Gly Ala Gly Cys Ala Gly Thr Gly Gly Cys Cys
1               5                   10                  15

Ala Cys Ala Gly Cys Ala Ala Cys Thr Ala Cys Gly Cys Cys Ala Thr
            20                  25                  30

Cys Gly Cys Thr
        35

<210> SEQ ID NO 35
<211> LENGTH: 33
<212> TYPE: PRT
<213> ORGANISM: Homo sapiens

<400> SEQUENCE: 35

Gly Thr Thr Ala Ala Cys Ala Gly Ala Gly Ala Thr Gly Gly Cys Ala
1               5                   10                  15

Gly Cys Cys Ala Cys Ala Thr Cys Ala Gly Gly Gly Gly Gly Ala
            20                  25                  30

Cys

<210> SEQ ID NO 36
<211> LENGTH: 27
<212> TYPE: PRT
<213> ORGANISM: Homo sapiens

<400> SEQUENCE: 36

Cys Ala Gly Ala Cys Cys Thr Gly Gly Gly Gly Cys Gly Cys Thr Gly
1               5                   10                  15

```
Gly Cys Ala Thr Thr Cys Gly Ala Gly Thr Gly
            20                  25
```

<210> SEQ ID NO 37
<211> LENGTH: 15
<212> TYPE: PRT
<213> ORGANISM: Homo sapiens

<400> SEQUENCE: 37

```
Ala Ala Thr Thr Ala Cys Thr Ala Cys Thr Gly Gly Ala Gly Thr
1               5                   10                  15
```

<210> SEQ ID NO 38
<211> LENGTH: 48
<212> TYPE: PRT
<213> ORGANISM: Homo sapiens

<400> SEQUENCE: 38

```
Thr Ala Thr Ala Thr Cys Cys Ala Thr Thr Ala Thr Ala Gly Thr Gly
1               5                   10                  15

Gly Gly Ala Gly Cys Ala Cys Cys Ala Ala Cys Thr Cys Cys Ala Ala
            20                  25                  30

Thr Cys Cys Ala Thr Cys Cys Cys Thr Cys Ala Ala Gly Ala Gly Thr
        35                  40                  45
```

<210> SEQ ID NO 39
<211> LENGTH: 48
<212> TYPE: PRT
<213> ORGANISM: Homo sapiens

<400> SEQUENCE: 39

```
Gly Ala Thr Ala Cys Thr Thr Ala Cys Thr Ala Thr Gly Ala Ala Ala
1               5                   10                  15

Gly Thr Ala Gly Thr Gly Gly Thr Cys Ala Thr Thr Gly Gly Thr Thr
            20                  25                  30

Cys Gly Ala Cys Gly Gly Thr Thr Thr Gly Gly Ala Cys Gly Thr Cys
        35                  40                  45
```

<210> SEQ ID NO 40
<211> LENGTH: 36
<212> TYPE: PRT
<213> ORGANISM: Homo sapiens

<400> SEQUENCE: 40

```
Ala Cys Thr Cys Thr Gly Gly Ala Cys Ala Gly Thr Gly Ala Ala Cys
1               5                   10                  15

Ala Cys Ala Gly Cys Ala Gly Ala Thr Ala Cys Ala Cys Cys Ala Thr
            20                  25                  30

Cys Gly Cys Ala
        35
```

<210> SEQ ID NO 41
<211> LENGTH: 33
<212> TYPE: PRT
<213> ORGANISM: Homo sapiens

<400> SEQUENCE: 41

```
Gly Thr Thr Ala Ala Gly Ala Gly Thr Ala Thr Gly Gly Cys Ala
1               5                   10                  15

Gly Thr Cys Ala Cys Ala Gly Cys Ala Ala Gly Gly Gly Gly Ala
            20                  25                  30
```

Cys

<210> SEQ ID NO 42
<211> LENGTH: 27
<212> TYPE: PRT
<213> ORGANISM: Homo sapiens

<400> SEQUENCE: 42

Cys Ala Gly Ala Cys Thr Thr Gly Gly Gly Cys Cys Cys Thr Gly
1               5                   10                  15

Gly Cys Ala Thr Thr Cys Gly Ala Gly Thr Gly
            20                  25

<210> SEQ ID NO 43
<211> LENGTH: 15
<212> TYPE: PRT
<213> ORGANISM: Homo sapiens

<400> SEQUENCE: 43

Ala Ala Cys Thr Thr Thr Gly Gly Thr Ala Thr Cys Ala Gly Thr
1               5                   10                  15

<210> SEQ ID NO 44
<211> LENGTH: 51
<212> TYPE: PRT
<213> ORGANISM: Homo sapiens

<400> SEQUENCE: 44

Thr Gly Gly Gly Thr Cys Ala Gly Cys Ala Cys Thr Thr Ala Cys Ala
1               5                   10                  15

Ala Thr Gly Gly Thr Cys Gly Cys Ala Cys Ala Ala Ala Thr Thr Ala
            20                  25                  30

Thr Gly Cys Ala Cys Ala Gly Ala Ala Gly Thr Thr Cys Cys Gly Gly
        35                  40                  45

Gly Gly Cys
    50

<210> SEQ ID NO 45
<211> LENGTH: 45
<212> TYPE: PRT
<213> ORGANISM: Homo sapiens

<400> SEQUENCE: 45

Gly Ala Thr Thr Ala Cys Thr Ala Thr Gly Ala Gly Ala Cys Thr Ala
1               5                   10                  15

Gly Thr Gly Gly Thr Thr Ala Cys Gly Cys Cys Thr Ala Thr Gly Ala
            20                  25                  30

Thr Gly Ala Thr Thr Thr Thr Gly Cys Gly Ala Thr Cys
        35                  40                  45

<210> SEQ ID NO 46
<211> LENGTH: 36
<212> TYPE: PRT
<213> ORGANISM: Homo sapiens

<400> SEQUENCE: 46

Ala Cys Thr Cys Thr Gly Ala Gly Cys Ala Gly Thr Gly Gly Gly Cys
1               5                   10                  15

Ala Cys Ala Gly Cys Ala Cys Cys Thr Ala Cys Gly Cys Cys Ala Thr
            20                  25                  30

-continued

Cys Gly Cys Gly
        35

<210> SEQ ID NO 47
<211> LENGTH: 33
<212> TYPE: PRT
<213> ORGANISM: Homo sapiens

<400> SEQUENCE: 47

Gly Thr Cys Ala Ala Cys Ala Gly Thr Gly Ala Thr Gly Gly Cys Ala
1               5                   10                  15

Gly Cys Cys Ala Cys Ala Cys Cys Ala Ala Gly Gly Gly Gly Gly Ala
            20                  25                  30

Cys

<210> SEQ ID NO 48
<211> LENGTH: 27
<212> TYPE: PRT
<213> ORGANISM: Homo sapiens

<400> SEQUENCE: 48

Cys Ala Gly Ala Cys Gly Thr Gly Gly Gly Cys Cys Cys Thr Gly
1               5                   10                  15

Gly Cys Ala Thr Thr Cys Gly Ala Gly Thr Gly
            20                  25

<210> SEQ ID NO 49
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 49
gaccgagggg gcagccttgg gctgacctag g                              31

<210> SEQ ID NO 50
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 50
agatctctca ccatggcatg gatccctctc ttc                            33

<210> SEQ ID NO 51
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 51
tgggcccttg gtgctagctg aggagac                                   27

<210> SEQ ID NO 52
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 52

```
gtcgacatga aacatctgtg gttcttc                                              27
```

<210> SEQ ID NO 53
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 53

```
agatctctca ccatggccrg cttccctctc ctc                                       33
```

<210> SEQ ID NO 54
<211> LENGTH: 22
<212> TYPE: DNA
<213> ORGANISM: Artificial sequence
<220> FEATURE:
<223> OTHER INFORMATION: Synthetic oligonucleotide

<400> SEQUENCE: 54

```
gtcgacatgg actggacctg ga                                                   22
```

<210> SEQ ID NO 55
<211> LENGTH: 126
<212> TYPE: PRT
<213> ORGANISM: Homo sapiens

<400> SEQUENCE: 55

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Gly Tyr
            20                  25                  30

Tyr Trp Ser Trp Ile Arg Gln Pro Pro Gly Lys Gly Leu Glu Trp Ile
        35                  40                  45

Gly Tyr Ile His Tyr Ser Arg Ser Thr Asn Ser Asn Pro Ala Leu Lys
    50                  55                  60

Ser Arg Val Thr Ile Ser Ser Asp Thr Ser Lys Asn Gln Leu Ser Leu
65                  70                  75                  80

Arg Leu Ser Ser Val Thr Ala Ala Asp Thr Ala Val Tyr Tyr Cys Ala
                85                  90                  95

Arg Asp Thr Tyr Tyr Tyr Asp Ser Gly Asp Tyr Glu Asp Ala Phe Asp
            100                 105                 110

Ile Trp Gly Gln Gly Thr Met Val Thr Val Ser Ser Ala Ser
        115                 120                 125
```

<210> SEQ ID NO 56
<211> LENGTH: 378
<212> TYPE: DNA
<213> ORGANISM: Homo sapiens

<400> SEQUENCE: 56

```
caggtgcagc tgcaggagtc gggcccagga ctggtgaagc cttcggagac cctgtccctc          60
acctgcactg tttctggtgg ctccatcagt ggttactact ggagttggat ccggcagccc         120
ccagggaagg gactggagtg gattgggtat attcattata gtaggagcac caactccaac         180
cccgccctca gagtcgagt caccatatca tcagacacgt ccaagaacca gctctccctg          240
agactgagct cagtgaccgc tgcggacacg gccgtgtatt actgtgcgag agataccrat         300
tactatgata gtggtgatta tgaggatgct tttgatattt ggggccaagg gacaatggtc         360
accgtctcct cagctagc                                                       378
```

<210> SEQ ID NO 57
<211> LENGTH: 120
<212> TYPE: PRT
<213> ORGANISM: Homo sapiens

<400> SEQUENCE: 57

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Asn Tyr Ala
            20                  25                  30

Ile Ala Trp His Gln Gln Pro Gly Lys Gly Pro Arg Tyr Leu Met
        35                  40                  45

Lys Val Asn Arg Asp Gly Ser His Ile Arg Gly Asp Gly Ile Pro Asp
50                  55                  60

Arg Phe Ser Gly Ser Thr Ser Gly Ala Glu Arg Tyr Leu Thr Ile Ser
65                  70                  75                  80

Ser Leu Gln Ser Glu Asp Glu Ala Asp Tyr Tyr Cys Gln Thr Trp Gly
                85                  90                  95

Ala Gly Ile Arg Val Phe Gly Gly Gly Thr Lys Leu Thr Val Leu Gly
            100                 105                 110

Gln Pro Lys Ala Ala Pro Ser Val
        115                 120

<210> SEQ ID NO 58
<211> LENGTH: 130
<212> TYPE: PRT
<213> ORGANISM: Homo sapiens

<400> SEQUENCE: 58

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Asn Tyr
            20                  25                  30

Tyr Trp Ser Trp Ile Arg Gln Ser Pro Gly Arg Gly Leu Glu Trp Ile
        35                  40                  45

Gly Tyr Ile His Tyr Ser Gly Ser Thr Asn Ser Asn Pro Ser Leu Lys
50                  55                  60

Ser Arg Val Thr Ile Ser Val Asp Thr Ser Lys Asn Gln Val Ser Leu
65                  70                  75                  80

Lys Leu Gly Ser Val Thr Ala Ala Asp Thr Ala Ile Tyr Tyr Cys Ala
                85                  90                  95

Arg Asp Thr Tyr Tyr Glu Ser Ser Gly His Trp Phe Asp Gly Leu Asp
            100                 105                 110

Val Trp Gly Gln Gly Thr Ser Val Thr Val Ser Ser Ala Ser Thr Lys
        115                 120                 125

Gly Pro
    130

<210> SEQ ID NO 59
<211> LENGTH: 381
<212> TYPE: DNA
<213> ORGANISM: Homo sapiens

<400> SEQUENCE: 59
caggtgcagc tgcaggagtc gggcccagga ctggtgaagc cttcggagac cctgtccctc      60
acgtgcactg tctctggtgg ctccatcagt aattactact ggagttggat ccggcagtcc     120

```
                                                    -continued ccagggaggg gactggagtg gattgggtat atccattata gtgggagcac caactccaat    180
ccatccctca agagtcgagt caccatatca gttgacacgt ccaagaacca ggtctccctg    240
aagctgggct ctgtgaccgc tgcggacacg gccatatatt actgtgcgag agatacttac    300
tatgaaagta gtggtcattg gttcgacggt ttggacgtct ggggccaagg gacctcggtc    360
accgtctcct cagctagcac c                                              381

<210> SEQ ID NO 60
<211> LENGTH: 120
<212> TYPE: PRT
<213> ORGANISM: Homo sapiens

<400> SEQUENCE: 60

Gln Leu Val Leu Thr Gln Ser Pro Ser Ala Ser Ala Ser Leu Gly Ala
1               5                   10                  15

Ser Val Lys Leu Thr Cys Thr Leu Ser Ser Gly His Ser Thr Tyr Ala
            20                  25                  30

Ile Ala Trp His Gln Gln Pro Leu Arg Gly Pro Arg Phe Leu Met
        35                  40                  45

Lys Val Asn Ser Asp Gly Ser His Thr Lys Gly Asp Gly Ile Pro Asp
    50                  55                  60

Arg Phe Ser Gly Ser Ser Ser Gly Ala Glu Arg Tyr Leu Ser Ile Ser
65                  70                  75                  80

Ser Leu Gln Ser Glu Asp Glu Ser Asp Tyr Tyr Cys Gln Thr Trp Gly
                85                  90                  95

Pro Gly Ile Arg Val Phe Gly Gly Gly Thr Lys Leu Thr Val Leu Gly
            100                 105                 110

Gln Pro Lys Ala Ala Pro Ser Val
        115                 120

<210> SEQ ID NO 61
<211> LENGTH: 375
<212> TYPE: DNA
<213> ORGANISM: Homo sapiens

<400> SEQUENCE: 61
cagcttgtgc tgactcaatc gccctctgcc tctgcttccc tgggagcctc ggtcaagctc     60
acctgcactc tgagcagtgg gcacagcacc tacgccatcg cgtggcatca gcagcagcca    120
ctgaggggtc ctcgtttctt gatgaaagtc aacagtgatg gcagccacac caaggggggac   180 gggatccctg atcgcttctc aggctccagt tctggggctg agcgctacct ctccatctcc    240
agcctccagt ctgaagatga gtctgactat tactgtcaga cgtggggccc tggcattcga    300
gtgttcggcg gagggaccaa gctgaccgtc ctaggtcagc ccaaggctgc cccatcggtc    360
acctgttccc gcctc                                                    375
```

What is claimed is:

1. A composition, comprising an isolated peptide comprising the sequence of SEQ ID NO: 1.

2. The composition of claim 1, further comprising a Staphylococcal PNAG/dPNAG-binding CDR that is Staphylococcal PNAG/dPNAG-binding CDR3.

3. The composition of claim 1, wherein the isolated peptide further comprises an amino acid sequence of a light chain variable region derived from deposited hybridomas having Accession Nos. PTA-5931, PTA-5932 or PTA-5933.

4. The composition of claim 1, wherein the isolated peptide is an isolated antibody or antibody fragment.

5. The composition of claim 4, wherein the isolated antibody or antibody fragment is an intact soluble monoclonal antibody.

6. The composition of claim 4, wherein the isolated antibody or antibody fragment is an isolated antibody fragment selected from the group consisting of an F(ab')2 fragment, an Fd fragment and an Fab fragment.

7. The composition of claim 4, wherein the isolated antibody or antibody fragment comprises an amino acid sequence of a light chain variable region derived from deposited hybridoma having Accession No. PTA-5931 (F598).

8. The composition of claim 1, wherein the isolated peptide is conjugated to a detectable label.

9. The composition of claim 8, wherein the detectable label is an in vivo detectable label.

10. The composition of claim 1, wherein the isolated peptide selectively binds to Staphylococcal PNAG.

11. The composition of claim 1, wherein the isolated peptide selectively binds to Staphylococcal dPNAG.

12. An isolated cell producing an anti-Staphylococcal PNAG/dPNAG monoclonal antibody and having ATCC Accession No. PTA-5931.

13. A composition, comprising:
an F598 peptide produced by a hybridoma having ATCC Accession No. PTA-5931;
wherein the peptide comprises the sequences of SEQ ID NO: 1 and SEQ ID NO: 2; and
further wherein the peptide comprises the sequences of SEQ ID NO: 9 and SEQ ID NO: 12.

14. The composition of claim 13, wherein the peptide comprises the sequences of SEQ ID NO: 7 and SEQ ID NO: 10; or the peptide comprises the sequences of SEQ ID NO: 8 and SEQ ID NO: 11.

15. The composition of claim 13, wherein the peptide comprises the sequences of SEQ ID NO: 7, SEQ ID NO: 10, SEQ ID NO: 8 and SEQ ID NO: 11.

* * * * *

UNITED STATES PATENT AND TRADEMARK OFFICE
CERTIFICATE OF CORRECTION

| | | |
|---|---|---|
| PATENT NO. | : 7,786,255 B2 | |
| APPLICATION NO. | : 11/111688 | |
| DATED | : August 31, 2010 | |
| INVENTOR(S) | : Gerald B. Pier et al. | |

It is certified that error appears in the above-identified patent and that said Letters Patent is hereby corrected as shown below:

Please delete the Sequence Listing appearing on Column 65, line 39 to Column 73, line 21 and replace with the correct Sequence Listing on the attached pages.

Signed and Sealed this
Twenty-eighth Day of June, 2011

David J. Kappos
*Director of the United States Patent and Trademark Office*

```
<210> 31
<211> 15
<212> DNA
<213> Homo sapiens

<400> 31
ggttactact ggagt                                                         15

<210> 32
<211> 48
<212> DNA
<213> Homo sapiens

<400> 32
tatattcatt atagtaggag caccaactcc aacccgccc tcaagagt                      48

<210> 33
<211> 48
<212> DNA
<213> Homo sapiens

<400> 33
gatacctatt actatgatag tggtgattat gaggatgctt ttgatatt                     48

<210> 34
<211> 36
<212> DNA
<213> Homosapiens

<400> 34
actctgagca gtggccacag caactacgcc atcgct                                  36

<210> 35
<211> 33
<212> DNA
<213> Homo sapiens

<400> 35
gttaacagag atggcagcca catcagggggg gac                                    33

<210> 36
<211> 27
<212> DNA
<213> Homo sapiens
```

<400> 36
cagacctggg gcgctggcat tcgagtg						27

<210> 37
<211> 15
<212> DNA
<213> Homo sapiens

<400> 37
aattactact ggagt						15

<210> 38
<211> 48
<212> DNA
<213> Homo sapiens

<400> 38
tatatccatt atagtgggag caccaactcc aatccatccc tcaagagt						48

<210> 39
<211> 48
<212> DNA
<213> Homo sapiens

<400> 39
gatacttact atgaaagtag tggtcattgg ttcgacggtt tggacgtc						48

<210> 40
<211> 36
<212> DNA
<213> Homo sapiens

<400> 40
actctggaca gtgaacacag cagatacacc atcgca						36

<210> 41
<211> 33
<212> DNA
<213> Homo sapiens

<400> 41
gttaagagtg atggcagtca cagcaagggg gac						33

```
<210>  42
<211>  27
<212>  DNA
<213>  Homo sapiens

<400>  42 cagacttggg gccctggcat tcgagtg                                              27

<210>  43
<211>  15
<212>  DNA
<213>  Homo sapiens

<400>  43 aactttggta tcagt                                                           15

<210>  44
<211>  51
<212>  DNA
<213>  Homo sapiens

<400>  44 tgggtcagca cttacaatgg tcgcacaaat tatgcacaga agttccgggg c                   51

<210>  45
<211>  45
<212>  DNA
<213>  Homo sapiens

<400>  45 gattactatg agactagtgg ttacgcctat gatgattttg cgatc                          45

<210>  46
<211>  36
<212>  DNA
<213>  Homo sapiens

<400>  46 actctgagca gtgggcacag cacctacgcc atcgcg                                    36

<210>  47
<211>  33
```

```
<212>  DNA
<213>  Homo sapiens

<400>  47 gtcaacagtg atggcagcca caccaagggg gac                               33

<210>  48
<211>  27
<212>  DNA
<213>  Homo sapiens

<400>  48 cagacgtggg gccctggcat tcgagtg                                      27
```